United States Patent
Alstermark et al.

(12) 
(10) Patent No.: US 6,291,475 B1
(45) Date of Patent: Sep. 18, 2001

(54) BISPIDINE ANTIARRHYTHMIC COMPOUNDS

(75) Inventors: Christer Alstermark, Mölndal; Annika Björe, Stenungsund; Magnus Björsne, Västra Frölunda; Marianne Frantsi, Kungsbacka; Torbjörn Halvarsson, Vallda; Kurt-Jürgen Hoffmann, Kullavik; Eva-Lotte Lindstedt, Mölndal; Magnus Polla, Göteborg; Gert Strandlund, Lindome, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/214,756
(22) PCT Filed: Dec. 10, 1998
(86) PCT No.: PCT/SE98/02276
§ 371 Date: Jan. 12, 1999
§ 102(e) Date: Jan. 12, 1999
(87) PCT Pub. No.: WO99/31100
PCT Pub. Date: Jun. 24, 1999

(30) Foreign Application Priority Data

Dec. 17, 1997 (SE) .................................................. 9704709

(51) Int. Cl.⁷ ..................... A61K 31/439; C07D 471/08; C07D 471/20; A61P 9/06
(52) U.S. Cl. ............................ 514/300; 546/122
(58) Field of Search ............................ 514/300; 546/122

(56) References Cited

U.S. PATENT DOCUMENTS

| 3,962,449 | 6/1976 | Binnig et al. | 424/267 |
|---|---|---|---|
| 4,459,301 | 7/1984 | Binnig et al. | 424/267 |
| 4,550,112 | 10/1985 | Schoen et al. | 514/278 |
| 4,556,662 | 12/1985 | Binnig et al. | 574/300 |
| 4,959,373 | * 9/1990 | Lubisch | 514/300 |
| 5,468,858 | 11/1995 | Berlin et al. | 546/18 |

FOREIGN PATENT DOCUMENTS

| 0 306 871 | 3/1989 | (EP) . |
|---|---|---|
| 0 306 871 A2 | 3/1989 | (EP) . |
| 0 308 843 | 3/1989 | (EP) . |
| 0 655 228 A1 | 5/1995 | (EP) . |
| 91/07405 | 5/1991 | (WO) . |
| 9107405 A1 | 5/1991 | (WO) . |

OTHER PUBLICATIONS

Patani GA and Lavoie EJ. Chem. Rev. 96, 3147, 1996.*
King FD. Medicinal Chemistry:Principles and Practices. The Royal Society of Chemistry. Pp 206–208, 1994.*
Yamawaki et al, "Synthesis and Biological Activity of the Metabolites of . . .," Chem. Pharm. Bull., vol. 42, No. 11, pp. 2365–2369 (1994).
Horlein, U., "Ueber unsymmetrisch N–substituierte Bispidine . . . ", Eur. J. Med. Chem.—Chemica Therapeutica, vol. 12, No. 4, pp. 301–305 (1977).

* cited by examiner

*Primary Examiner*—Evelyn Mei Huang
(74) *Attorney, Agent, or Firm*—Nixon & Vanderhye

(57) ABSTRACT

There is provided a compound of formula I,

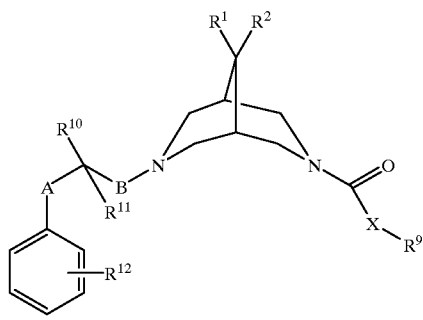

wherein $R^1$, $R^2$, $R^9$, $R^{10}$, $R^{11}$, $R^{12}$, X, A and B have meanings given in the description, which are useful in the prophylaxis and in the treatment of arrhythmias, in particular atrial and ventricular arrhythmias.

30 Claims, No Drawings

BISPIDINE ANTIARRHYTHMIC COMPOUNDS

This application is the national phase of PCT/SE98/02276, filed on Dec. 10, 1998.

FIELD OF THE INVENTION

This invention relates to novel pharmaceutically useful compounds, in particular compounds which are useful in the treatment of cardiac arrhythmias.

BACKGROUND AND PRIOR ART

Cardiac arrhythmias may be defined as abnormalities in the rate, regularity, or site of origin of the cardiac impulse or as disturbances in conduction which causes an abnormal sequence of activation. Arrhythmias may be classified clinically by means of the presumed site of origin (i.e. as supraventricular, including atrial and atrioventricular, arrhythmias and ventricular arrhythmias) and/or by means of rate (i.e. bradyarrhythmias (slow) and tachyarrhythmias (fast)).

In the treatment of cardiac arrhythmias, the negative outcome in clinical trials (see, for example, the outcome of the Cardiac Arrhythmia Suppression Trial (CAST) reported in New England Journal of Medicine, 321, 406 (1989)) with "traditional" antiarrhythmic drugs, which act primarily by slowing the conduction velocity (class I antiarrhthtmic drugs), has prompted drug development towards compounds which selectively delay cardiac repolarization, thus prolonging the QT interval. Class III antiarrhythmic drugs may be defined as drugs which prolong the trans-membrane action potential duration (which can be caused by a block of outward $K^+$ currents or from an increase of inward ion currents) and refractoriness, without affecting cardiac conduction.

One of the key disadvantages of hitherto known drugs which act by delaying repolarization (class III or otherwise) is that they all are known to exhibit a unique form of proarrhythmia known as torsades de pointes (turning of points), which may, on occasion be fatal. From the point of view of safety, the mininisation of this phenomenon (which has also been shown to be exhibited as a result of administration of non-cardiac drugs such as phenothiazines, tricyclic antidepressants, antihistamines and antibiotics) is a key problem to be solved in the provision of effective antiarrhythmic drugs.

Most antiarrhythmic drugs (including class III antiarrhythmic drugs) have a duration of action of between 3 and 12 hours. For example, the recently registered (approved, as of December 1997, in the US, Sweden, the UK, Denmark, Belgium, Netherlands, Finland, Italy and Austria) selective class III antiarrhythmic drug ibutilide (Pharmacia Upjohn) has a half-life of elimination which averages at around 6 hours when the drug is administered intravenously to a human patient.

In the minimisation of the side effects (including torsades de pointes) associated with antiarrhythmic drugs, compounds which are effective, yet short acting, when administered intravenously, are expected to be of benefit. Accordingly, compounds which have a duration of action which is relatively short (hereinafter referred to as "short acting compounds") may be expected to have clinical advantages when used in the acute conversion of arrhythmias, including reduced monitoring and hospitalisation time. By "short acting" in this context, we mean a half life ($t_{1/2}$), as measured in the test described below, of between 1 and 120 minutes, preferably between 1 and 60 minutes, more preferably between 1 and 30 minutes and especially between 1 and 15 minutes.

Antiarrhythmic drugs based on bispidines (3,7-diazabicyclo[3.3.1]nonanes), are known from inter alia international patent application WO 91/07405, European patent applications 306 871, 308 843 and 655 228 and U.S. Pat. Nos. 3,962,449, 4,556,662, 4,550,112, 4,459,301 and 5,468,858, as well as journal articles including inter alia J. Med. Chem. 39, 2559, (1996), Pharmacol. Res., 24, 149 (1991), Circulation, 90, 2032 (1994) and Anal. Sci. 9, 429, (1993). Known bispidine-based antiarrhythmic compounds include bisaramil (3-methyl-7-ethyl-9α,4'-(C1-benzoyloxy)-3,7-diazabicyclo[3.3.1]nonane), tedisamil (3',7'-bis(cyclopropylmethyl)spiro(cyclopentane-1,9'-3,7]diazabicyclo-[3.3.1]nonane), SAZ-VII-22 (3-(4-chlorobenzoyl)-7-isopropyl-3,7-diazabicyclo[3.3.1]nonane), SAZ-VII-23 (3-benzoyl-7-isopropyl-3,7-diazabicyclo[3.3.1]nonane), GLG-V-13 (3-[4-(1H-imidazol-1-yl)benzoyl]-7-isopropyl-3,7-diazabicyclo[3.3.1]nonane), KMC-IV-84 (7-[4'-(1H-imidazolo-1-yl)benzenesulphonyl]-3-isopropyl-3,7-diaza-bicyclo[3.3.1]nonane dihydroperchlorate and ambasilide (3-(4-aminobenzoyl)-7-benzyl-3,7-diazabicyclo[3.3.1 ]nonane).

We have surprisingly found that a novel group of bispidine-based compounds exhibit electrophysiological activity, preferably class III electrophysiological activity, and in particular short-acting class III electrophysiological activity, and are therefore expected to be useful in the treatment of cardiac arrhythmias.

DISCLOSURE OF THE INVENTION

According to the invention there is provided a compound of formula I,

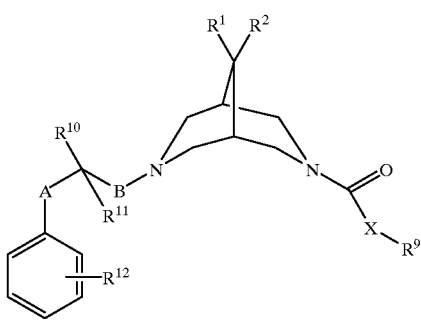

wherein $R^1$ and $R^2$ independently represent H, $C_{1-4}$ alkyl or together form —O—$(CH_2)_2$—O—, —$(CH_2)_4$— or —$(CH_2)_5$—;

$R^9$ represents $C_{1-12}$ alkyl, phenyl, naphthyl, $C_{1-3}$ alkylphenyl (which four groups are all optionally substituted or terminated by one or more substituents selected from —OH, halo, cyano, nitro, $C_{1-4}$ alkyl or $C_{1-4}$ alkoxy) or —$(CH_2)_q Cy^1$;

$R^{10}$ represents H or —OH;

$R^{11}$ represents H or $C_{1-4}$ alkyl;

$R^{12}$ represents one or more optional substituents selected from OH, cyano, halo, amino, nitro, $C_{1-6}$ alkyl, $C_{1-6}$ alkoxy, —N(H)S(O)$_2R^{16}$, —OS(O)$_2R^{16a}$, —N(H)C(O)N(H)$R^{17}$ or —C(O)N(H)$R^{18}$;

A represents a single bond, $C_{1-4}$ alkylene, —$(CH_2)_n$N($R^{20}$)—, —$(CH_2)_n$S(O)$_p$—, —$(CH_2)_n$O— (in which three latter groups, the —(CH$_2$)$_n$— group is attached to the carbon atom bearing R$^{10}$ and R$^{11}$), —C(O)N(R$^{20}$)— (in which latter group, the —C(O)— group is attached to the carbon atom bearing R$^{10}$ and R$^{11}$), —N(R$^{20}$)C(O)O(CH$_2$)$_n$—, —N(R$^{20}$)(CH$_2$)$_n$— (in which two latter groups, the N(R$^{20}$) group is attached to the carbon atom bearing R$^{10}$ and R$^{11}$) or —(CH$_2$)$_m$C(H)(OH)(CH$_2$)$_n$— (in which latter group, the —(CH$_2$)$_m$— group is attached to the carbon atom bearing R$^{10}$ and R$^{11}$);

B represents a single bond, C$_{1-6}$ alkylene, —N(R$^{23}$)(CH$_2$)$_r$— or —O(CH$_2$)$_r$— (in which two latter groups, the —(CH$_2$)$_r$— group is attached to the bispidine nitrogen atom);

m represents 1, 2 or 3;

n and r independently represent 0, 1, 2, 3 or 4;

p represents 0, 1 or 2;

q represents 0, 1, 2 or 3;

X represents O or S;

Cy$^1$ represents a five to seven-membered heterocyclic ring containing one or more heteroatom selected from O, N or S, which ring is optionally 15 substituted by one or more substituent selected from C(O)R$^{21}$ or C(O)OR$^{22}$;

R$^{16}$, R$^{16a}$, R$^{20}$ and R$^{23}$ independently represent H or C$_{1-4}$ alkyl; and R$^{17}$, R$^{18}$, R$^{21}$ and R$^{22}$ independently represent H or C$_{1-6}$ alkyl;

or a pharmaceutically acceptable derivative thereof.

Pharmaceutically acceptable derivatives include salts and solvates. Salts which may be mentioned include acid addition salts. Pharmaceutically acceptable derivatives also include, at the bispidine nitrogens, C$_{1-4}$ alkyl quaternary ammonium salts and N-oxides, provided that, when a N-oxide is present at a bispidine nitrogen, X does not represent S and/or p does not represent 0 when A represents —(CH$_2$)$_n$S(O)$_p$—.

The compounds of the invention may exhibit tautomerism. All tautomeric forms and mixtures thereof are included within the scope of the invention. The compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

Alkyl groups which R$^1$, R$^2$, R$^9$, R$^{11}$, R$^{12}$, R$^{16}$ R$^{16a}$, R$^{17}$ R$^{18}$, R$^{20}$ R$^{21}$ R$^{22}$, and R$^{23}$ may represent, and with which R$^9$ may be substituted, may be linear or branched, may be saturated or unsaturated, may be cyclic, acyclic or part cyclic/acyclic, and may be interrupted by oxygen and/or substituted by one or more fluoro or hydroxy group. Alkylene groups which A and B may represent, and —(CH$_2$)$_m$—, —(CH$_2$)$_n$—, —(CH$_2$)$_q$— and —(CH$_2$)$_r$— chains which A, B and R$^9$ (as appropriate) may include, may be linear or branched, may be saturated or unsaturated, may be cyclic or acyclic and may be interrupted by oxygen. Alkoxy groups which R$^{12}$ may represent, and with which R$^9$ may be substituted, may be linear or branched, may be saturated or unsaturated and may be cyclic or acyclic. Alkylphenyl groups which R$^9$ may represent may be linear or branched and may be saturated or unsaturated.

Heterocyclic groups which Cy$^1$ may represent may be aromatic or non-aromatic in character.

Halo groups which R$^{12}$ may represent, and with which R$^9$ may be substituted, include fluoro, chloro, bromo and iodo.

Abbreviations are listed at the end of this specification.

Preferred compounds of the invention include those in which:

R$^1$ represents H, C$_{1-4}$ alkyl or, together with R$^2$, represents —O(CH$_2$)$_2$O— or —(CH$_2$)$_4$—;

R$^2$ represents H or together with R$^1$ represents —O(CH$_2$)$_2$O— or —(CH$_2$)$_4$—;

R$^9$ represents optionally substituted phenyl, optionally substituted C$_{1-3}$ alkylphenyl, optionally substituted, optionally unsaturated, linear, branched or cyclic, C$_{1-12}$ alkyl (which latter group may also be interrupted by an O atom), or —(CH$_2$)$_q$Cy$^1$;

R$^{11}$ represents H, CH$_3$ or CH$_2$OH;

R$^{12}$ is absent or represents one or more substituents selected from cyano, OH, nitro, N(H)S(O)$_2$R$^{16}$, N(H)C(O)N(H)R$^{17}$, C(O)N(H)R$^{18}$, OS(O)$_2$R$^{16a}$, amino and C$_{1-6}$ alkyl;

X represents O;

A represents a single bond, O, —CH$_2$—, —(CH$_2$)$_2$—, —CH$_2$O—, —(CH$_2$)$_2$O—, —CH$_2$S—, —CH$_2$N(R$^{20}$)—, —C(O)N(R$^{20}$)—, —N(R$^{20}$)C(O)O(CH$_2$)$_n$—, —CH$_2$CH(OH)— or N(R$^{20}$)(CH$_2$)$_n$—;

B represents optionally unsaturated, linear or branched, C$_{1-4}$ alkylene (which group is also optionally interrupted by O);

when the bispidine nitrogen bearing B optionally bears a C$_{1-4}$ alkyl group, thus forming a quaternary ammonium salt, the alkyl group is a methyl group.

When R$^{12}$ represents a substituent in the para position (e.g. when a single substituent is present in this position), preferred substituents include cyano, nitro and N(H)S(O)$_2$R$^{16}$ (in which latter group R$^{16}$ represents C$_{1-3}$ alkyl, especially methyl, ethyl or n-propyl).

When R$^9$ represents —(CH$_2$)$_q$Cy$^1$, preferred compounds of the invention include those in which q is 0, 1 or 2 and Cy$^1$ contains at least one nitrogen atom (e.g. Cy$^1$ represents a six-membered ring containing one or two nitrogen atoms). Preferred ring systems that may be represented by Cy$^1$ include piperidine and piperazine (e.g. piperidin-4-yl and piperazin-1-yl). Preferred optional substituents on the ring include those in which R$^{21}$ and R$^{22}$ independently represent C$_{1-4}$ alkyl, preferably substituted in the 4 position relative to the point of attachment to —(CH$_2$)$_q$—.

More preferred compounds of the invention include the compounds of Examples 1 to 74 described hereinafter.

Particularly preferred compounds of the invention include those in which:

R$^1$ represents H;

R$^2$ represents H;

R$^9$ represents linear or branched C$_{2-7}$ alkyl, particularly linear C$_{3-6}$ alkyl and especially branched C$_{3-6}$ alkyl (e.g. iso-propyl, iso-butyl or tert-butyl);

R$^{10}$ represents —OH;

R$^{11}$ represents H;

R$^{12}$ represents cyano, particularly in the para position relative to A;

A represents a single bond or —CH$_2$O—;
B represents —CH$_2$— or —(CH$_2$)$_2$—.

Preparation

According to the invention there is also provided a process for the preparation of compounds of formula I which comprises:

(a) reaction of a compound of formula II,

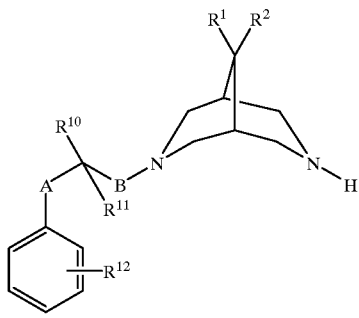

II wherein R$^1$, R$^2$, R$^{10}$, R$^{11}$, R$^{12}$, A and B are as hereinbefore defined with a compound of formula III,

III wherein L$^1$ represents a leaving group, such as Hal, imidazolyl or —OC(O)XR$^9$, Hal represents Cl, Br or I, and R$^9$ and X are as hereinbefore defined, for example at or above room temperature in the presence of a suitable base (e.g. aqueous NaOH, K$_2$CO$_3$ or TEA) and an appropriate organic solvent (e.g. DCM, THF, acetonitrile, toluene, or mixtures of such solvents);

(b) for compounds of formula I in which B represents CH$_2$ and R$^{10}$ represents OH, reaction of a compound of formula IV,

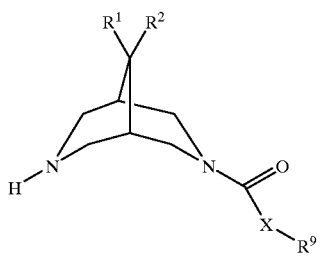

IV wherein R$^1$, R$^2$, R$^9$ and X are as hereinbefore defined, with a compound of formula V,

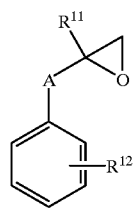

V wherein R$^{11}$, R$^{12}$ and A are as hereinbefore defined, for example at elevated temperature (e.g. 60° C. to reflux) in the presence of a suitable solvent (e.g. a lower alkyl alcohol (e.g. IPA), acetonitrile, or a mixture of a lower alkyl alcohol and water);

(c) reaction of a compound of formula IV, as hereinbefore defined, with a compound of formula VI,

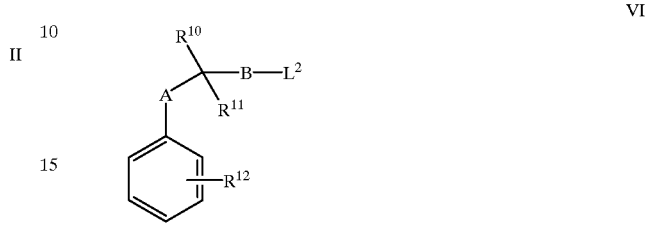

VI wherein L$^2$ represents a leaving group (e.g. mesylate, tosylate or Hal, where Hal is as hereinbefore defined) and R$^{10}$, R$^{11}$, R$^{12}$, A and B are as hereinbefore defined, for example at elevated temperature (e.g. between 35° C. and reflux temperature) in the presence of a suitable base (e.g. TEA or K$_2$CO$_3$) and an appropriate organic solvent (e.g. acetonitrile or DMSO);

(d) for compounds of formula I in which R$^{11}$ represents H, reduction of a compound of formula VIII,

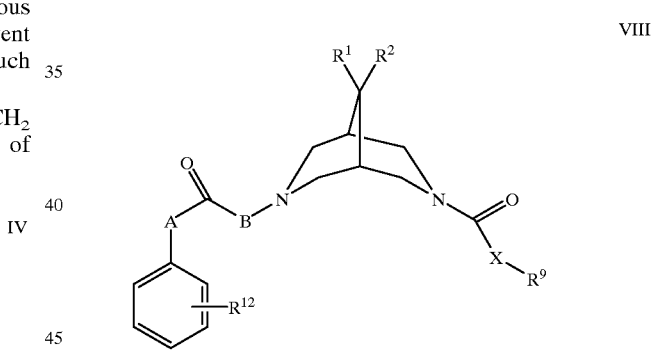

VIII wherein R$^1$, R$^2$, R$^9$, R$^{12}$, A, B and X are as hereinbefore defined, in the presence of a suitable reducing agent and under appropriate reaction conditions; for example, for formation of compounds of formula I in which R$^{10}$ represents OH, reduction may be performed under mild reaction conditions in the presence of e.g. sodium borohydride and an appropriate organic solvent (e.g. THF); and for formation of compounds of formula I in which R$^{10}$ represents H, reduction may be performed by activating the C=O group using an appropriate agent (such as tosylhydrazine) in the presence of a suitable reducing agent (e.g. sodium borohydride or sodium cyanoborohydride) and an appropriate organic solvent (e.g. a lower alkyl alcohol);

(e) for compounds of formula I in which R$^1$ and R$^2$ both represent H, reduction of a corresponding compound of formula IX,

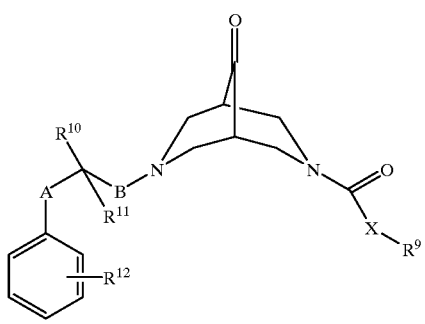

IX wherein $R^9$, $R^{10}$, $R^{11}$, $R^{12}$, X, A and B are as hereinbefore defined, and in which the C=O group may be activated using an appropriate agent, such as tosylhydrazine, in the presence of a suitable reducing agent (e.g. sodium borohydride or sodium cyanoborohydride) and an appropriate organic solvent (e.g. a lower alkyl alcohol); when the C=O group is activated, the activation step may be carried out at between room and reflux temperature in the presence of an appropriate organic solvent (e.g. a lower alkyl alcohol such as methanol, ethanol or IPA), whereafter the reducing agent may be added to the reaction mixture and the reduction carried out at between 60° C. and reflux, advantageously in the presence of a suitable organic acid (e.g. acetic acid);

(f) for compounds of formula I in which $R^1$ and $R^2$ together represent —O(CH$_2$)$_2$O—, reaction of a corresponding compound of formula IX as hereinbefore defined with ethane-1,2-diol under appropriate reaction conditions, for example, provided that $R^9$ does not represent tert-butyl, by refluxing in the presence of pTSA and an appropriate organic solvent (e.g. toluene), or, when $R^9$ represents tert-butyl, under mild and/or non-acidic conditions such as those which are known to those skilled in the art;

(g) for compounds of formula I which are bispidine-nitrogen N-oxide derivatives, oxidation of the corresponding bispidine nitrogen of a corresponding compound of formula I, in the presence of a suitable oxidising agent (e.g. mCPBA), for example at 0° C. in the presence of a suitable organic solvent (e.g. DCM);

(h) for compounds of formula I which are C$_{1-4}$ alkyl quaternary ammonium salt derivatives, in which the alkyl group is attached to a bispidine nitrogen, reaction, at the bispidine nitrogen, of a corresponding compound of formula I with a compound of formula XI, $R^b$Hal  XI wherein $R^b$ represents C$_{1-4}$ alkyl and Hal is as hereinbefore defined, for example at room temperature in the presence of an appropriate organic solvent (e.g. DMF), followed by purification (using e.g. HPLC) in the presence of a suitable counter-ion provider (e.g. NH$_4$OAc);

(i) for compounds of formula I in which $R^{10}$ and $R^{11}$ represent H, B represents C$_{1-6}$ alkylene and A represents —N(R$^{20}$)(CH$_2$)$_n$—, reaction of a compound of formula XII,

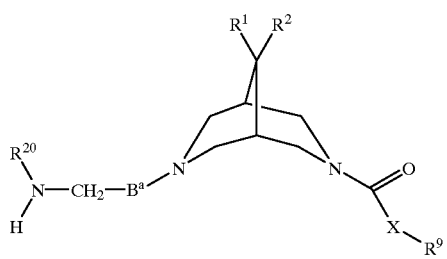

XII wherein $B^a$ represents C$_{1-6}$ alkylene and $R^1$, $R^2$, $R^9$, $R^{20}$ and X are as hereinbefore defined with a compound of formula XIII,

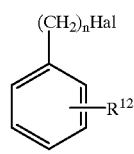

XIII wherein $R^{12}$, n and Hal are as hereinbefore defined, for example at 40° C. in the presence of a suitable organic solvent (e.g. acetonitrile);

(j) reaction of a compound of formula II, as hereinbefore defined, with a compound of formula XIV, $R^9$XH  XIV wherein $R^9$ and X are as hereinbefore defined, in the presence of 1,1'-carbonyldiimidazole, for example by refluxing in the presence of a suitable organic solvent (e.g. THF); or (k) conversion of one $R^{12}$ substituent to another using techniques well known to those skilled in the art.

Compounds of formula II may be prepared by reaction of a compound of formula XV,

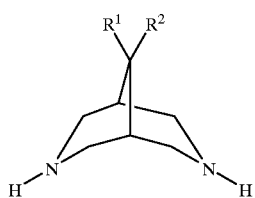

XV wherein $R^1$ and $R^2$ are as hereinbefore defined, with a compound of formula VI as hereinbefore defined, for example as described hereinbefore for synthesis of compounds of formula I (process step (c)), or, in the case of compounds of formula II wherein B represents CH$_2$ and $R^{10}$ represents OH, with a compound of formula V as hereinbefore defined, for example as described hereinbefore for synthesis of compounds of formula I (process step (b)).

Compounds of formula II in which $R^1$ and $R^2$ both represent H may be prepared by reduction of a compound of formula XVI,

XVI

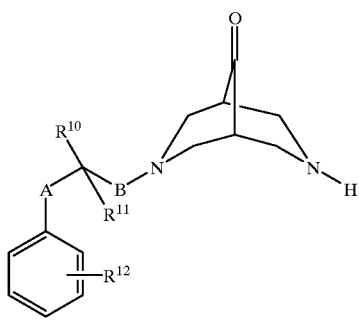

wherein $R^{10}$, $R^{11}$, $R^{12}$, A and B are as hereinbefore defined, and in which the C=O group may be activated using an appropriate agent, such as tosylhydrazine, for example as described hereinbefore for synthesis of compounds of formula I (process step (e)).

Compounds of formula IV may be prepared by reaction of a compound of formula XV, as hereinbefore defined, with a compound of formula III as hereinbefore defined, for example as described hereinbefore for synthesis of compounds of formula I (process step (a)).

Compounds of formula IV may alternatively be prepared by reaction of a compound of formula XV, as hereinbefore defined, with a compound of formula XIV, as hereinbefore defined, in the presence of 1,1'-carbonyldiimidazole, for example as described hereinbefore for synthesis of compounds of formula I (process step j)).

Compounds of formula IV in which $R^1$ and $R^2$ represent H may alternatively be prepared by reduction of a corresponding compound of formula XVIII,

XVIII

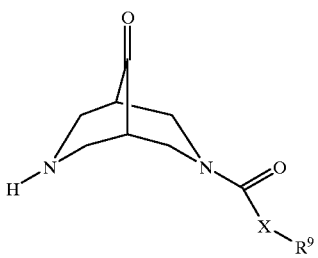

wherein $R^9$ and X are as hereinbefore defined, and in which the C=O group may be activated using an appropriate agent, such as tosylhydrazine, for example as described hereinbefore for compounds of formula I (process step Compounds of formula V may be prepared in accordance with techniques which are well known to those skilled in the art. For example, compounds of formula V in which:

(1) A represents —CH$_2$O— may be prepared by reaction of a compound of formula XIX,

XIX

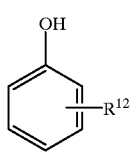

wherein $R^{12}$ is as hereinbefore defmed, with a compound of formula XX,

XX

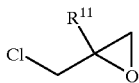

wherein $R^{11}$ is as hereinbefore defined, for example at elevated temperature (between 60° C. and reflux temperature) in the presence of a suitable base (e.g. K$_2$CO$_3$ or NaOH) and an appropriate organic solvent (e.g. acetonitrile or toluene water), or as otherwise described in the prior art;

(2) A represents —CH$_2$O— may be prepared by reaction of a compound of formula XIX, as hereinbefore defined, with a compound of formula XXI

XXI

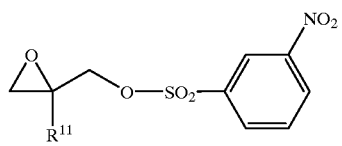

wherein $R^{11}$ is as hereinbefore defined, for example between room temperature and elevated temperature (e.g. 40° C.) in the presence of a suitable base (e.g. K$_2$CO$_3$ or potassium ethoxide) and an appropriate organic solvent (e.g. acetonitrile or DMF);

(3) A represents a single bond and $R^{11}$ represents H may be prepared by reduction of a compound of formula XXII,

XXII

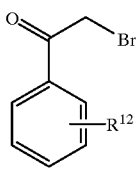

wherein $R^{12}$ is as hereinbefore defined, for example at between −15° C. and room temperature in the presence of a suitable reducing agent (NaBH$_4$) and an appropriate organic solvent (e.g. THF), followed by elimination of the resultant intermediate, for example at room temperature in the presence of a suitable base (e.g. K$_2$CO$_3$) and an appropriate organic solvent (e.g. acetonitrile); or (4) A represents C$_{1-4}$ alkylene, —(CH$_2$)$_n$N(R$^{20}$)—, —(CH$_2$)$_n$S(O)$_2$— or —(CH$_2$)$_n$O— (in which latter three groups n represents 1, 2, 3 or 4) or —(CH$_2$)$_m$C(H)(OH)(CH$_2$)$_n$— may be prepared by oxidation of a compound of formula XXIII,

XXIII

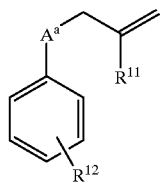

in which $A^a$ represents a single bond, $C_{1-3}$ alkylene, —$(CH_2)_{n-1}N(R^{20})$—, —$(CH_2)_{n-1}S(O)_2$— or —$(CH_2)_{n-1}O$— (in which latter three groups n represents 1, 2, 3 or 4) or —$(CH_2)_{m-1}C(H)(OH)(CH_2)_n$— (in which latter group n is as hereinbefore difined) and $R^{20}$ and m are as hereinbefore defined, in the presence of a suitable oxidising agent (e.g. mCPBA), for example by refluxing in the presence of a suitable organic solvent (e.g. DCM).

Compounds of formula VI may be prepared by standard techniques. For example compounds of formula VI in which:

(1) A represents —$(CH_2)_nO$— may be prepared by coupling a compound of formula XIX, as hereinbefore defined, to a compound of formula XXIV,

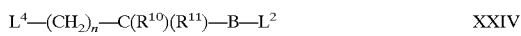

XXIV wherein $L^4$ represents a suitable leaving group (e.g. Hal) and Hal, n, $R^{10}$, $R^{11}$, B and $L^2$ are as hereinbefore defined; p1 (2) A represents —$C(O)N(R^{20})$— may be prepared by coupling a compound of formula XXV,

XXV wherein $R^{12}$ and $R^{20}$ are as hereinbefore defined, to a compound of formula XXVI,

XXVI wherein $L^4$, $R^{10}$, $R^{11}$, B and $L^2$ are as hereinbefore difined; or (3) $R^{10}$ represents —OH and $R^{11}$ represents methyl substituted by hydroxy, oxidation of a compound of formula XXVIA,

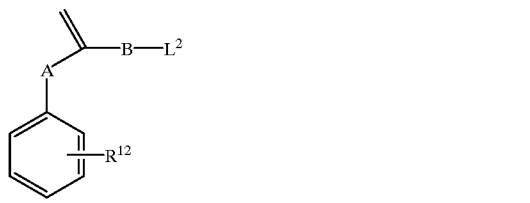

XXVIA wherein $R^{12}$, A, B and $L^2$ are as hereinbefore defined, in all three cases, under conditions which are well known to those skilled in the art (e.g. as described hereinafter).

Compounds of formula V and VI in which A represents —$(CH_2)_nS(O)$— or —$(CH_2)_nS(O)_2$— may be prepared by oxidation of a corresponding compound of formula I wherein A represents —$(CH_2)_nS$—, wherein n is as hereinbefore defined, in the presence of an appropriate amount of a suitable oxidising agent (e.g. mCPBA) and an appropriate organic solvent.

Compounds of formula VIII may be prepared in a similar fashion to compounds of formula I (see, for example, process steps (a) or (c)).

Alternatively, compounds of formula VIII in which B represents $C_2$ alkylene may be prepared by reaction of a compound of formula IV, as hereinbefore defined with a compound of formula XXVII,

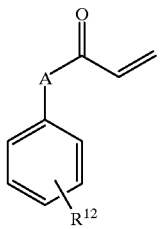

XXVII wherein A and $R^{12}$ are as hereinbefore defined, for example a room temperature in the presence of a suitable organic solvent (e.g. ethanol).

Compounds of formula XII may be prepared by removing an optionally substituted benzyloxycarbonyl unit from a corresponding compound of formula I in which $R^{10}$ and $R^{11}$ both represent H and A represents —$N(R^{20})C(O)O(CH_2)$—, B represents $B^a$ and $B^a$ is as hereinbefore defined under conditions which are well known to those skilled in the art.

Compounds of formula XV are known in the literature or are readily available using known techniques. For example, compounds of formula XV in which $R^1$ and $R^2$, together with the carbon atom to which they are attached, represent —O—$(CH_2)_2$—O—, —$(CH_2)_4$— or —$(CH_2)_5$—, may be prepared by reduction of a compound of formula XXVIII,

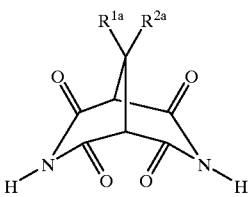

XXVIII wherein $R^{1a}$ and $R^{2a}$, together with the carbon atom to which they are attached, represent —O—$(CH_2)_2$—O—, —$(CH_2)_4$— or —$(CH_2)_5$—, in the presence of a suitable reducing agent (e.g. $LiAlH_4$) under conditions which are well known to those skilled in the art.

Compounds of formula IX may be prepared in analogous fashion to compounds of formula I. For example compounds of formula IX may be prepared by reaction of a compound of formula XVI, as hereinbefore defined, and a compound of formula III, as hereinbefore defined, for example as described hereinbefore for synthesis of compounds of formula I (process step (a)).

Compounds of formulae IX, XVI and XVIII, may be prepared, advantageously, by reaction of (as appropriate) either (i) a compound of formula XXIX,

XXIX

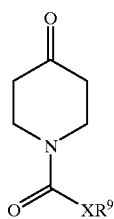

wherein $R^9$ and X are as hereinbefore defined, or (ii) 4-piperidone (or a protected derivative thereof), with (as appropriate) either (1) a compound of formula XXXI,

XXXI

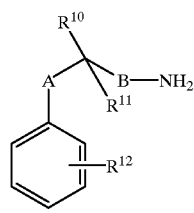

wherein $R^{10}$, $R^{11}$, $R^{12}$, A and B are as hereinbefore defined, or (2) $NH_3$ (or a protected (e.g. benzyl) derivative thereof), in all cases in the presence of a formaldehyde (i.e. an appropriate source of formaldehyde, such as paraformaldehyde or formalin solution). The formation of compounds of formulae IX, XVI and XVIII may be carried out in this way for example at between room temperature and reflux (depending upon the concentration of the reactants) in the presence of an appropriate solvent (e.g. ethanol or methanol) and, preferably, in the presence of an organic acid (e.g. a $C_{1-6}$ carboxylic acid, especially acetic acid). We have advantageously found that this process may be used to prepare bispidine derivatives incorporating a carbamate group ($—NC(O)XR^9$, where N is one of the bispidine nitrogens) directly from readily available starting materials, thus avoiding the need for long-winded, multi-step, syntheses, involving the coupling of a $—C(O)XR^9$ group to a bispidine unit, following formation of the latter (as well as avoiding any further protection/deprotection steps which are necessary). It will be also appreciated by those skilled in the art that compounds of formula XV in which $R^1$ and $R^2$ both represent H may also be prepared via this method (i.e. by reaction of a compound of 4-piperidone (or a protected derivative thereof) with $NH_3$ (or a protected derivative thereof) in the presence of a formaldehyde), provided that the intermediate so formed is subsequently reduced under appropriate reaction conditions.

Compounds of formula XXVIII may be prepared in accordance with techniques which are well known to those skilled in the art. For example compounds of formula XXVIII in which $R^{1a}$ and $R^{2a}$ together represent $—(CH_2)_4—$ or $—(CH_2)_5—$ may be prepared by reaction of a compound of formula XXXII,

XXXII

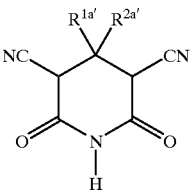

wherein $R^{1a'}$ and $R^{2a'}$ together represent $—(CH_2)_4—$ or $—(CH_2)_5—$, with a mixture with a mixture of phosphoric acid and sulfuric acid, for example at 120° C.

Compounds of formula XXXI are well known in the literature or are readily available using known techniques. For example, compounds of formula XXXI wherein $R^{10}$ represents OH, $R^{11}$ represents H and B represents $CH_2$ may be prepared by reaction of a compound of formula V in which $R^{11}$ represents H with ammonium hydroxide under conditions which are well known to those skilled in the art.

Compounds of formulae III, XI, XIII, XIV, XIX, XX, XXI, XXII, XXIII, XXIV, XXV, XXVI, XXVIA, XXVII, XXIX and XXXII, and derivatives thereof, are either commercially available, are known in the literature, or may be obtained either by analogy with the processes described herein, or by conventional synthetic procedures, in accordance with standard techniques, from readily available starting materials using appropriate reagents and reaction conditions.

Substituents on the aryl (e.g. phenyl), and (if appropriate) heterocyclic, group(s) in compounds of formulae I, II, III, IV, V, VI, VIII, IX, XII, XIII, XIV, XVI, XVIII, XIX, XXII, XXIII, XXV, XXVIA, XXVII, XXIX and XXXI may be converted to other claimed substituents using techniques well known to those skilled in the art. For example, nitrobenzene may be reduced to an aminobenzene, hydroxy may be converted to alkoxy, alkoxy may be hydrolysed to hydroxy etc.

The compounds of the invention may be isolated from their reaction mixtures using conventional techniques.

It will be appreciated by those skilled in the art that, in the process described above, the functional groups of intermediate compounds may be, or may need to be, protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyloxy groups (e.g. methyl- and ethylcarbonyloxy groups). Suitable protecting groups for amino include benzyl, tert-butyloxycarbonyl, 9-fluorenylmethoxycarbonyl or benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art and as described hereinafter.

Many protected derivatives of the intermediate compounds described hereinbefore are commercially available.

The use of protecting groups is fully described in "Protective Groups in Organic Chemistry", edited by J W F McOmie, Plenum Press (1973), and "Protective Groups in Organic Synthesis", 2nd edition, T W Greene & P G M Wutz, Wiley-Interscience (1991).

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

It will also be appreciated by those skilled in the art that, although certain protected derivatives of compounds of formula I, which may be made prior to a final deprotection stage, may not possess pharmacological activity as such, they may be administered parenterally or orally and thereafter metabolised in the body to form compounds of the invention which are pharmacologically active. Such derivatives may therefore be described as "prodrugs". Moreover, we have found that certain compounds of formula I may act as prodrugs of other compounds of formula I.

All prodrugs of compounds of formula I are included within the scope of the invention.

Some of the intermediates referred to hereinbefore are novel. According to a further aspect of the invention there is thus provided: (a) a novel compound of formula IV as hereinbefore defined or a protected derivative thereof; (b) a novel compound of formula IX as hereinbefore defined or a protected derivative thereof; (c) a novel compound of formula XVI as hereinbefore defined or a protected derivative thereof; and (d) a novel compound of formula XVIII as hereinbefore defined or a protected derivative thereof.

Medical and Pharmaceutical Use

The compounds of the invention are useful because they possess pharmacological activity. They are therefore indicated as pharmaceuticals.

Thus, according to a further aspect of the invention there is provided the compounds of the invention for use as pharmaceuticals.

In particular, the compounds of the invention exhibit myocardial electrophysiological activity, for example as demonstrated in the test described below.

The compounds of the invention are thus expected to be useful in both the prophylaxis and the treatment of arrhythmias, and in particular atrial and ventricular arrhythmias.

The compounds of the invention are thus indicated in the treatment or prophylaxis of cardiac diseases, or in indications related to cardiac diseases, in which arrhythmias are believed to play a major role, including ischaemic heart disease, sudden heart attack, myocardial infarction, heart failure, cardiac surgery and thromboembolic events.

In the treatment of arrhythmias, compounds of the invention have been found to selectively delay cardiac repolarization, thus prolonging the QT interval, and, in particular, to exhibit class III activity. Although compounds of the invention have been found to exhibit class III activity in particular, in the treatment of arrhythmias, their mode(s) of activity is/are not necessarily restricted to this class.

Compounds of the invention have also been found to be potent, yet possess a duration of action which is relatively short (e.g. 1 to 120, preferably 1 to 60, more preferably 1 to 30 and particularly 1 to 15 minutes, as measured in the test described below) when compared to compounds known in the prior art. Compounds of the invention are therefore expected to possess the advantages hereinbefore mentioned for short acting compounds.

According to a further aspect of the invention, there is provided a method of treatment of an arrhythmia which method comprises administration of a therapeutically effective amount of a compound of the invention to a person suffering from, or susceptible to, such a condition.

Pharmaceutical Preparations

The compounds of the invention will normally be administered subcutaneously, intravenously, intraarterially, transdermally, intranasally, by inhalation, or by any other parenteral route, in the form of pharmaceutical preparations comprising the active ingredient either as a free base, a pharmaceutical acceptable ion exchanger or a non-toxic organic or inorganic acid addition salt, in a pharmaceutically acceptable dosage form. Depending upon the disorder and patient to be treated, as well as the route of administration, the compositions may be administered at varying doses.

The compounds of the invention may also be combined with any other drugs useful in the treatment of arrhythmias and/or other cardiovascular disorders.

According to a further aspect of the invention there is thus provided a pharmaceutical formulation including a compound of the invention in admixture with a pharmaceutically acceptable adjuvant, diluent or carrier.

Suitable daily doses of the compounds of the invention in therapeutic treatment of humans are about 0.05 to 5.0 mg/kg body weight at parenteral administration.

The compounds of the invention have the advantage that they are effective against cardiac arrhythmias.

Compounds of the invention have also been found to possess a shorter duration of action than compounds known in the prior art and are therefore expected to be particularly useful when used in the acute conversion of arrhythmias as mentioned hereinbefore.

Compounds of the invention may also have the advantage that they may be more efficacious than, be less toxic than, have a broader range of activity (including exhibiting any combination of class I, class II, class III and/or class IV activity (especially class I, class II and/or class IV activity in addition to class III activity)) than, be more potent than, produce fewer side effects (including a lower incidence of proarrhythmias such as torsades de pointes) than, be more easily absorbed than, or that they may have other useful pharmacological properties over, compounds known in the prior art.

Biological Tests

Test A

Primary Electrophysiological Effects In Anaesthetised Guinea Pigs

Guinea pigs weighing between 660 an 1100 g were used. The animals were housed for at least one week before the experiment and had free access to food and tap water during that period.

Anaesthesia was induced by an intraperitoneal injection of pentobarbital (40 to 50 mg/kg) and catheters were introduced into one carotid artery (for blood pressure recording and blood sampling) and into one jugular vein (for drug infusions). Needle electrodes were placed on the limbs for recording of ECGs (lead II). A thermistor was placed in the rectum and the animal was placed on a heating pad, set to a rectal temperature of between 37.5 and 38.5° C.

A tracheotomy was performed and the animal was artificially ventilated with room air by use of a small animal ventilator, set to keep blood gases within the normal range for the species. In order to reduce autonomic influences both vagi were cut in the neck, and 0.5 mg/kg of propranolol was given intravenously, 15 minutes before the start of the experiment.

The left ventricular epicardium was exposed by a left-sided thoracotomy, and a custom-designed suction electrode for recording of the monophasic action potential (MAP) was applied to the left ventricular free wall. The electrode was kept in position as long as an acceptable signal could be recorded, otherwise it was moved to a new position. A bipolar electrode for pacing was clipped to the left atrium. Pacing (2 ms duration, twice the diastolic threshold) was performed with a custom-made constant current stimulator. The heart was paced at a frequency just above the normal sinus rate during 1 minute every fifth minute throughout the study.

The blood pressure, the MAP signal and the lead II ECG were recorded on a Mingograph ink-jet recorder (Siemens-Elema, Sweden). All signals were collected (sampling frequency 1000 Hz) on a PC during the last 10 seconds of each pacing sequence and the last 10 seconds of the following minute of sinus rhythm. The signals were processed using a custom-made program developed for acquisition and analysis of physiological signals measured in experimental animals (see Axenborg and Hirsch, Comput. Methods Programs Biomed. 41, 55 (1993)).

The test procedure consisted of taking two basal control recordings, 5 minutes apart, during both pacing and sinus rhythm. After the second control recording, the first dose of the test substance was infused in a volume of 0.2 mL into the jugular vein catheter for 30 seconds. Three minutes later, pacin g was started and a new recording was made. Five minutes after the previous dose, the next dose of test substance was administered. Six to ten consecutive doses were given during each experiment.

Data Analysis

Of the numerous variables measured in this analysis, three were s elected as the most important for comparison and selection of active compounds. The three variables selected were the MAP duration at 75 percent repolarization during pacing, the atrio-ventricular (AV) conduction time (difined as the interval between the atrial pace pulse and the start of the ventricular MAP) during pacing, and the heart rate (defined as the RR interval during sinus rhythm). Systolic and diastolic blood pressure were measured in order to judge the haemodynamic status of the anaesthetised animal. Further, the ECG was checked for arrhythmias and/or morphological changes.

The mean of the two control recordings was set to zero and t he effects recorded after consecutive doses of test substance were expressed as percentage changes from this value. By plotting these percentage values against the cumulative dose administered before each recording, it was possible to construct dose-response curves. In this way, each experiment generated three dose-response curves, one for MAP duration, one for AV-conduction time and one for the sinus fr equency (RR interval). A mean curve of all experiments performed with a test substance was calculated, and potency values were derived from the me an curve. All dose-response curves in these experiments were cons tructed by linear connection of the data points obtained. The cumulative dose prolonging the MAP duration by 10% from the baseline was used as an index to assess the class III electrophysiological potency of the agent under investigation ($D_{10}$).

Test B

Metabolic Stability of Test Compounds

An in vitro screen was set up to determine the metabolic stability of the compounds of the invention.

The hepatic S-9 fraction from dog, man, rabbit and rat with NADPH as co-factor was used. The assay conditi ons were as follows: S-9 (3 mg/mL), NADPH (0.83 mM), Tris-HCl buffer (50 mM) at pH 7.4 and 10 $\mu$M of test compound.

The reaction was started by addition of test compound and terminated after 0, 1, 5, 15 and 30 minutes by raising the pH in the sample to above 10 (NaOH; 1 mM). After solvent extraction, the concentration of test compound was measured against an internal standard by LC (fluorescence/UV detection).

The percentage of test compound remaining after 30 minutes (and thus $t_{1/2}$) were calculated and used as a measure for metabolic stability.

The invention is illustrated by way of the following examples.

EXAMPLES

General Experimental Procedures

Mass spectra were recorded on a Finnigan MAT TSQ 700 triple quadrupole mass spectrometer equipped with an electrospray interface (FAB-MS) and VG Platform II mass spectrometer equipped with an electrospray interface (LC-MS), a Hewlett Packard model 6890 gas chromatograph connected to a Hewlett-Packard model 5973A mass spectrometer via a Hewlett Packard HP-5-MS GC column, or a Shimadzu QP-5000 GC/mass spectrometer (CI, methane). $^1$H NMR and $^{13}$C NMR measurements were performed on a BRUKER ACP 300 and Varian UNITY plus 400 and 500 spectrometers, operating at $^1$H frequencies of 300, 400 and 500 MHz respectively, and at $^{13}$C frequencies of 75.5, 100.6 and 125.7 MHz respectively. Alternatively, $^{13}$C NMR measurements were performed on a BRUKER ACE 200 spectrometer at a frequency of 50.3 MHz.

Rotamers may or may not be denoted in spectra depending upon ease of interpretation of spectra. Unless otherwise stated, chemical shifts are given in ppm with the solvent as internal standard.

Synthesis of Intermediates

Example A 4-(2-Oxiranylmethoxy)benzonitrile

Epichlorohydrin (800 mL) and $K_2CO_3$ (414 g) were added to a stirred solution of p-cyanophenol (238 g) in 2.0 L MeCN and the reaction mixture was refluxed under inert atmosphere for 2 h. The hot solution was filtered and the filtrate concentrated giving a clear oil which was crystallized from di-iso-propyl ether giving the product in 75% yield.

$^{13}$C NMR (CDCl$_3$): δ 44.4, 49.7, 69.0, 104.5, 115.3, 118.9, 134.0, 161.6.

Example B

2-{[(3-Nitrophenyl)sulfonyloxy]methyl}oxirane m-Nitrobenzensulfonylchloride (12.6 g; 57 mmol) was added to a cold (−20° C.) solution of (R)-(+)-glycidol (5.5 g;

74 mmol) and TEA (10.3 mL; 74 mmol). The reaction mixture was stirred at −20° C. for 96 h. The solution was filtered and the filtrate washed with tartaric acid (10% w/w), brine, H$_2$O and concentrated giving the title compound in a 97% yield.

$^1$H NMR (CDCl$_3$): δ 2.62 (dd,1H), 2.84 (dd,1H), 3.22 (m,1H), 4.07 (dd,1H), 4.49 (dd,1H), 7.80 (t,1H), 8.25 (m,1H), 8.52 (m,1H), 8.78 (m,1H).

Example C

4-[(2S)-Oxiranylmethoxy]benzonitrile

The title compound was prepared in a 90% yield according to the procedure described in Example A above starting from (R)-(−)-epichlorohydrin.

Example D

4-[(2R)-Oxiranylmethoxy]benzonitrile

The title compound was prepared according to the procedure described in Example A above starting from (S)-(−)-epichlorohydrin.

[α]$_D^{20}$=−14.1° (c=1.0; acetone);

$^1$H NMR (CDCl$_3$): δ 2.79 (1H, m); 2.98 (1H, m); 3.39 (1H, m); 3.98 (1H, m); 4.37 (1H, m); 6.99 (2H, d); 7.60 (2H, d).

Example E

3-Benzyl-3,7-diazabicyclo[3.3.1]nonane
(a) 3,7-Dibenzyl-3,7-diazabicyclo[3.3.1]nonane The sub-title compound was prepared according to the method described in J. Org. Chem. 41, 1593, (1976) except that 3,7-dibenzyl-3,7-diazabicyclo[3.3.1]nonan-9-one (also prepared according to the method described in J. Org. Chem. 41, 1593 (1976)) was used instead of N-benzyl-N-methylbispidone.

(b) 3-Benzyl-3,7-diazazbicyclo[3.3.1]nonane 3,7-Dibenzyl-3,7-diazabicyclo[3.3.1]nonane (1.97 g; 6.4 mmol; from step (a) above) was dissolved in EtOH (95%) and hydrogenated over 5% Pd/C at 1 atm. until tlc indicated that the reaction was complete. The catalyst was removed by filtration through a pad of celite and the residue was concentrated under reduced pressure to give the title compound in a quantitative yield.

$^{13}$C NMR (CDCl$_3$): δ 30.1, 33.4, 36.0, 52.5, 59.6, 64.3, 126.9, 128.3, 128.7, 138.8.

Example F tert-Butyl 3,7-diazabicyclo[3.3.1]nonane-3-carboxylate (a) tert-Butyl 7-benzyl-9-oxy-3,7-diazabicyclo[3.3.1] nonane-3-carboxylate Paraformaldehyde (4.00 g; 127 mmol) was added to a solution of benzylamine (13.7 g; 126 mmol) in ethanol (190 mL). The solution was heated to 60° C. and a solution of acetic acid (15.2 g; 252 mmol) in ethanol (160 mL) was added over 2 hours. After additional stirring for 1 hour, the solution was cooled to room temperature. This solution was added (over 2 hours) to a mixture of 1-tert-butoxycarbonyl-4-piperidone (25.5 g; 127 mmol) and paraformaldehyde (4.80 g; 152 mmol) in ethanol (270 mL) which had been heated to 60° C. After reflux overnight, the solution was cooled to room temperature. The ethanol was removed by evaporation. Extractive work-up was performed in toluene:water and the material was filtered through silica in a toluene:ethyl acetate system. Evaporation of the eluate gave a solid material (37.4 g). The purity was 90 area % (HPLC) and the was yield 60%. By performing a crystallisation in iso-propanol, a compound with a purity of 98 area % (HPLC) and a yield of 70% was obtained.

MS (EI; 70 eV): m/z 91 (100%), m/z 57 (42%), m/z 273 (32%), m/z 330 (5%).

$^{13}$C NMR (CDCl$_3$): δ 28.72, 47.71, 49.91, 50.60, 58.83, 59.16, 61.96, 80.18, 127.37, 128.45, 128.89. 137.57, 154.89, 213.66 ppm using TMS as reference.

(b) tert-Butyl 7-benzyl-9-oxy-3,7-diazabicyclo[3.3.1]nonane-3-carboxylate (alternative preparation)

Benzylamine (6.51 g; 60.2 mmol), acetic acid (72.3 g, 1200 mmol), paraformaldehyde (3.71 g; 120 mmol) and 1-tert-butoxycarbonyl-4-piperidone (12.0 g; 60.2 mmol), were added to ethanol (300 mL). The solution was heated to 65° C. and stirred at this temperature for 2 hours. The same work-up procedure as that described in step (a) above was performed, yielding 15.78 g of material with a purity of 92 area % (HPLC) and a yield of 70%. Recrystallisation from iso-propanol yielded a compound with a purity of 94 area % (HPLC) in a yield of 54%.

(c) tert-Butyl 7-benzyl-3,7-diazabicyclo[3.3. 1]-nonane-3-carboxylate

A mixture of 4-toluenesulfonehydrazide (12.4 mmol; 2.30 g) and tert-butyl 7-benzyl-9-oxy-3,7-diazabicyclo[3.3.1] nonane-3-carboxylate (10.1 mmol; 4.00 g; 83.3%; from step (a) above) were dissolved in isopropanol (30 mL) and heated at reflux for 2 hours. Acetic acid (2.5 mmol; 0.15 g) and sodium cyanoborohydride (12.1 mmol, 0.76 g) were added and the mixture was again heated at reflux for 2 hours. The slurry was cooled to ambient temperature and filtered. The filtrate was concentrated and an extractive work-up was performed in toluene:water. The toluene solution was concentrated to give 0.95 g of sub-title compound, with a purity of 90 area % (GC) in a yield of 60%.

MS (EI; 70 eV): m/z 259 (100%), m/z 91 (95%), m/z 169 (45%), m/z 57 (35%), m/z 316 (25%).

$^{13}$C NMR (CDCl$_3$): δ 28.67, 28.95, 31.11, 47.55, 48.38, 58.70, 58.96, 63.46, 78.71, 126.57, 128.00, 128.53, 138.94, 155.20 ppm using TMS as a reference.

(d) tert-Butyl 3,7-diazabicyclo[3.3.1]nonane-3-carboxylate tert-Butyl 7-benzyl-3,7-diazabicyclo[3.3.1]nonane-3-carboxylate (from step (c) above) was debenzylated according to the method described in Example E(b) above to give the title compound in quantitative yield.

$^{13}$C NMR (CDCl$_3$): δ 28.05, 28.29, 31.33, 48.35, 49.11, 51.53, 79.34, 155.16.

Example G

4-[3-(3,7-Diazabicyclo[3.3.1 ]non-3-yl)-2-hydroxypropoxy]benzonitrile

HCl-saturated EtOAc (600 mL) was added to a solution of tert-butyl 7-[3-(4-cyanophenoxy)-2-hydroxypropyl]-3,7-diazabicyclo[3.3.1]nonane-3-carboxylate (62 g; see Example 2 below) in EtOAc (600 mL) and the mixture was stirred at rt. for 4 h. The solvent was removed under reduced pressure, the residue was dissolved in MeCN (1.3 L) and K$_2$CO$_3$ (100 g) was added. The suspension was stirred for 12 h and filtered. Concentration of the filtrate gave the title compound in a 90% yield.

$^{13}$C NMR (CDCl$_3$): δ 28.9, 29.2, 32.3, 50.9, 57.7, 60.8, 62.1, 66.0, 71.2, 104.0, 115.3, 119.1, 133.9, 162.1.

(The title compound was also readily converted to the hydrochloride salt (also used as an intermediate in the examples below) using standard techniques.)

Example H iso-Propyl 3,7-diazabicyclo[3.3.1]nonane-3-carboxylate (a) iso-Propyl 7-benzyl-3,7-diazabicyclo[3.3.1]nonane-3-carboxylate NaOH (6.0 mL; 10M), H$_2$O (10 mL) and iso-propylchloroformate (55 mmol) were added to a solution of 3-benzyl-3,7-diazabicyclo[3.3.1]nonane (10.8 g; 50 mmol; see Example E above)-in DCM (50 mL) The reaction mixture was stirred for 3 h and the phases were then separated. The organic phase -was washed with H$_2$O and brine, dried and concentrated to give the sub-title compound in a 95% yield.

(b) iso-Propyl 3,7-diazabicyclo[3.3.1]nonane-3-carboxylate

The title compound was prepared according to the method described in Example E(b) above from iso-propyl 7-benzyl-3,7-diazabicyclo-[3.3.1 ]nonane-3-carboxylate (from step (a) above).

FAB-MS (M+1)$^+$213 (m/z); $^{13}$C NMR (CD$_3$CN): δ 22.53, 29.34, 32.23, 49.46, 52.40, 68.67, 156.24.

Example I tert-Butyl 9-oxy-3,7-diazabicyclo[3.3.1]-nonan-3-carboxylate tert-Butyl 7-benzyl-9-oxy-3,7-diazabicyclo[3.3.1]-nonan-3-carboxylate (1.2 g; 3.17 mmol) and palladium on charcoal paste (0.10 g; 5% Pd/C; 63% water) were added to ethanol (20 mL). The hydrogenolysis was performed by applying a pressure of 4 bars of hydrogen. After the reaction was completed, the suspension was filtered, concentrated and purified with flash chromatography, yielding 0.20 g of material with a purity of 93 area % (GC).

MS (EI; 70 eV): m/z 57 (100%), m/z 96 (80%), m/z 41 (40%), m/z 140 (35%), m/z 110 (30%), m/z 183 (30%), m/z 240 (15%); $^{13}$C NMR (CDCl$_3$): δ 28.52, 49.36, 50.48, 55.48, 80.96, 154.87, 213.41 ppm using TMS as a reference.

Example J

Ethyl 7-[3-(4-cyanophenoxy)-2-hydroxypropyl]-9-oxy-3,7-diazabicyclo-[3.3.1 ]nonane-3-carboxylate (a) 3-(4-Cyanophenoxy)-2-hydroxypropylamine IPA (300 mL) was added to a stirred suspension of 4-(2-oxiranylmethoxy)benzonitrile (100 g; 571 mmol; see Example A above) in NH$_3$ (500 mL; conc.), and the reaction mixture was stirred at rt. for 3 days. The precipitate was filtered off and the residue concentrated and recrystallized from MeCN to give the sub-title compound in a 46% yield.

(b) Ethyl 7-[3-(4-cyanophenoxy)-2-hydroxypropyl]-9-oxy-3,7-diazabicyclo[3.3.1]nonane-3-carboxylate A solution of AcOH (0.30 g; 5.0 mmol) in MeOH (5 mL), followed by paraformaldehyde (0.33 g; 11.0 mmol), were added to a stirred suspension of 3-(4-cyanophenoxy)-2-hydroxypropylamine (0.96 g; 5.0 mmol; from step (a) above) in MeOH (5 mL) under inert atmosphere (N$_2$). The temperature was raised to 55° C. and a solution of 1-ethoxycarbonyl-4-piperidone (0.86 g; 5.0 mmol) in MeOH (5 mL) was added and the reaction mixture stirred for 6 h. The solids were filtered off and the solution was concentrated. The solid residue was partitioned between water and diethyl ether. The aqueous phase was collected and the pH adjusted to 10 (4M NaOH) and extracted with DCM. The combined organic layers were concentrated and purified using column chromatography (DCM:MeOH; 19:1) to give the sub-title compound in a 30% yield.

$^{13}$C NMR (CDCl$_3$): δ 14.5, 48.0, 50.6, 57.3, 61.2, 62.2, 65.4, 70.3, 104.2, 115.3, 119.0, 133.9, 157.9, 161.9, 211.7.

Preparation of Compounds of Formula I

Example 1

Ethyl 7-[3-(4-cyanophenoxy)-2-hydroxypropyl]-3,7-diazabicyclo[3.3.1]-nonane-3-carboxylate Ethylchloroformate (930 mg; 8.4 mmol) was added to a stirred solution of 4-[3-(3,7-diazabicyclo[3.3.1]non-3-yl)-2-hydroxypropoxy]benzonitrile (2.3 g; 7.6 mmol; see Example G above) and NaOH (1.5 mL; 10 M) in DCM (60 mL). The solution was stirred at rt. for 1 h, washed with water and the organic layer was separated, dried (Na$_2$SO$_4$) and concentrated. Purification using column chromatography (DCM:MeOH; 19:1) gave the title compound (1.4 g).

$^{13}$C NMR (CDCl$_3$): δ 14.7, 29.2, 32.7, 48.6, 56.7, 60.2, 61.3, 62.6, 65.0, 70.8, 104.0, 115.4, 129.8, 133.9, 157.6, 162.2.

Example 2 tert-Butyl 7-[3-(4-cyanophenoxy)-2-hydroxypropyl[-3,7-diazabicyclo-[3.3.1]nonane-3-carboxylate A mixture of tert-butyl 3,7-diazabicyclo[3.3.1]nonane-3-carboxylate (2.3 g; 10 mmol; see Example F above) and 4-(2-oxiranylmethoxy)benzonitrile (1.8 g; 10 mmol; see Example A above) in IPA (10 mL) and H$_2$O (1 mL) was stirred at 60° C. for 12 h. The reaction mixture was concentrated under reduced pressure and the residue dissolved in DCM and washed with brine, H$_2$O , dried and concentrated. Purification using column chromatography (DCM:MeOH; 19:1) gave the title compound in a 81% yield.

$^{13}$C NMR (CDCl$_3$): δ 28.44, 28.77, 29.33, 31.93,47.53, 49.34, 56.87, 60.14, 61.60, 65.03, 70.70, 79.37, 103.85, 115.32, 119.13, 133.79, 155.91, 162.16.

Example 3

3,7-Diazabicyclo[3.3.1]nonane-3-carboxylic acid, 7-[(2S)-3-(4-cyanophenoxy)-2-hydroxypropyl]-1,1-dimethylethyl ester 4-[(2S)-Oxiranylmethoxy]benzonitrile (5.19 g; 29.6 mmol; see Example C above) was added to a stirred solution of tert-butyl 3,7-diazabicyclo[3.3.1]nonane-3-carboxylate (6.7 g; 29.6 mmol; see Example F above) in IPA (30 mL) and H$_2$O (3 mL) The reaction mixture was stirred at 60° C. for 12 h and then at rt. for 48 h. The reaction mixture was concentrated, the residue dissolved in DCM, dried (MgSO$_4$) and concentrated. The residue was purified using column chromatography (hexane:EtOAc:MeOH; 50:45:5) to give the title product as a white foam in a 56% yield (6.65 g).

[α]$_{20}$$^D$=16 (c=1.0; MeOH). ESI-MS (M+1)$^+$402 (m/z); $^{13}$C NMR (CDCl$_3$): δ 28.44, 28.77, 29.33, 31.93, 47.53, 49.34, 56.87, 60.14, 61.60, 65.03, 70.70, 79.37, 103.85, 115.32, 119.13, 133.79, 155.91, 162.16.

Example 4 tert-Butyl 7-[(2R)-3-(4-cyanophenoxy)-2-hydroxypropyl]-3,7-diazabicyclo-[3.3.1]nonane-3-carboxylate The title compound was prepared analogously to the method described in Example 3 above from 4-[(2R)- oxiranylmethoxy]benzonitrile (0.98 g; 5.59 mmol; see Example D above) and tert-butyl 3,7-diazabicyclo[3.3.1]nonane-3-carboxylate (1.26 g; 5.59 mmol; see Example F above). After the reaction was complete, the residue was dissolved in DCM and washed with brine, separated, dried ($Na_2SO_4$) and concentrated. The residue was dissolved in MeOH (10 mL) and 1 eq. tartaric acid was added. Freeze-drying gave the product as the corresponding tartaric acid salt in 88% yield (2.7 g).

$^{13}C$ NMR ($CDCl_3$): δ 28.44, 28.77, 29.33, 31.93, 47.53, 49.34, 56.87, 60.14, 61.60, 65.03, 70.70, 79.37, 103.85, 115.32, 119.13, 133.79, 155.91, 162.16.

Example 5 iso-Propyl 7-[3-(4-cyanophenoxy)-2-hydroxypropyl]-3,7-diazabicyclo-[3.3.1]nonane-3-carboxylate Prepared according to the method described in Example 1 above, starting with iso-propylchloroformate.

ESI-MS $(M+1)^+388$ (m/z); $^{13}C$ NMR ($CDCl_3$): δ 22.38, 29.22, 29.49, 32.82, 48.49, 49.43, 56.46, 60.09, 62.47, 64.85, 68.38, 70.83, 103.96, 115.33, 119.26, 133.90, 157.32, 162.20.

Example 6 tert-Pentyl 7-[3-(4-cyanophenoxy)-2-hydroxypropyl]-3,7-diazabicyclo-[3.3.1]nonane-3-carboxylate (a) tert-Pentyl 7-benzyl-3,7-diazabicyclo[3.3.1]nonane-3-carboxylate Di-tert-pentyl dicarbonate (6.1 mL; 25 mmol) was added to a stirred solution of 3-benzyl-3,7-diazabicyclo[3.3.1]nonane (5.41 g; 25 mmol; see Example E above) in THF (50 mL). The reaction mixture was stirred 12 h at rt. and the solvent evaporated.

(b) tert-Pentyl 3,7-diazabicyclo[3.3.1]nonane-3-carboxylate tert-Pentyl 7-benzyl-3,7-diazabicyclo[3.3.1]nonane-3-carboxylate (8.67 g; from step (a) above) was dissolved in EtOH (45 mL) and hydrogenated over 5% Pd/C at 1 atm. for 10 h. The catalyst was removed by filtration and the residue was concentrated giving the sub-title compound.

(c) tert-Pentyl 7-[3-(4-cyanophenoxy)-2-hydroxypropyl]-3,7-diazabicyclo-[3.3.1]nonane-3-carboxylate tert-Pentyl 3,7-diazabicyclo[3.3.1]nonane-3-carboxylate (1.0 g; 4.16 mmol; from step (b) above) was dissolved in IPA:$H_2O$ (9:1; 4 mL) and 4-(2-oxiranylmethoxy)benzonitrile (1.46 g; 8.32 mmol; see Example A above) was added to the resultant solution. The reaction mixture was stirred at 60° C. for 3 h, concentrated and the residue subjected to column chromatography (DCM:MeOH; gradient 1:0 to 68:32) giving the title compound (1.45 g).

$^{13}C$ NMR ($CDCl_3$): δ 8.2, 25.8, 28.6, 31.8, 33.8, 47.4, 49.2, 56.6, 59.9, 61.3, 64.8, 70.6, 81.5, 103.6, 115.2, 119.0, 133.6, 155.7, 162.0.

Example 7

Isopropyl 7-[(2S)-3-(4-cyanophenoxy)-2-hydroxypropyl]-3,7-diazabicyclo-[3.3.1]nonane-3-carboxylate The title compound was prepared according to the method described in Example 3 above, using iso-propyl 3,7-diazabicyclo[3.3.1]nonane-3-carboxylate (see Example H above). The yield was 90%.

ESI-MS $(M+1)^+388$ (m/z); $^{13}C$ NMR ($CDCl_3$): δ 22.13, 22.20, 29.06, 29.31, 32.59, 48.30, 49.23, 56.34, 59.90, 62.24, 64.74, 6 8.14, 70.72, 103.74, 115.20, 119.02, 133.68, 157.07, 162.07.

Example 8 iso-Butyl 7-[3-(4-cyanophenoxy)-2-hydroxypropyl]-3,7-diazabicyclo-[3.3.1]nonane-3-carboxylate The title compound is prepared according to the method described in Example 47 below, using iso-butylchloroformate and 1.5 eq. of $K_2CO_3$ as base.

ESI-MS $(M+1)^+402$ (m/z); $^{13}C$ NMR ($CDCl_3$): δ 19.09, 19.22, 27.84, 29.17, 29.34, 32.69, 48.33, 49.35, 56.48, 60.05, 62.36, 64.90, 70.85, 71.55, 103.71, 115.34, 119.16, 133.79, 157.67, 162.19.

Example 9

Cyclopentyl 7-[3-(4-cyanophenoxy)-2-hydroxypropyl]-3,7-diazabicyclo-[3.3.1]nonane-3-carboxylate The title compound was prepared according to the method described in Example 1 above, using cyclopentylchloroformate.

FAB-MS $(M+1)^+414$ (m/z); $^{13}C$ NMR ($CD_3OD$; 55° C.): δ 23.56, 23.70, 29.18, 29.46, 32.70, 32.95, 33.42, 48.28, 49.50, 56.35, 60.09, 62.38, 64.94, 70.84, 77.86, 103.92, 115.32, 119.32, 133.65, 157.44, 162.21.

Example 10 tert-Butyl 7-{3-[(4-cyano-2-(cyclopropylcarbamoyl)phenoxy]-2-hydroxypropyl}-3,7-diazabicyclo[3.3.1]nonane-3-carboxylate (a) Methyl 5-bromo-2-hydroxybenzoate $Br_2$ (52 g) was slowly added to a stirred solution of methyl salicylate (50 g; 330 mmol) in 300 mL acetic acid. The reaction mixture was stirred at rt. for 10 h, poured on ice-water and the precipitate recrystallized from MeOH, giving the sub-title compound in a 83% yield.

(b) Methyl 5-cyano-2-hydroxybenzoate

Methyl 5-bromo-2-hydroxybenzoate (190.8 g; from step (a) above) and CuCN (73.9 g) were refluxed in DMF (500 mL) for 7 h. The temperature was allowed to decrease to 80° C. and HCl (500 mL) and $FeCl_3$ (165.0 g) were added. The reaction mixture was stirred for 30 min., concentrated and partitioned between $H_2O$ and DCM. The organic layer was dried, concentrated the residue recrystallized from methylethyl ketone giving the sub-title compound in a 61% yield.

(c) $N^1$-Cyclopropyl-5-cyano-2-hydroxybenzamide

Cyclopropyl amine (14.3 g) and Na (100 mg) were added to a solution of methyl 5-cyano-2-hydroxybenzoate (10.0 g; from step (b) above) in DMSO (40 mL). The reaction mixture was heated at 80° C. in a sealed steel vessel overnight, diluted with $H_{2O}$, acidified and extracted with EtOAc giving the sub-title compound (11.0 g), after concentration of the organic layer.

(d) $N^1$-Cyclopropyl-5-cyano-2(2-oxiranylmethoxy)benzamide

The sub-title compound was prepared according to the method described inExample A above from $N^1$-cyclopropyl-5-cyano-2-hydroxybenzamide (from step (c) above).

(e) tert-Butyl 7-{3-[(4-cyano-2-(cyclopropylcarbamoyl)phenoxy]-2-hydroxypropyl}-3,7-diazabicyclo[3.3.1]nonane-3-carboxylate The title compound was prepared according to the method described in Example 2 above from N$^1$-cyclopropyl-5-cyano-2(2-oxiranylmethoxy)-benzamide (from step (d) above).

$^{13}$C NMR (CDCl$_3$): δ 6.5, 23.0, 28.0, 31.5, 47.5, 49.0, 57.0, 61.5, 72.0, 79.5, 105.0, 113.0, 118.0, 123.0, 136.0, 156.5, 159.0, 164.0.

Example 11 tert-Butyl 7-{3-[(4-cyano-2-(iso-propylcarbamoyl) phenoxy]-2-hydroxpropyl}-3,7-diazabicyclo[3.3.1] nonane-3-carboxylate (a) N$^1$-iso-Propyl-5-cyano-2-hydroxybenzamide Methyl 5-cyano-2-hydroxybenzoate (8.85 g; 50 mmol; see Example 10(b) above) and NaCN (250 mg; 5 mmol) were dissolved in DMSO (10 mL) and MeOH (50 mL) and iso-propyl amine (25 mL) was added. The reaction mixture was heated (60° C.) in a sealed steel vessel for 10 h, the MeOH was removed under reduced pressure and H$_2$O (500 mL) was added. The solution was acidified with HCl (pH 1), filtered and the precipitate was washed with H$_2$O giving the sub-title compound in a 93% yield.

(b) N$^1$-isopropyl-5-cyano-2(2-oxiranylmethoxy)benzamide

The sub-title compound was prepared according to the method described in Example A above from N$^1$-iso-propyl-5-cyano-2-hydroxybenzamide (from step (a) above).

(c) tert-Butyl 7-{3-[(4-cyano-2-(iso-propylcarbamoyl) phenoxy]-2-hydroxypropyl}-3,7-diazabicyclo[3.3.1] nonane-3-carboxylate The title compound was prepared according to the method described in Example 2 above from N$^1$-isopropyl-5-cyano-2(2-oxiranylmethoxy)-benzamide (from step (b) above).

$^{13}$C NMR (CDCl$_3$): δ 22.64, 28.65, 28.76, 29.30, 31.73, 41.86, 47.64, 49.37, 60.35, 61.24, 64.93, 71.81, 79.49, 104.94, 113.45, 118.40, 123.71, 135.91, 136.47, 155.15, 159.64, 162.12.

Example 12 tert-Butyl 7-[2-hydroxy-3-(4-nitrophenoxy)propyl]-3,7-diazabicyclo-[3.3.1]nonane-3-carboxylate (a) 2[(4-Nitrophenoxy)methyl]oxirane The sub-title compound was prepared according to the method described in Example A above from 4-nitrophenol.

(b) tert-Butyl 7-[2-hydroxy-3-(4-nitrophenoxy)propyl]-3,7-diazabicyclo-[3.3.1]nonane-3-carboxylate The sub-title compound was prepared according to the method described in Example 2 above from 2[(4-nitrophenoxy)methyl]oxirane (from step (a) above).

$^{13}$C NMR (CDCl$_3$): δ 28.64, 28.75, 29.35, 31.98, 47.54, 49.42, 56.83, 60.15, 61.55, 65.00, 71.10, 79.43, 93.82, 114.57, 125.73, 141.43, 155.94, 163.92.

Example 13 tert-Butyl 7-[3-(4-aminophenoxy)-2-hydroxypropyl]-3,7-diazabicyclo-[3.3.1]nonane-3-carboxylate The title compound was prepared quantitatively from tert-butyl 7-[2-hydroxy-3-(4-nitrophenoxy)propyl]-3,7-diazabicyclo[3.3.1]nonane-3-carboxylate (see Example 12 above) using catalytic hydrogenation on 5% Pd/C in EtOH at 1 atm.

$^{13}$C NMR (CDCl$_3$): δ 28.64, 28.82, 29.36, 30.97, 31.78, 47.61, 49.28, 58.19, 60.30, 62.07, 65.28, 71.15, 79.41, 115.71, 116.29, 140.02, 152.04, 155.15.

Example 14 tert-Butyl 7-{2-hydroxy-3-[4-(methylsulfonamido) phenoxy]propyl}-3,7-diazabicyclo[3.3.1]nonane-3-carboxylate MsCl (0.50 g; 4.40 mmol) was added to a stirred solution of tert-butyl 7-[3-(4-aminophenoxy)-2-hydroxypropyl]-3,7-diazabicyclo[3.3.1]nonane-3-carboxylate (1.68 g; 4.29 mmol; see Example 13 above) in pyridine (20 mL). The reaction mixture was stirred for 2.5 h and subsequently concentrated. The residue was partitioned between DCM and NaHCO$_3$ (sat.), the organic layer separated, dried and concentrated. Purification using column chromatography (gradient 0 to 10% MeOH in DCM) gave the title compound in a 87% yield. $^{13}$C NMR (CDCl$_3$): δ 28.70, 28.70, 28.84, 29.09, 29.42, 31.93, 38.77, 47.64, 49.42, 57.01, 60.29, 61.84, 65.20, 70.79, 79.50, 115.48, 116.32, 124.53, 129.40, 155.94, 157.28.

Example 15 tert-Butyl 7-[3-(4-cyano-2-methylphenoxy)-2-hydroxypropyl]-3,7-diazabicyclo[3.3.1]nonane-3-carboxylate (a) 2-Methyl-4-cyanophenol The sub-title compound was prepared according to the method described in Example 10(b) above from 2-methyl-4-bromophenol.

(b) 3-Methyl-4-(2-oxiranylmethoxy)benzonitrile

The sub-title compound was prepared according to the method described in Example A above from 2-methyl-4-cyanophenol (from step (a) above).

(c) tert-Butyl 7-[3-(4-cyano-2-methylphenoxy)-2-hydroxypropyl]-3,7-diazabicyclo[3.3.1]nonane-3-carboxylate The title compound was prepared according to the method described in Example 2 above from 3-methyl-4-(2-oxiranylmethoxy)benzonitrile (from step (b) above).

$^{13}$C NMR (CDCl$_3$): δ 22.84, 28.52, 28.70, 28.89, 32.06, 47.61, 49.51, 56.96, 60.28, 62.00, 65.14, 68.32, 70.65, 79.5, 103.53, 111.26, 119.44, 128.25, 131.85, 133.87, 156.01, 160.40.

Example 16

(tert-Butyl 7-[3-(2-amino-4-cyanophenoxy)-2-hydroxypropyl]-3,7-diazabicyclo[3.3.1]nonane-3-carboxylate (a) 3-Nitro-4-(2-oxiranylmethoxy)benzonitrile 4-Cyano-2-nitrophenol (0.80 g; 4.9 mmol) and K$_2$CO$_3$ (0.68 g; 4.9 mmol) were refluxed in MeCN (40 mL) for 1 h. The solvent was removed on a rotary evaporator and the residue dissolved in DMF (10 mL). 2-{[(3-Nitrophenyl) sulfonyloxy]methyl}oxirane (1.2 g, 4.9 mmol; see Example B above) was added to the resultant solution. The solution was stirred at 40° C. for 12 h and filtered. The precipitate was washed with H$_2$O to give the sub-title compound in a 65% yield.

(b) tert-Butyl 7-[3-(4-cyano-2-nitrophenoxy)-2-hydroxypropyl]-3,7-diazabicyclo[3.3.1]nonane-3-carboxylate 3-Nitro-4-(2-oxiranylmethoxy)benzonitrile (2.9 g; 13.2 mmol; from step (a) above) was added to a stirred solution of tert-butyl 3,7-diazabicyclo[3.3.1]nonane-3-carboxylate (3 g; 13.2 mmol; see Example F above) in IPA:H$_2$O (12.5 mL; 9:1), and the reaction mixture was refluxed for 3 h. Concentration of the reaction mixture and purification by column chromatography (DCM:MeOH; 15:1) gave the title compound in a 54% yield.

$^{13}$C NMR (CDCl$_3$): δ 28.4, 31.8, 47.4, 49.8, 56.7, 59.8, 60.5, 65.0, 71.9, 79.2, 103.7, 116.1, 116.7, 129.3, 137.3, 139.3, 155.4, 155.8.

(c) (tert-Butyl 7-[3-(2-amino-4-cyanophenoxy)-2-hydroxyprolyl]-3,7-diazabicyclo[3.3.1]nonane-3-carboxylate The title compound was prepared in a 98% yield according to the method described in Example 13 above from tert-butyl 7-[3-(4-cyano-2-nitrophenoxy)-2-hydroxypropyl]-3,7-diazabicyclo[3.3.1]nonane-3-carboxylate (from step (b) above).

$^{13}$C NMR (CDCl$_3$): δ 28.2, 31.7, 47.3, 49.2, 56.7, 59.9, 61.3, 65.4, 71.0, 79.2, 103.8, 111.5, 116.5, 119.6, 122.6, 137.4, 149.3, 155.7.

Example 17 tert-Butyl 7-{3-[(4-cyano-2-(methylsulfonamido)phenoxy]-2-hydroxypropyl}-3,7-diazabicyclo[3.3.1]nonane-3-carboxylate The title compound was prepared in a 80% yield according to the method described in Example 14 above from tert-butyl 7-[3-(2-amino-4-cyanophenoxy)-2-hydroxypropyl]-3,7-diazabicyclo[3.3.1]nonane-3-carboxylate (see Example 16 above).

$^{13}$C NMR (CDCl$_3$): δ 28.2, 28.5, 30.6, 39.4, 57.1, 59.4, 59.6, 64.9, 71.2, 77.4, 79.8, 104.3, 112.2, 118.4, 124.6, 129.5, 152.6, 155.7.

Example 18 tert-Butyl 7-[3-(4-cyano-2-{[(ethylamino)carbonyl]amino}phenoxy]-2-hydroxypropyl}-3,7-diazabicyclo[3.3.1]nonane-3-carboxylate (a) N-(5-Cyano-2-hydroxyphenyl)-N'-ethylurea Ethyl isocyanate (7.1 g; 100 mmol) was added to a stirred solution of 2-amino-4-cyanophenol (13.4 g; 100 mmol) in MeCN (250 mL), and the resultant solution was stirred for 12 h. The precipitate was filtered off and dried (vacuum) to give the sub-title compound in a 70% yield.

(b) N-[5-Cyano-2-(oxiranylmethoxy)phenyl]-N'-ethylurea

The sub-title compound was prepared in a 52% yield according to the method described in Example 16(a) above from N-(5-cyano-2-hydroxyphenyl)-N'-ethylurea (from step (a) above).

(c) tert-Butyl 7-[3-(4-cyano-2-{[(ethylamino)carbonyl]amino}phenoxy]-2-hydroxypropyl}-3,7-diazabicyclo[3.3.1]nonane-3-carboxylate The title compound was prepared in a 40% yield according to the method described in Example 16(b) above from N-[5-cyano-2-(oxiranylmethoxy)phenyl]-N'-ethylurea (from step (b) above).

$^{13}$C NMR (CDCl$_3$): δ 15.28, 28.63, 31.66, 34.73, 47.60, 49.42, 57.23, 59.70, 60.24, 65.79, 72.54, 79.71, 105.00, 113.17, 119.58, 121.22, 125.75, 131.44, 149.84, 155.50.

Example 19 tert-Butyl 7-[3-(3,4-dicyanophenoxy)-2-hydroxypropyl]-3,7-diazabicyclo-[3.3.1]nonane-3-carboxylate (a) 4-(2-Oxiranylmethoxy)phthalonitrile A stirred suspension of 4-hydroxyphthalonitrile (3.5 g; 24.3 mmol), K$_2$CO$_3$ (4.03 g; 29.2 mmol) and 2-{[(3-nitrophenyl)sulfonyloxy]methyl}-oxirane (6.50 g; 25.0 mmol; see Example B above) in MeCN (170 mL) was refluxed for 1.5 h. The cooled reaction mixture was filtered, the filtrate concentrated and the solid residue recrystallized from IPA to give the sub-title compound.

(b) tert-Butyl 7-[3-(3,4-dicyanophenoxy)-2-hydroxypropyl]-3,7-diazabicyclo[3.3.1]nonane-3-carboxylate The title compound was prepared in a 55% yield according to the method described in Example 2 above (using MeCN as solvent) from 4-(2-oxiranylmethoxy)phthalonitrile (from step (a) above).

$^{13}$C NMR (CDCl$_3$): δ 28.8, 29.35, 31.96, 47.55, 49.45, 56.75, 60.12, 61.19, 65.14, 71.5, 79.47, 107.14, 115.19, 115.65, 117.15, 119.60, 120.06, 135.04, 155.98, 162.18.

Example 20 tert-Butyl 7-[2-(phenylcarbamoyl)ethyl]-3,7-diazabicyclo[3.3.1]nonane-3-carboxylate (a) N$^1$-Phenylacrylamide Acryloyl chloride (28.5 mL; 350 mmol) was added to a stirred solution of phenylamine (30 mL; 320 mmol) and TEA (56 mL; 400 mmol) in THF (1 L) at 0° C. The reaction mixture was stirred for 3 h, poured onto brine and extracted with diethyl ether. The organic layer was dried, concentrated and recrystallized from hexane:EtOAc (3:1) to give the sub-title compound in a 79% yield.

(b) N$^1$-Phenyl-3-(7-benzyl-3,7-diazabicyclo[3.3.1]non-3-yl)propanamide

N$^1$-Phenylacrylamide (1.0 g; 6.8 mmol; from step (a) above) was added to a stirred solution of 3-benzyl-3,7-diazabicyclo[3.3.1]nonane (1.5 g; 6.8 mmol; see Example E above) in EtOH (7 mL). The reaction mixture was stirred for 10 h and concentrated to give the sub-title compound in a 97% yield.

(c) tert-Butyl 7-[2-(phenylcarbamoyl)ethyl]-3,7-diazabicyclo[3.3.1]nonane-3-carboxylate A solution of N$^1$-phenyl-3-(7-benzyl-3,7-diazabicyclo[3.3.1]non-3-yl)-propanamide (2.5 g; 6.8 mmol; from step (b) above) and di-tert-butyl dicarbonate (3.3 g; 15 mmol) in EtOH (25 mL) was hydrogenated over 5% Pd/C at 1 atm for 20 min., filtered through a pad of celite and concentrated. Purification by column chromatography (DCM:MeOH; 19:1) gave the title compound in a 90% yield.

$^{13}$C NMR (CDCl$_3$): δ 28.55, 30.29, 35.84, 48.00, 49.14, 55.08, 58.09, 79.29, 120.15, 123.79, 128.87, 138.47, 156.07, 171.41.

Example 21 tert-Butyl 7-[3-(4-cyanophenoxypropyl)]-3,7-diazabicyclo[3.3.1]nonane-3-carboxylate (a) 4-(3-Bromopropoxy)benzonitrile 1,3-Dibromopropane (1.02 L; 10 mol) was added to a stirred suspension of p-cyanophenol (238 g; 2 mol), K$_2$CO$_3$ (276.4 g; 2 mol) in MeCN (2.7 L). The reaction mixture was refluxed for 4 h, filtered and concentrated. The residue was recrystallized from iso-propyl ether to give the sub-title compound in a 69% yield.

(b) tert-Butyl 7-[3-(4-cyanophenoxypropyl)]-3,7-diazabicyclo-[3.3.1]nonane-3-carboxylate A stirred solution of 4-(3-bromopropoxy)benzonitrile (1.2 g; 52 mmol; from step (a) above), TEA (0.35 mL) and tert-butyl 3,7-diazabicyclo[3.3.1]nonane-3-carboxylate (1.17 g; 52 mmol; see Example F above) in DMSO (2 mL) was heated to 60° C. for 12 h. The reaction mixture was partitioned between Na$_2$CO$_3$ (aq.) and DCM and the organic layer separated, dried and subjected to column chromatography (DCM:MeOH; 22:1) to give the title compound in a 74% yield.

FAB-MS (M+1)$^+$386 (m/z); $^{13}$C NMR (CDCl$_3$): δ 26.47, 28.52, 28.87, 31.31, 47.54, 48.72, 55.21, 58.29, 59.26, 66.56, 78.46, 103.42, 115.19, 119.21, 133.78, 154.98, 162.28.

Example 22 tert-Butyl 7-{2-[(4-cyanophenyl)carbamoyl]ethyl}-3,7-diazabicyclo-[3.3.1]nonane-3-carboxylate (a) N$^1$-(4-Cyanophenyl)-3-chloropropanamide 3-Chloropropionylchloride (1.08 g; 8.5 mmol) was added to a cooled (10° C.) solution of 4-cyanoaniline (1.0 g; 8.5 mmol) and pyridine (0.69 mL; 8.5 mnol) in DCM (40 mL), and the reaction mixture was stirred at rt. for 1 h. The reaction mixture was extracted with HCl (2N), washed with water, dried and concentrated to give the sub-title compound in a 81% yield.

(b) tert-Butyl 7-{2-[(4-cyanophenyl)carbamoyl]ethyl}-3,7-diazabicyclo-[3.3.1]nonane-3-carboxylate The title compound was prepared in a 74% yield according to the method described in Example 21(b) above from N$^1$-(4-cyanophenyl)-3-chloropropanamide (from step (a) above).

$^{13}$C NMR (CDCl$_3$): δ 28.5, 30.5, 36.5, 48.1, 49.3, 55.1, 59.0, 79.5, 106.4, 119.1, 120.0, 133.1, 142.7, 156.3, 172.1.

Example 23 tert-Butyl 7-[3-(4-cyanoanilino)propyl]-3,7-diazabicyclo[3.3.1]nonane-3-carboxylate LiBH$_4$ (300 mg; 13.6 mmol) was added to a stirred solution of tert-butyl 7-{2-[(4-cyanophenyl)carbamoyl]ethyl}-3,7-diazabicyclo[3.3.1]nonane-3-carboxylate (1.36 g; 3.41 mmol; see Example 22 above) in toluene (10 mL) and THF (5 mL) and the reaction mixture was stirred for 45 min. The solvents were removed and the residue partitioned between DCM and NaHCO$_3$ (aq.). The organic layer was concentrated and subjected to column chromatography (DCM:MeOH; 9:1) to give the title compound in a 10% yield.

$^{13}$C NMR (CDCl$_3$): δ 25.5, 28.6, 31.2, 41.1, 47.7, 48.8, 56.9, 59.0, 79.0, 97.4, 111.8, 120.7, 133.6, 151.7, 155.3.

Example 24 iso-Propyl 7-[2-(4-cyanophenyl)-2-hydroxyethyl]-3,7-diazabicyclo[3.3.1]-nonane-3-carboxylate (a) 4-(2-Oxiranyl)benzonitrile NaBH$_4$ (1.6 g; 40 mmol) was added to a stirred solution of 4-cyanophenacyl bromide (8.8 g; 40 mmol) in THF (100 mL), and the reaction mixture was stirred until tlc indicated that the reaction was complete. The solvent was evaporated and the residue partitioned between DCM and H$_{2O}$, and the organic layer was separated, dried and concentrated. The residue was treated with K$_2$CO$_3$ (0.08 mol) in MeCN (85 mL) at room temperature overnight. The solvent was removed on a rotary evaporator and the residue partitioned between CH$_2$Cl$_2$ and H$_2$O. The organic layer was washed with H$_2$O (2×100 mL), separated and dried to give the sub-title compound in 90% overall yield.

(b) iso-Propyl 7-[2-(4-cyanophenyl)-2-hydroxyethyl]-3,7-diazabicyclo-[3.3.1]nonane-3-carboxylate The crude reaction mixture from step (a) above was condensed with iso-propyl 3,7-diazabicyclo[3.3.1]nonane-3-carboxylate (5.2 g; see Example H above) according to the method described in Example 7 above to give the title compound in a 73% overall yield.

FAB-MS (M+1)$^+$358 (m/z); $^{13}$C NMR (CDCl$_3$): δ 22.39, 29.18, 32.76, 48.50, 49.38, 56.17, 59.90, 68.06, 68.46, 110.84, 119.03, 126.58, 132.04, 148.37, 157.32.

Example 25 iso-Propyl 7-(4-cyanophenethyl)-3,7-diazabicyclo[3.3.1]nonane-3-carboxylate (a) 4-Cyanophenethyl methanesulfonate MsCl (18.6 g; 164 mmol) was added to a stirred solution of 4-(2-hydroxyethyl)benzonitrile (20 g; 136 mmol) and TEA (20.6 g; 204 mmol) in DCM (200 mL) at 0° C. The reaction mixture was stirred at rt. until tlc indicated that the reaction was complete. Water (200 mL) was added and the organic layer was separated, dried and concentrated to give the sub-title compound in a quantitative yield.

(b) iso-Propyl 7-(4-cyanophenethyl)-3,7-diazabicyclo [3.3.1]nonane-3-carboxylate iso-Propyl 3,7-diazabicyclo[3.3.1]nonane-3-carboxylate (1.06 g; 5 mmol; see Example H above) was added to a stirred suspension of 4-cyanophenethyl methanesulfonate (1.13 g; 5 mmol; from step (a) above) and K$_2$CO$_3$ (0.96 g; 7 mmol) in MeCN (5 mL) under an inert atmosphere (N$_2$), and the reaction mixture was stirred for 10 h. The solvent was evaporated and the residue partitioned between DCM and NaHCO$_3$ (aq.). The organic layer was separated, dried and concentrated. Purification using column chromatography (DCM:MeOH; 19:1) gave the title compound in a 88% yield.

FAB-MS (M+1)$^+$342 (m/z); $^{13}$C NMR (CD$_3$CN): δ 22.61, 22.67, 30.12, 30.16, 32.20, 34.02, 49.02, 49.18, 58.99, 59.68, 60.98, 68.26, 110.21, 119.89, 130.57, 132.99, 148.19, 156.33.

Example 26 tert-Butyl 7-(2-{[(benzyloxy)carbonyl]amino}ethyl)-3,7-diazabicyclo-[3.3.1]nonane-3-carboxylate (a) Benzyl-N-(2-bromoethyl)carbamate A solution of CBz-Cl (7.7 mL; 54 mmol) in dioxane (5 mL) was added to a cold (0° C.) stirred solution of 2-bromoethylamine hydrobromide (10.0 g; 49 mmol) in 40 mL 1M NaOH:dioxane (3:1) under Schotten-Bauman conditions. The reaction mixture was allowed to attain rt. and extracted with CHCl$_3$. The organic layer was separated, concentrated and purified by column chromatography (CHCl$_3$) to give the sub-title compound in a 92% yield.

(b) tert-Butyl 7-(2-{[(benzyloxy)carbonyl]amino}ethyl)-3,7-diazabicyclo-[3.3.1]nonane-3-carboxylate The title compound was prepared in a 44% yield according to the method in Example 25(b), using benzyl-N-(2-bromoethyl)carbamate (from step (a) above).

$^{13}$C NMR (CDCl$_3$): δ 28.64, 31.96, 37.89, 47.67, 49.38, 57.72, 59.30, 66.30, 79.11, 127.71, 128.05, 128.30, 137.08, 155.77, 156.88.

Example 27 tert-Butyl 7-{2-[4-cyanobenzylamino]ethyl}-3,7-diazabicyclo[3.3.1]-nonane-3-carboxylate (a) tert-Butyl 7-[2-aminoethyl]-3,7-diazabicyclo[3.3.1]nonane-3-carboxylate The sub-title compound was prepared according to the method described in Example E(b) in a quantitative yield from tert-butyl 7-(2-{[(benzyloxy)-carbonyl]amino}ethyl)-3,7-diazabicyclo[3.3.1]nonane-3-carboxylate (see Example 26 above).

(b) tert-Butyl 7-{2-[4-cyanobenzylamino]ethyl}-3,7-diazabicyclo[3.3.1]-nonane-3-carboxylate p-Cyanobenzylbromide (0.765 g; 3.9 mmol) was added to a stirred solution of tert-butyl 7-[2-aminoethyl]-3,7-diazabicyclo[3.3.1]nonane-3-carboxylate (1.04 g; 3.9 mmol; from step (a) above) in MeCN (15 mL) and the reaction mixture was stirred at 40° C. for 32 h. The solvent was evaporated and the residue subjected to column chromatography (EtOAc) to give the title compound in a 74% yield.

$^{13}$C NMR (CD$_3$OD): δ 27.65, 29.17, 31.06, 51.92, 57.34, 58.41, 78.86, 110.41, 118.41, 129.23, 131.89, 145.74, 155.91.

Example 28

(R,R)- and (R,S) or (S,R)- and (S,S)-tert-Butyl 7-[4-(4-cyanophenyl)-2,4-dihydroxybutyl]-3,7-diazabicyclo[3.3.1]nonane-3-carboxylate (a) 4-Acetoxy-4-(p-cyanophenyl)-1-butene The sub-title compound was prepared according to the method described in J. Am. Chem. Soc., 110, 3601 (1988).

(b) 1-(4-Cyanophenyl)-2-(2-oxiranyl)ethyl acetate mCPBA (2.86 g; 70%) was added to a stirred solution of 4-acetoxy-4-(p-cyanophenyl)-1-butene (2.5 g; 11.6 mmol; from step (a) above) in DCM (20 mL), and the reaction mixture was refluxed for 3 h and then cooled. The m-chlorobenzoic acid was removed by filtration and the filtrate was washed with NaHCO$_3$ (aq.), then with water, the phases were separated, dried, concentrated and purified by column chromatography (DCM) to give the sub-title compound in a 50% yield.

(c) tert-Butyl 7-[4-(4-cyanophenyl)-2-hydroxy-4-(methylcarbonyloxy)-butyl]-3,7-diazabicyclo[3.3.1]nonane-3-carboxylate The sub-title compound was prepared in a 82% yield according to the method described in Example 2 above using 1-(4-cyanophenyl)-2-(2-oxiranyl)ethyl acetate (from step (b) above).

FAB-MS (M+1)$^+$458 (m/z); $^{13}$C NMR (CDCl$_3$): δ 21.04, 28.57, 29.34, 31.81, 41.88, 47.58, 56.97, 60.51, 62.43, 65.46, 72.47, 79.41, 111.36, 118.59, 126.82, 132.22, 145.85, 155.99, 169.83.

(d) (R,R)- and (R,S) or (S,R)- and (S,S)-tert-Butyl 7-[4-(4-cyanophenyl)-2,4-dihydroxybutyl]-3,7-diazabicyclo[3.3.1]nonane-3-carboxylate tert-Butyl 7-[4-(4-cyanophenyl)-2-hydroxy-4-(methylcarbonyloxy)butyl]-3,7-diazabicyclo[3.3.1]nonane-3-carboxylate (1.88 g; 4.12 mmol; from step (c) above) was deprotected as follows: A solution of NaOH (0.21 g; 5 mmol) in MeOH (2 mL) was added to a stirred solution of the protected intermediate in MeOH (2 mL). The reaction mixture was refluxed for 2 h, partitioned between diethyl ether and water, and the organic layer separated, dried, concentrated and subjected to column chromatography (DCM:MeOH; 49:1) to give two separable diastereomeric pairs in a 88% yield. The title compound was isolated as the less polar diastereoisomers.

ESI-MS (M+1)$^+$417 (m/z);

$^{13}$C NMR (CDCl$_3$): δ 28.25, 28.88, 30.69, 31.54, 43.18, 47.19, 48.31, 49.02, 56.29, 59.68, 64.65, 66.34, 72.97, 79.13, 110.09, 118.55, 126.10, 131.57, 149.93, 155.59.

Example 29

(S,R)- and (S,S)- or (R,R)- and (R,S)-tert-Butyl 7-[4-(4-cyanophenyl)-2,4-dihydroxybutyl]-3,7-diazabicyclo[3.3.1]nonane-3-carboxylate The title compound was isolated as the more polar diastereoisomers from Example 28 above.

ESI-MS (M+1)$^+$416 (m/z); $^{13}$C NMR (CDCl$_3$): δ 28.35, 29.00, 30.78, 31.62, 42.07, 47.24, 48.32, 49.13, 56.34, 59.86, 63.16, 64.27, 70.15, 79.23, 110.00, 118.73, 126.15, 131.68, 150.59, 155.68.

Example 30 tert-Butyl 7-[4-(4-cyanophenyl)-4-hydroxybutyl]-3,7-diazabicyclo[3.3.1]-nonane-3-carboxylate (a) 4-1 (-{[1-(tert-Butyl)-1,1-dimethylsilyl]oxy}-3-butenyl) benzonitrile Imidazole (11.5 g; 170 mmol) was added to a stirred solution of 1-(p-cyanophenyl)-3-buten-1-ol (11.5 g; 87 mmol) and tert-butyldimethylsilyl chloride (12 g; 80 mmol) in DMF (50 mL), and the reaction mixture was stirred under N$_2$(g) for 10 h. The solvent was evaporated and the residue partitioned between water and diethyl ether. The organic layer was separated, dried, concentrated and subjected to column chromatography (DCM) to give the sub-title compound in a 86% yield.

(b) 4-1(-{[1-(tert-Butyl)-1,1-dimethylsilyl]oxy}-4-hydroxybutyl) benzonitrile

Borane-methyl sulfide complex (13 mL; 2M; 26 mmol) was added to a stirred and cooled (0° C.) solution of 4-1(-{[1-(tert-butyl)-1,1-dimethylsilyl]oxy}-3-butenyl) benzonitrile (15.2 g; 53 mmol; from step (a) above) in THF (100 mL). The temperature was raised to rt. and stirred until tlc indicated complete consumption of the starting material. The temperature was lowered to 0° C. and a solution of sodium perborate tetrahydrate (19 g; 123 mmol) in water (55 mL) was added and the resultant reaction mixture was stirred at rt. for 12 h. Brine (100 mL) and diethyl ether (150 mL) was added and the organic layer was separated, dried, concentrated and subjected to column chromatography (hexane:EtOAc; 1:1) to give the sub-title compound in a 85% yield.

(c) 4-{[-1-(tert-Butyl)-1,1-dimethylsilyl]oxy}-4-(4-cyanophenyl)butyl methanesulfonate The sub-title compound was prepared in a 98% yield according to the method described in Example 25(a) above from 4-1(-{[1-(tert-butyl)-1,1-dimethylsilyl]oxy}-4-hydroxybutyl)benzonitrile (from step (b) above).

(d) tert-Butyl 7-[4-(4-cyanophenyl)-4-{[-1-(tert-butyl)-1,1-dimethylsilyl]-oxy}butyl]-3,7-diazabicyclo[3.3.1]nonane-3-carboxylate The sub-title compound was prepared in 96% yield according to the method described in Example 25(b) above from 4-{[-1-(tert-butyl)-1,1-dimethylsilyl]oxy}-4-(4-cyanophenyl)butyl methanesulfonate (from step (c) above) and tert-butyl 3,7-diazabicyclo[3.3.1]nonane-3-carboxylate (see Example F above).

(e) tert-Butyl 7-[4-(4-cyanophenyl)-4-hydroxybutyl]-3,7-diazabicyclo-[3.3.1]nonane-3-carboxylate Tetrabutylammonium fluoride (0.95 mmol) was added to a stirred solution of tert-butyl 7-[4-(4-cyanophenyl)-4-{[-1-(tert-butyl)-1,1-dimethylsilyl]-oxy}butyl]-3,7-diazabicyclo[3.3.1]nonane-3-carboxylate (0.44 g; 0.85 mnol; from step (d) above) in THF (5 mL), and the resultant reaction mixture was stirred for 2 h. The solvent was evaporated and the residue was subjected to column chromatography (MeCN:MeOH; gradient 0 to 10% MeOH) to give the title compound in a 70% yield.

ESI-MS (M+1)$^+$400 (m/z); $^{13}$C NMR (CDCl$_3$): δ 22.26, 28.37, 30.10, 37.26, 37.63, 47.68, 48.53, 57.73, 58.34, 59.12, 72.49, 78.95, 110.03, 119.05, 126.59, 131.71, 151.05, 155.58.

Example 31 iso-Propyl 7-[4-(4-cyanophenyl)-4-hydroxybutyl]-3,7-diazabicyclo[3.3.1]-nonane-3-carboxylate (a) 3-(4-Cyanophenyl)-4-hydroxybutyl]-3,7-diazabicyclo[3.3.1]nonane HCl-saturated EtOAc (200 mL) was added to a stirred solution of tert-butyl 7-[4-(4-cyanophenyl)-4-{[-1-(tert-butyl)-1,1-dimethylsilyl]oxy}-butyl]-3,7-diazabicyclo[3.3.1]nonane-3-carboxylate (4.60 g; see Example 30(d) above) in EtOAc (50 mL), and the reaction mixture was stirred for 2 h. The solvent was evaporated and the residue dissolved in EtOH and passed through an ion-exchange resin (Amberlyst IRA 400), concentrated and lyophilized to give the sub-title compound in a quantitative yield.

(b) iso-Propyl 7-[4-(4-cyanophenyl)-4-hydroxybutyl]-3,7-diazabicyclo-[3.3.1]nonane-3-carboxylate The title compound was prepared in a 77% yield according to the method described in Example H(a) above from 3-(4-cyanophenyl)-4-hydroxybutyl]-3,7-diazabicyclo[3.3.1]nonane (from step (a) above).

FAB-MS (M+1)$^+$386 (m/z); $^{13}$C NMR (CDCl$_3$): δ 22.33, 23.02, 28.57, 28.71, 30.78, 37.35, 48.21, 57.91, 58.50, 58.89, 59.46, 68.13, 72.54, 73.07, 110.17, 119.21, 126.61, 131.84, 151.26, 156.03.

Example 32 iso-Propyl 7-[(2S)-3-(4-cyanophenoxy)-2-hydroxy-2-methylpropyl]-3,7-diazabicyclo[3.3.1]nonane-3-carboxylate (a) [(2S)-2-Methyloxiran-2-yl]methyl 3-nitro-1-benzenesulfonate The sub-title compound was prepared according to the method described in Example B above from R-(+)-2-methylglycidol.

(b) 4-{[(2S)-Methyloxiran-2-yl]methoxy}benzonitrile

A suspension of [(2S)-2-methyloxiran-2-yl]methyl 3-nitro-1-benzenesulfonate (37.7 g; 138 mmol; from step (a) above), K$_2$CO$_3$ (28 g) and p-cyanophenol (23.8 g; 200 mmol) in MeCN (300 mL) was refluxed for 20 h. The reaction mixture was ffiltered and the filtrate concentrated under reduced pressure, dissolved in ether and washed with 2M NaOH and then brine. The organic layer was concentrated and subjected to column chromatography (petroleum ether:EtOAc; 3:1) to give the sub-title compound.

(c) iso-Propyl 7-[(2S)-3-(4-cyanophenoxy)-2-hydroxy-2-methylpropyl]-3,7-diazabicyclo[3.3.1]nonane-3-carboxylate The title compound was prepared according to the method described in Example 7 above from 4-{[(2S)-methyloxiran-2-yl]methoxy}benzonitrile (from step (b) above).

$^{13}$C NMR (CDCl$_3$): δ 22.38, 22.80, 29.20, 29.56, 31.11, 48.09, 60.93, 61.78, 64.19, 68.83, 71.32, 72.24, 103.91, 115.42, 119.25, 134.01, 155.26, 161.94.

Example 33 tert-Butyl 7-[(2S)-3-(4-cyanophenoxy)-2-hydroxy-2-methylpropyl]-3,7-diazabicyclo[3.3.1]nonane-3-carboxylate The title compound was prepared according to the method described in Example 2 above from 4-{[(2S)-methyloxiran-2-yl]methoxy}benzonitrile (see Example 32(b) above).

ESI-MS (M+1)$^+$416 (m/z); $^{13}$C NMR (CDCl$_3$): δ 22.55, 28.57, 29.51, 30.92, 47.93, 48.62, 60.82, 62.04, 63.84, 71.41, 80.0, 104.01, 119.23, 134.09, 154.74, 161.92.

Example 34

2-Hydroxy-1,1-dimethylethyl 7-[3-(4-cyanophenoxy)-2-hydroxypropyl]-3,7-diazabicyclo[3.3.1]nonane-3-carboxylate (a) Ethyl-2-(chlorocarbonyloxy)-2-methylpropanoate The sub-title compound was prepared according to the method described in Zh. Org. Khim., 7, 1875 (1971).

(b) 2-Ethoxy-1,1-dimethyl-2-oxymethyl 7-benzyl-3,7-diazabicyclo[3.3.1]-nonane-3-carboxylate A solution of 3-benzyl-3,7-diazabicyclo[3.3.1]nonane (23.8 g; 110 mmol; see Example E above) in toluene (100 mL) was added to a stirred solution of ethyl-2-(chlorocarbonyloxy)-2-methylpropanoate (100 mmol) in toluene (25 mL). The reaction mixture was cooled to 0° C. and TEA (25 mL; 180 mmol) was added. After 2 h, the salts were filtered off and the residue concentrated, dissolved in DCM and washed with NaHCO$_3$ (aq.). The organic layer was separated, dried and concentrated to give the sub-title compound in a 90% yield.

(c) 2-Hydroxy-1,1-dimethylethyl 7-benzyl-3,7-diazabicyclo[3.3.1]-nonane-3-carboxylate LiBH$_4$ (0.6 g; 26.7 mmol) was added to a stirred solution of 2-ethoxy-1,1-dimethyl-2-oxymethyl 7-benzyl-3,7-diazabicyclo[3.3.1]-nonane-3-carboxylate (5 g; 13.35 mmol; from step (b) above) in THF (30 mL) and toluene (20 mL), and the reaction mixture was heated at 100° C. for 30 min. Water (10 mL) and NaHCO$_3$ (aq.) was added and the solution was extracted with DCM. The organic layer was washed with water (3×100 mL), separated, dried, concentrated and subjected to column chromatography (DCM:MeOH sat. with NH$_3$; 35:1) to give the sub-title compound in a 20% yield.

(d) 2-Hydroxy-1,1-dimethylethyl 7-[3-(4-cyanophenoxy)-2-hydroxy-propyl]-3,7-diazabicyclo[3.3.1]nonane-3-carboxylate 2-Hydroxy-1,1-dimethylethyl 7-benzyl-3,7-diazabicyclo[3.3.1]-nonane-3-carboxylate (from step (c) above) was debenzylated according to the method described in Example E(b) above and subsequently reacted with 4-(2-oxiranylmethoxy)benzonitrile (see Example A above) in accordance with the method described in Example 2 above to give the title compound in an overall yield of 88%.

ESI-MS (M+1)$^+$418 (m/z); $^{13}$C NMR (CDCl$_3$): δ 26.02, 26.66, 29.25, 29.47, 32.73, 48.91, 49.65, 56.52, 60.07, 62.27, 65.08, 69.85, 70.63, 72.86, 104.08, 115.33, 119.17, 133.90, 157.68, 162.12.

Example 35

1-Cyano-1-methylethyl 7-[3-(4-cyanophenoxy)-2-hydroxypropyl]-3,7-diazabicyclo[3.3.1]nonane-3-carboxylate (a) 1-Cyano-1-methylethyl chloroformate A solution of acetone cyanohydrin (5 g; 59 mmol) in pyridine (5 mL) was added to a stirred solution of COCl$_2$ (30 mL; 1.92 M; 59 mmol) at −15° C. The temperature was raised to rt. and the reaction mixture was stirred for 2 h. The precipitate was filtered off and the filtrate was concentrated and used directly in the next step without further purification.

(b) 1-Cyano-1-methylethyl 7-[3-(4-cyanophenoxy)-2-hydroxypropyl]-3,7-diazabicyclo[3.3.1]nonane-3-carboxylate 1-Cyano-1-methylethyl chloroformate (0.4 g; 1.65 mmol; from step (a) above) was added to a stirred solution of 4-[3-(3,7-diazabicyclo[3.3.1]non-3-yl)-2-hydroxypropoxy] benzonitrile (0.5 g; 1.65 mmol; see Example G above) and $K_2CO_3$ (0.7 g) in MeCN (25 mL). The reaction mixture was stirred at 40° C. for 2 h. The salts were filtered off and the filtrate was concentrated and subjected to column chromatography (DCM:MeOH; 19:1) to give the title compound in a 59% yield.

ESI-MS (M+1)$^+$413 (m/z); $^{13}$C NMR (CDCl$_3$): δ 27.29, 27.78, 28.60, 29.13, 31.31, 48.30, 49.22, 57.90, 60.29, 61.52, 65.66, 68.90, 70.67, 104.101, 115.46, 119.22, 120.29, 133.96, 153.58, 162.19.

Example 36

3,4-Dimethoxyphenethyl 7-[3-(4-cyanophenoxy)-2-hydroxypropyl]-3,7-diazabicyclo[3.3.1]nonane-3-carboxylate (a) 3,4-Dimethoxyphenethyl 7-benzyl-3,7-diazabicyclo[3.3.1]nonane-3-carboxylate 3,4-Dimethoxyphenethyl alcohol (3.64 g; 20 mmol) was added to a stirred suspension of 1,1'-carbonyldiimidazole (3.24 g; 20 mmol) in THF (20 mL), and the mixture was refluxed for 12 h. A solution of 3-benzyl-3,7-diazabicyclo[3.3.1]nonane (4.33 g; 20 mmol; see Example E above) in THF (20 mL) was added and the reaction mixture was refluxed overnight. The solvent was removed and the residue dissolved in $H_2SO_4$ (2M; 25 mL) and extracted with diethyl ether. NaOH (3.5 mL; 5M) was added and the aqueous phase extracted with DCM. The organic layer was separated, dried and subjected to column chromatography (DCM:MeOH; gradient 0 to 30% MeOH) to give the sub-title compound in a 29% yield.

(b) 3,4-Dimethoxyphenethyl 3,7-diazabicyclo[3.3.1]nonane-3-carboxylate

The sub-title compound was prepared in a 70% yield according to the method described in Example E(b) above from 3,4-dimethoxyphenethyl 7-benzyl-3,7-diazabicyclo[3.3.1]nonane-3-carboxylate (from step (a) above).

(c) 3,4-Dimethoxyphenethyl 7-[3-(4-cyanophenoxy)-2-hydroxypropyl]-3,7-diazabicyclo[3.3.1]nonane-3-carboxylate The title compound was prepared in a 45% yield according to the method described in Example 2 above from 3,4-dimethoxyphenethyl 3,7-diazabicyclo[3.3.1]nonane-3-carboxylate (from step (b) above).

$^{13}$C NMR (CDCl$_3$): δ 28.9, 32.3, 34.8, 48.3, 49.0, 55.5, 56.2, 59.5, 62.0, 64.6, 65.7, 70.6, 103.6, 111.0, 112.2, 115.0, 118.8, 120.7, 130.8, 133.5, 147.3, 148.5, 157.1, 161.8.

Example 37

Phenyl 7-[3-(4-cyanophenoxy)-2-hydroxyprolyl]-3,7-diazabicyclo[3.3.1]-nonane-3-carboxylate Phenyl chloroformate (0.36 mL; 2.9 mmol) and NaOH (0.52 mL; 10M, 5.2 mmol) were added to a stirred solution of 4-[3-(3,7-diazabicyclo[3.3.1]non-3-yl)-2-hydroxypropoxy]benzonitrile (0.796 g; 2.6 mmol; see Example G above) in toluene (5 mL). The reaction mixture was stirred at rt. for 15 min. DCM was added and the organic layer was separated, dried, concentrated and recrystallized from IPA to give the title compound in a 86% yield.

$^{13}$C NMR (CDCl$_3$): δ 28.8, 29.2, 32.0, 48.6, 49.6, 56.9, 60.0, 62.1, 65.1, 70.5, 103.7, 115.2, 119.0, 121.6, 124.9, 128.9, 133.6, 151.1, 154.9, 162.0.

Example 38

Benzyl 7-[3-(4-cyanophenoxy)-2-hydroxyprolyl]-3,7-diazabicyclo[3.3.1]-nonane-3-carboxylate The title compound was prepared in quantitative yield according to the method described in Example 1 above from CBz-OSu, using TEA, instead of NaOH, as a base.

ESI-MS (M+1)$^+$436 (m/z); $^{13}$C NMR (CDCl$_3$): δ 29.31, 32.70, 48.88, 49.55, 56.77, 60.21, 62.47, 65.13, 67.28, 70.86, 104.04, 115.40, 119.23, 127.93, 128.43, 133.94, 136.91, 157.39, 166.22.

Example 39 tert-Butyl 7-[(2S)-3-(4-cyanophenoxy)-2-hydroxypropyl]-9-(1,2-ethylenedioxy)-3,7-diazabicyclo[3.3.1]nonane-3-carboxylate (a) 3,7-Dibenzyl 9-(1,2-ethylenedioxy)-3,7-diazabicyclo[3.3.1]nonane A solution of 3,7-dibenzyl-3,7-diazabicyclo[3.3.1]nonane-9-one (10.0 g; 29.8 mmol; Bionet), ethylene glycol (20 g) and p-TSA (12.5 g; 65.7 mmol) in toluene (200 mL) was refluxed in a Dean-Stark apparatus for 12 h. NaOH (200 mL, 2M) was added and the organic layer separated, dried and concentrated to give the sub-title compound in a quantitative yield.

(b) tert-Butyl 7-benzyl-9-(1,2-ethylenedioxy)-3,7-diazabicyclo[3.3.1-]nonane-3-carboxylate The sub-title compound was prepared in a 92% yield according to the method described in Example 20(c) above from 3,7-dibenzyl 9-(1,2-ethylenedioxy)-3,7-diazabicyclo[3.3.1]nonane (from step (a) above).

(c) tert-Butyl 9-(1,2-ethylenedioxy)-3,7-diazabicyclo[3.3.1]nonane-3-carboxylate The sub-title compound was prepared in quantitative yield according to the method described in Example E(b) above from tert-butyl 7-benzyl-9-(1,2-ethylenedioxy)-3,7-diazabicyclo[3.3.1]nonane-3-carboxylate (from step (b) above).

(d) tert-Butyl 7-[(2S)-3-(4-cyanophenoxy)-2-hydroxypropyl]-9-(1,2-ethylenedioxy)-3,7-diazabicyclo[3.3.1]nonane-3-carboxylate The title compound was prepared in a 44% yield according to the method described in Example 3 above from tert-butyl 9-(1,2-ethylenedioxy)-3,7-diazabicyclo[3.3.1]nonane-3-carboxylate (from step (c) above).

$^{13}$C NMR (CDCl$_3$): δ 28.78, 37.71, 38.37, 46.00, 47.42, 53.83, 57.81, 60.81, 64.40, 65.45, 70.80, 79.81, 104.06, 106.95, 115.44, 119.24, 133.93, 156.24, 162.27.

Example 40 tert-Butyl 7-[3-(4-cyanophenoxy)-2-hydroxypropyl]-9,9-pentamethylene-3,7-diazabicyclo[3.3.1]nonane-3-carboxylate (a) N-(Cyanoacetyl) benzylamide A mixture of benzyl amine (150 mL; 1.4 mol) and methyl cyanoacetate (130 mL; 1.4 mol) was stirred at 100° C. for 16 h with continuous removal of MeOH. The reaction mixture was allowed to attain rt. and the precipitate filtered off and washed with cold EtOH to give the sub-title compound in a 78% yield.

(b) Ethyl (2-cyclopentylidene)cyanoacetate

The sub-title compound was prepared in a 69% yield analogously to the method described in Organic Synthesis, 39, 25 (1959) from cyclopentanone and ethyl cyanoacetate.

(c) 8-Benzyl-7,9-dioxo-8-azaspiro[4,5]decane-6,10-dicarbonitrile N-(Cyanoacetyl) benzylamide (2.30 g; 13.2 mmol; from step (a) above) and ethyl (2-cyclopentylidene) cyanoacetate (2.36 g; 13.2 mmol; from step (b) above) were added to a stirred solution of sodium ethoxide (13 mmol) in EtOH (20 mL), and the reaction mixture was stirred at rt. for 96 h. Water (16 mL) and HCl (5 mL, conc.) were added and the precipitate filtered off, washed with water and dried in. vacuo to give the sub-title compound in a 55% yield.

(d) 3-Benzyl-9,9-pentamethylene-3,7-diazabicyclo[3.3.1] nonane-2,4,6,8-tetraone

8-Benzyl-7,9-dioxo-8-azaspiro[4,5]decane-6,10-dicarbonitrile (4.0 g; 13 mmol; from step (c) above) was stirred in $H_2SO_4$ (20 mL, conc.) and $H_3PO_4$ (85%) for 40 min. at 120° C. The hot reaction mixture was poured on ice-water and the precipitate filtered off, washed with EtOH and dried in vacuo to give the sub-title compound in a 43% yield.

(e) 3-Benzyl-9,9-pentamethylene-3,7-diazabicyclo[3.3.1] nonane

3-Benzyl-3,7-diazabicyclo[3.3.1]nonane-2,4,6,8-tetraone (from step (d) above) was reduced with $LiAlH_4$ in dioxane using standard procedures to give the sub-title compound in a quantitative yield.

(f) tert-Butyl 7-benzyl-9,9-pentamethylene-3,7-diazabicyclo [3.3.1]nonane-3-carboxylate Di-tert-butyl dicarbonate (0.92 g; 4.2 mmol) was added to a solution of 3-benzyl-9,9-pentamethylene-3,7-diazabicyclo [3.3.1]nonane (1.15 g; 4.2 mmol; from step (e) above) in THF (50 mL) and the reaction mixture was stirred until tlc indicated that the reaction was complete. The solvent was removed on a rotary evaporator to give the sub-title compound in a 79% yield.

$^{13}C$ NMR (CDCl$_3$): δ 23.80, 28.64, 30.26, 34.87, 35.21, 37.40, 42.43, 46.09, 46.68, 55.92, 56.46, 62.80, 78.58, 126.53, 128.00, 128.32, 139.53, 155.37.

(g) tert-Butyl 7-[3-(4-cyanophenoxy)-2-hydroxypropyl]-9, 9-pentamethylene-3,7-diazabicyclo[3.3.1]nonane-3-carboxylate The title compound was prepared in a 53% overall yield according to the methods described in Examples E(b) and 2 above from tert-butyl 7-benzyl-9,9-pentamethylene-3,7-diazabicyclo[3.3.1]nonane-3-carboxylate (from step (f) above).

$^{13}C$ NMR (CDCl$_3$): δ 23.83, 28.68, 35.13, 37.30, 42.77, 45.82, 46.84, 47.02, 54.26, 57.90, 61.04, 65.34, 70.77, 79.32, 104.03, 115.44, 119.17, 133.85, 156.00, 162.34.

Example 41

7-(tert-Butyloxycarbonyl)-3-[3-(4-cyanophenoxy)-2S-hydroxypropyl]-3-methyl-7-aza-3-azoniabicyclo [3.3.1]nonane acetate MeI (1.5 mmol) was added to a stirred solution of tert-butyl 7-[3-(4-cyanophenoxy)-2-hydroxypropyl]-3,7-diazabicyclo[3.3.1]nonane-3-carboxylate (0.5 g; 1.24 mmol; see Example 2 above) in DMF (4 mL), and the reaction mixture was stirred at rt. for 48 h. Toluene was then added and the solvents removed under vacuum. The residue was purified using HPLC (MeCN:H$_2$O; 70:30 isocratic; NH$_4$OAc-buffer; C8 column). The resultant salt was obtained by freeze-drying the appropriate fractions.

FAB-MS (M+1)$^+$416 (m/z); $^{13}C$ NMR (CD$_3$OD): δ 25.88, 27.24, 27.66, 57.76, 64.42, 66.18, 70.48, 81.93, 104.18, 115.40, 118.52, 133.84, 156.04, 162.12.

Example 42

7-(tert-Butyloxycarbonyl)-3-[3-(4-cyanophenoxy)-2-hydroxypropyl]-7-aza-3-azoniabicyclo[3.3.1 ]nonan-3-olate mCPBA (300 mg; 70%; 1.22 mmol) was added to a stirred solution of tert-butyl 7-[3-(4-cyanophenoxy)-2-hydroxypropyl]-3,7-diazabicyclo-[3.3.1]nonane-3-carboxylate (490 mg; 1.22 mmol; see Example 2 above) in DCM (10 mL) at 0° C. The reaction mixture was stirred for 1 h and then washed with NaHCO$_3$ (aq.). The organic layer separated, dried, concentrated and subjected to column chromatography (DCM:MeOH; 19:1) to give the title compound in a 98% yield.

FAB-MS (M+1)$^+$418 (m/z); $^{13}C$ NMR (CDCl$_3$): δ 27.63, 28.52, 46.16, 65.30, 68.45, 70.53, 72.03, 72.53, 78.98, 104.23, 115.28, 119.04, 133.96, 155.51, 161.68.

Example 43

7-(tert-Butyloxycarbonyl)-3-[(2S)-3-(4-cyanophenoxy)-2-hydroxypropyl]-7-aza-3-azoniabicyclo[3.3.1]nonan-3-olate The title compound was prepared in a 70% yield according to the method described in Example 42 above from 3,7-diazabicyclo[3.3.1]nonane-3-carboxylic acid, 7-[(2S)-3-(4-cyanophenoxy)-2-hydroxypropyl]-1,1-dimethylethyl ester (see Example 3 above).

FAB-MS (M+1)$^+$417 (m/z).

Example 44

7-(Cyclopentyloxycarbonyl)-3-[3-(4-cyanophenoxy)-2-hydroxypropyl]-7-aza-3-azoniabicyclo[3.3.1]nonane-3-olate The title compound was prepared in a 86% yield according to the method described in Example 42 above from cyclopentyl 7-[3-(4-cyanophenoxy)-2-hydroxypropyl]-3,7-diazabicyclo[3.3.1]nonane-3-carboxylate (see Example 9 above).

FAB-MS (M+1)$^+$430 (m/z); $^{13}$ C NMR (CDCl$_3$): δ 23.68, 27.41, 32.61, 45.80, 65.21, 68.29, 70.30, 72.17, 72.71, 77.60, 104.43, 115.10, 115.21, 118.95, 133.83, 134.11, 156.10, 161.45.

Example 45

7-(tert-Butyloxycarbonyl)-3-[3-(4-cyanophenoxy) propyl]-7-aza-3-azoniabicyclo[3.3.1]nonan-3-olate The title compound was prepared in a 80% yield according to the method described in Example 42 above from tert-butyl 7-(3-cyanophenoxypropyl)-3,7-diazabicyclo [3.3.1]nonane-3-carboxylate (see Example 21 above).

FAB-MS (M+1)$^+$402 (m/z); $^{13}C$ NMR (CDCl$_3$): δ 22.40, 27.12, 27.31, 28.50, 46.00, 66.04, 69.46, 70.58, 79.41, 104.23, 115.15, 119.05, 134.03, 155.54, 161.68.

Example 46

7-(tert-Butyloxycarbonyl)-3-[3-(4-cyanoanilino) propyl]-7-aza-3-azoniabicyclo[3.3.1]nonan-3-olate The title compound was prepared in a 6% yield according to the method described in Example 42 above from tert-butyl 7-[3-( 4-noanilino)propyl]-3,7-diazabicyclo[3.3.1] nonane-3-carboxylate (see Example 23 above).

AB-MS (M+1)$^+$401 (m/z); $^{13}C$ NMR (CDCl$_3$): δ 18.5, 22.3, 25.4, 27.3, 27.4, 28.6, 72.8, 79.2, 97.3, 112.1, 121.0, 133.6, 152.0, 155.5.

Example 47 n-Butyl 7-[3-(4-cyanophenoxy)-2-hydroxyprolyl]-3, 7-diazabicyclo[3.3.1]-nonane-3-carboxylate 4-[3-(3,7-Diazabicyclo[3.3.1]non-3-yl)-2-hydroxypropoxy]benzonitrile hydrochloride, (1 g; 2.96 mmol; see Example G above) was suspended in CH$_2$Cl$_2$ (20 mL) and saturated NaHCO$_3$ (40 mL). n-Butyl chloroformate was added (1.12 eq.; 3.33 mmol) and the reaction was stirred at room temperature overnight (18 to 20 h) under N$_2$. The crude material was chromatographed on a 3 cm×18 cm silica gel column eluting with hexanes:ethyl acetate (2:1). All fractions containing the desired material were combined to give 420 mg (1.20 mmol; 41% yield) of the title compound.

$^1$H NMR (CDCl$_3$): δ 7.58 (d, 2H), 6.95 (d, 2H), 4.40–3.90 (m, 8H), 3.30–2.85 (m, 4H), 2.60–1.20 (m, 12 H), 0.95 (t, 3H); $^{13}$C NMR (CDCl$_3$): δ 162.0, 157.5, 133.0, 119.0, 115.5, 104.0, 71.0, 70.5, 66.0, 65.5, 65.0, 62.5, 62.0, 61.0, 60.0, 58.0, 56.5, 49.5, 48.5, 33.0, 32.0, 31.0, 29.5, 29.0, 19.0, 13.5.

CI-MS (M+1)$^+$402 (m/z);

Example 48

2-Chloroethyl 7-[3-(4-cyanophenoxy)-2-hydroxypropyl]-3,7-diazabicyclo-[3.3.1]nonane-3-carboxylate Prepared according to the method described in Example 47 above using 2-chloroethyl chloroformate, yielding 783 mg (2.03 mmol; 69% yield) of the title compound.

$^1$H NMR (CDCl$_3$): δ 7.55 (d, 2H), 6.95 (d, 2H), 4.50–4.10 (m, 6H), 4.10–3.90 (m, 3H), 3.90–3.60 (m, 2H), 3.30–3.00 (m, 5H), 2.65–2.29 (m, 3H), 2.20–2.05 (m, 2H), 1.95–1.65 (m, 5H); $^{13}$C NMR (CDCl$_3$): δ 162.0, 134.0, 119.0, 115.5, 71.0, 70.5, 66.2, 65.0, 62.5, 62.0, 61.0, 60.0, 58.0, 56.5, 49.5, 48.5, 48.4, 43.0, 42.5, 32.7, 32.0, 29.5, 29.0;

CI-MS (M+1)$^+$408 (m/z); mp 104–105° C.

Example 49

Allyl 7-[3-(4-cyanophenoxy)-2-hydroxypropyl]-3,7-diazabicyclo[3.3.1]-nonane-3-carboxylate Prepared according to the method described in Example 47 above using allyl chloroformate, yielding 828 mg (2.15 mmol; 73% yield) of title compound.

$^{13}$H NMR (CDCl$_3$): δ 7.52–7.40 (d, 2H), 6.95–6.80 (d, 2H), 5.90–5.75 (m, 1H), 5.25–5.05 (m, 2H), 4.75–4.40 (m, 2H), 4.40–3.80 (m, 6H), 3.20-2.80 (m, 4H), 2.60–1.50 (m, 8H); $^{13}$C NMR (CDCl$_3$): δ 162.0, 134.0, 133.5, 119.0, 117.0, 115.0, 104.5, 71.0, 70.5, 66.0, 65.5, 62.5, 62.0, 60.0, 58.0, 57.0, 49.0, 48.0, 32.0, 31.5, 29.5; CI MS (M+1)$^+$386 (m/z).

Example 50 n-Propyl 7-[3-(4-cyanophenoxy)-2-hydroxypropyl]-3,7-diazabicyclo-[3.3.1]nonane-3-carboxylate Prepared according to the method described in Example 47 above using n-propyl chloroformate, yielding 780 mg (2.01 mmol; 68% yield) of the title compound.

$^1$H NMR (CDCl$_3$): δ 7.65–7.55 (d, 2H), 7.05–6.95 (d, 2H), 4.45–3.90 (m, 9H), 3.30–2.85 (m, 4H), 2.60–2.00 (m, 4H), 1.95–1.60 (m, 5H), 1.00–0.90 (t, 3H); $^{13}$C NMR (CDCl$_3$): δ 162.0, 134.0, 119.0, 117.0, 104.0, 71.5, 67.5, 65.5, 63.0, 61.5, 57.5, 49.5, 49.0, 33.0, 32.0, 29.5, 22.0, 11.0; Cl MS (M+1)$^+$388 (m/z).

Example 51

4-Nitrobenzyl 7-[3-(4-cyanophenoxy)-2-hydroxypropyl]-3,7-diazabicyclo-[3.3.1]nonane-3-carboxylate Prepared according to the method described in Example 47 above using 4-nitrobenzyl chloroformate, yielding 958 mg (2.00 mmol; 68% yield) of the title compound as a yellow crystalline solid.

$^1$H NMR (CDCl$_3$): δ 8.25–8.15 (d, 2H), 7.65–7.45 (m, 4H), 7.05–6.90 (d, 2H), 5.40–5.10 (m, 2H), 4.48–4.15 (m, 3H), 4.05–3.85 (m, 3H), 3.34–2.90 (m, 5H), 2.63–2.30 (m, 4H), 2.00–1.69 (m, 4H); $^{13}$C NMR (CDCl$_3$): δ 162.0, 144.5, 134.0, 128.0, 123.5, 119.0, 115.5, 71.5, 71.0, 66.1, 66.0, 65.0, 62.5, 62.0, 61.0, 60.05, 58.0, 56.5, 49.5, 49.0, 32.5, 31.8, 29.5, 29.0; CI MS (M+1)$^+$481 (m/z); mp 165–166° C.

Example 52

4-Fluorophenyl 7-[3-(4-cyanophenoxy)-2-hydroxypropyl]-3,7-diazabicyclo[3.3.1]-nonane-3-carboxylate Prepared according to the method described in Example 47 above using 4-fluorophenyl chloroformate, yielding 886 mg (2.02 mmol, 68% yield) of the title compound as a white crystalline solid.

$^1$H NMR (CDCl$_3$): δ 7.60–7.50 (m, 2H), 7.15–6.88 (m, 6H), 4.51–4.25 (m, 2H), 4.20–3.90 (m, 6H), 3.45–3.00 (m, 4H), 2.65–2.15 (m, 4H), 2.00–1.70 (m, 4H), 1.55 (s, 2H); $^{13}$C NMR (CDCl$_3$): δ 161.8, 147.5, 134.0, 123.5, 119.0, 116.0, 115.5, 71.0, 66.0, 65.5, 62.5, 61.8, 60.5, 58.5, 57.0, 50.0, 49.5, 49.0, 43.0, 32.5, 31.5, 29.5, 29.0; CI-MS (M+1)$^+$ 440 (m/z); mp 145–146° C.

Example 53

4-Methylphenyl 7-[3-(4-cyanophenoxy)-2-hydroxypropyl]-3,7-diaza-bicyclo[3.3.1]nonane-3-carboxylate Prepared according to the method described in Example 47 above using p-tolyl chloroformate, yielding 790 mg (1.81 mmol, 61% yield) of the title compound as a white crystalline solid.

$^1$H NMR (CDCl$_3$): δ 7.60–7.55 (m, 2H), 7.15–6.80 (m, 6H), 4.50–4.30 (m, 2H), 4.20–3.85 (m, 3H), 3.35–3.00 (m, 5H), 2.65–2.15 (m, 7H), 2.00–1.55 (m, 4H); $^{13}$C NMR (CDCl$_3$): δ 162.3, 134.6, 133.9, 133.2, 129.6, 121.5, 119.2, 115.5, 104.0, 70.9, 66.2, 65.5, 62.5, 61.6, 60.3, 59.9, 58.6, 57.3, 49.8, 48.8, 48.7, 32.3, 31.6, 29.5, 29.1, 20.8; CI-MS (M+1)$^+$436 (m/z); mp 125–126° C.

Example 54

4-Methoxyphenyl 7-[3-(4-cyanophenoxy)-2-hydroxypropyl]-3,7-diazabicyclo[3.3.1]nonane-3-carboxylate Prepared according to the method described in Example 47 above using 4-methoxyphenyl chloroformate yielding 655 mg (1.45 mmol; 49% yield) of the title compound as a fme white crystalline solid.

$^1$H NMR (CDCl$_3$): δ 7.60–7.45 (m, 2H), 7.10–6.70 (m, 6H), 4.55–4.20 (m, 3H), 4.20–3.85 (m, 4H), 3.75 (d, 3H), 3.60–3.00 (m, 4H), 2.75–1.60 (m, 7H); $^{13}$C NMR (CDCl$_3$): δ 162.5, 162.3, 157.1, 155.8, 154.8, 145.2, 134.1, 133.5, 123.5, 122.9, 119.4, 115.7, 114.4, 104.3, 71.1, 66.4, 65.7, 62.7, 61.8, 60.5, 60.3, 58.7, 55.8, 50.0, 49.4, 49.1, 32.5, 31.7, 29.8, 29.4 CI-MS (M+1)$^+$452 (m/z); mp 10–111° C.

Example 55

(−)Menthyl 7-[3-(4-cyanophenoxy)-2-hydroxyprolyl]-3,7-diazabicyclo-[3.3.1]nonane-3-carboxylate Prepared according to the method described in Example 47 above using (−)menthyl chloroformate, yielding 270 mg (0.56 mmol; 19% yield) of the title compound as a white crystalline solid.

$^1$H NMR (CDCl$_3$): δ 7.65–7.50 (d, 2H), 7.05–6.90 (t, 2H), 4.70–3.90 (m, 8H), 3.50–2.85 (m, 5H), 2.60–1.20 (m, 18H), 1.20–0.60 (m, 1H); $^{13}$C NMR (CDCl$_3$): δ 162.4, 157.4, 134.0, 119.3, 115.6, 104.1, 75.8, 74.9, 71.4, 71.1, 65.1, 64.9, 62.4, 60.3, 60.1, 56.7, 56.5, 49.7, 48.7, 48.4, 48.3, 47.6, 41.9, 41.5, 34.6, 32.9, 32.8, 31.4, 31.2, 29.7, 29.3, 26.4, 23.7, 23.3, 22.4, 22.2, 21.6, 21.1, 17.0, 16.7; CI-MS (M+1)$^+$484 (m/z); mp 111–112° C.

Example 56 neo-Pentyl 7-[3-(4-cyanophenoxy)-2-hydroxypropyl]-3,7-diazabicyclo-[3.3.1]nonane-3-carboxylate Prepared according to the method described in Example 47 above using neo-pentyl chloroformate, yielding 960 mg (2.31 mmol; 78% yield) of the title compound as a white crystalline solid.

$^1$H NMR (CDCl$_3$): δ 7.60–7.50 (d, 2H), 7.00–6.90 (d, 2H), 4.45–3.60 (m, 8H), 3.30–2.90 (m, 4H), 2.55–2.30 (m, 2H), 2.15–2.00 (m, 2H), 1.90–1.60 (m, 4H), 1.10–0.90 (s, 9H); $^{13}$C NMR (CDCl$_3$): δ 162.5, 158.1, 134.1, 119.4, 115.6, 104.3, 75.3, 71.1, 70.7, 66.8, 65.2, 62.9, 62.3, 60.9, 60.4, 58.5, 49.7, 49.0, 48.7, 33.1, 32.1, 31.7, 29.8, 29.6, 26.8; CI-MS (M+1)$^+$416 (m/z); mp 146–147° C.

Example 57

2-Methoxyethyl 7-[3-(4-cyanophenoxy)-2-hydroxypropyl]-3,7-diazabicyclo[3.3.1]nonane-3-carboxylate Prepared according to the method described in Example 47 above using 2-methoxyethyl chloroformate, yielding 420 mg (1.04 mmol, 35% yield) of the title compound as a pale yellow oil.

$^1$H NMR (CDCl$_3$): δ 7.60–7.50 (d, 2H0, 7.00–6.90 (d, 2H), 4.40–4.10 (m, 5H), 4.05–3.90 (m, 3H), 3.65–3.55 (m, 2H), 3.40–3.35 (s, 3H), 3.30–2.90 (m, 4H), 2.60–2.10 (m, 4H), 1.90–1.60 (m, 4H); $^{13}$C NMR (CDCl$_3$): δ 162.4, 157.6, 134.1, 133.4, 119.3, 115.5, 104.3, 71.2, 71.0, 70.7, 66.4, 65.3, 64.6, 62.7, 62.1, 60.8, 60.3, 58.9, 58.2, 56.9, 49.7, 48.9, 32.8, 31.9, 29.8, 29.7, 29.5; CI-MS (M+1)$^+$404 (m/z).

Example 58 tert-Butyl 7-[3-(4-tert-butylphenoxy)-2-hydroxypropyl]-3,7-diazabicyclo-[3.3.1nonane-3-carboxylate (a) 4-tert-Butyl-1-(2-oxiranylmethoxy)benzene A mixture of epichlorohydrin (15.3 g; 0.165 mol), 4-tert-butylphenol (5.0 g; 0.033 mol) and potassium carbonate (6.9 g; 0.050 mol) in acetonitrile (50 mL) was refluxed for 5 h. The resulting heterogeneous mixture was cooled to below reflux temperature and vacuum filtered through fritted glass. The organics were concentrated to give the crude product (7.9 g) as a liquid. Flash chromatography on silica gel (CH$_2$Cl$_2$:EtOAc; 19:1) gave the desired product (5.2 g; 76%) as a liquid.

$^1$H NMR (CDCl$_3$): δ 1.33 (s, 9H), 2.78 (m, 1H), 2.92 (t, 1H), 3.36 (m, 1H), 3.97 (dd, 1H), 4.21 (dd, 1H), 6.88 (d, 2H), 7.32 (d, 2H).

(b) tert-Butyl 7-[3-(4-tert-butylphenoxy)-2-hydroxypropyl]-3,7-diazabicyclo[3.3.1]nonane-3-carboxylate A mixture of tert-butyl-3,7-diazabicyclo[3.3.1]nonane-3-carboxylate (2.2 g; 9.70 mmol; see Example F above) and 4-tert-butyl-1-(2-oxiranylmethoxy)benzene (2.0 g; 9.70 mmol; from step (a) above) in 2-propanol (10 mL) and water (1 mL) was stirred at 60° C. for 18 h. The reaction mixture was concentrated to give an oil which was dissolved in hexanes and allowed to stand until solids formed. The solids were collected and dried to give the desired product (0.28 g; 7%) as a white solid.

mp 75–77° C.; $^1$H NMR (CDCl$_3$): δ 1.32 (s, 9H), 1.47 (s, 9H), 1.62–1.78 (m, 2H), 1.79–1.96 (m, 2H), 2.13–2.38 (m, 2H), 2.42–2.57 (m, 2H), 2.87–3.25 (m, 4H), 3.82–4.30 (m, 5H), 6.86 (d, 2H), 7.31 (d, 2H); $^{13}$C NMR (CDCl$_3$): δ 28.9, 29.1, 29.4, 29.7, 31.3, 31.7, 32.1, 34.3, 47.9, 48.1, 48.9, 49.6, 57.4, 58.1, 60.6, 61.9, 62.5, 65.5, 65.9, 70.7, 77.4, 79.7, 114.3, 126.4, 143.6, 155.8, 156.2, 156.8; CI-MS (M+1)$^+$433 (m/z).

Example 59 tert-Butyl 7-[3-(phenoxy)-2-hydroxypropyl]-3,7-diazabicyclo[3.3.1]-nonane-3-carboxylate (a) 1-(2-Oxiranylmethoxy)benzene Prepared according to the method described in Example 58(a) above using phenol (5.0 g; 0.053 mol), yielding 7.8 g (98%) of the sub-title compound as a liquid.

$^1$H NMR (CDCl$_3$): δ 2.77 (m, 1H), 2.90 (t, 1H), 3.37 (m, 1H), 3.98 (dd, 1H), 4.24 (dd, 1H), 6.87–7.03 (m, 3H), 7.22–7.35 (m, 2H).

(b) tert-Butyl 7-[3-(phenoxy)-2-hydroxypropyl]-3,7-diazabicyclo[3.3.1]-nonane-3-carboxylate Prepared according to the method described in Example 58(b) above from 1-(2-oxiranylmethoxy)benzene (2.0 g; 13.3 mmol; from step (a) above), yielding 2.4 g (48%) of the sub-title compound as a white solid.

mp 86–88° C.; $^1$H NMR (CDCl$_3$): δ 1.47 (s, 9H), 1.58–1.97 (m, 4H), 2.14–2.38 (m, 2H) 2.43–2.58 (m, 2H), 2.87–3.26 (m, 4H), 3.84–4.32 (m, 5H), 6.89–6.98 (m, 3H), 7.22–7.33 (m, 2H); $^{13}$C NMR (CDCl$_3$) δ 28.9, 29.1, 29.3, 29.6, 31.3, 32.1, 47.9, 48.8, 49.6, 57.4, 58.1, 60.5, 61.8, 62.3, 65.5, 65.8, 70.6, 79.6, 114.8, 120.9, 129.5, 155.6, 156.0, 159.1; CI-MS (M+1)$^+$377 (m/z).

Example 60 tert-Butyl-7-[3-(4-cyanophenoxy)-2-hydroxyprolyl]-9,9-dimethyl-3,7-diazabicyclo[3.3.1]nonane-3-carboxylate (a) Ethyl (2,2'-dimethylidene)cyanoacetate A mixture of acetone (30.8 g; 0.530 mol), ethyl cyanoacetate (50.0 g; 0.442 mol), ammonium acetate (6.80 g; 88.4 mmol), and glacial acetic acid (21.2 g; 0.354 mol) in benzene (100 mL) was heated under reflux for 9 h with azeotropic removal of water. The mixture was washed with water (3×50 mL), and the aqueous layer was extracted with ethyl acetate (50 mL). The combined organic extracts were dried over Na$_2$SO$_4$, and evaporated to an orange oil which was distilled under vacuum at 70–75° C. at 0.5 mm Hg to afford the sub-title compound (43.1 g; 64%) as a colourless liquid.

$^1$H NMR (CDCl$_3$) δ 4.20 (q, J=7.9 Hz, 2H), 2.33 (s, 3H), 2.25 (s, 3H), 1.30 (t, J=7.9 Hz, 3H).

(b) 1-Benzyl-3,5-dicyano-4,4-dimethyl-2,6-dioxopiperidone

Sodium metal (6.1 g; 0.264 mol) was added in pieces to absolute ethanol (375 mL) at 25° C. under nitrogen. After all the sodium had been dissolved, N-(cyanoacetyl) benzylamide (46.9 g; 0.270 mol; see Example 40(a) above) and ethyl (2,2'-dimethylidene)cyanoacetate (41.3 g; 0.270 mol; from step (a) above) were added sequentially. The dark orange mixture was stirred 3 days at 25° C., poured into water (300 mL), and concentrated hydrochloric acid (100 mL) was then added, following which a solid precipitated. The solid was collected via filtration over a sintered-glass funnel to yield the sub-title compound (39.5 g, 52%) as a tan solid.

mp 140–145° C.; $^1$H NMR (DMSO-d$_6$): δ 7.20–7.38 (m, 5H), 5.08 (s, 2H), 4.90 (s, 2H), 1.37 (s, 3H), 1.18 (s, 3H).

(c) 3-Benzyl-9,9-dimethyl-3,7-diazabicyclo[3.3.1]nonane-2,4,6,8-tetraone

A mixture of 1-benzyl-3,5-dicyano-4,4-dimethyl-2,6-dioxopiperidone (9.5 g; 43.5 mmol; from step (b) above) in phosphoric acid (50 mL) and sulfuric acid (50 mL) was heated at 120° C. for 1 h. The mixture was cooled and poured into ice-water (100 mL). The mixture was extracted with chloroform (3×100 mL), dried over Na$_2$SO$_4$, and evaporated to a white residue which was recrystallized from methanol to afford the sub-title compound (980 mg; 8%) as a white solid.

mp 243–245° C.; $^1$H NMR (CDCl$_3$): δ 7.22–7.37 (m, 3H), 7.10–7.18 (m, 2H), 4.82 (s, 2H), 3.83 (s, 2H), 1.12 (s, 3H), 1.08 (s, 3H).

(d) 3-Benzyl-9,9-dimethyl-3,7-diazabicyclo[3.3.1]nonane

A solution of 3-benzyl-9,9-dimethyl-3,7-diazabicyclo[3.3.1]nonane-2,4,6,8-tetraone (980 mg; 3.26 mmol; from step (c) above) in 1,4-dioxane (25 mL) was added dropwise to a suspension of lithium aluminium hydride (990 mg; 26.1 mmol) in 1,4-dioxane (30 mL) at 0° C. The mixture was refluxed overnight, cooled to 0° C. whereafter water (1.0 mL), 15% aqueous sodium hydroxide (1.0 mL), and more water (3.0 mL), were added sequentially. After stirring for 1 h at 0° C., the mixture was filtered through a small pad of Celite, washing the Celite cake with ethyl acetate (100 mL). The filtrate was evaporated to give the sub-title compound (676 mg; 85% crude yield) as a colourless oil which was used directly in the next step without further purification.

$^1$H NMR (CDCl$_3$): δ 7.15–7.38 (m, 5H), 3.52–3.80 (m, 2H), 3.40 (s, 2H), 3.18–3.30 (m, 2H), 2.53–2.89 (m, SH), 1.10–1.32 (m, 2H), 1.14 (s, 3H), 1.10 (s, 3H); $^{13}$C NMR (CDCl$_3$): δ 138.8, 128.6, 128.3, 126.9, 77.4, 63.6, 55.0, 48.5, 39.5, 26.8, 26.1; CI-MS (M+1)$^+$245 (m/z).

(e) tert-Butyl-7-benzyl-9,9-dimethyl-3,7-diazabicycl[3.3.1]nonane-3-carboxylate

A mixture of 3-benzyl-9,9-dimethyl-3,7-diazabicyclo[3.3.1]nonane (650 mg, 2.66 mmol; from step (d) above) and di-tert-butyl dicarbonate (580 mg; 2.66 mmol) in THF (8.0 mL) was stirred for 3 hours at 25° C. The mixture was evaporated to afford the sub-title compound (940 mg; 104% crude yield) as pale yellow oil which was used directly in the next step without further purification.

$^1$H NMR (CDCl$_3$): δ 7.18–7.40 (m, 5H), 3.84–3.96 (m, 2H), 3.66–3.77 (m, 1H), 3.35–3.60 (m, 4H), 2.57–2.75 (m, 4H), 1.50 (s, 9H), 1.25–1.43 (m, 2H), 1.08 (s, 6H); $^{13}$C NMR (CDCl$_3$): δ 6 173.8, 155.2, 139.4, 128.3, 128.1, 126.6, 78.7, 62.6, 55.4, 54.8, 46.5, 46.0, 38.5, 30.0, 28.7, 27.4, 25.6; CI-MS (M+1)$^+$345 (m/z).

(f) tert-Butyl-9,9-dimethyl-3,7-diazabicycl[3.3.1]nonane-3-carboxylate

A mixture of tert-butyl-7-benzyl-9,9-dimethyl-3,7-diazabicycl[3.3.1]-nonane-3-carboxylate (900 mg; 2.61 mmol; from step (e) above) and 10% palladium on carbon (w/w; 90 mg) in absolute ethanol (12 mL) was stirred overnight under 1 atmosphere of hydrogen. The catalyst was removed by filtration through a pad of Celite washing the Celite with ethyl acetate (50 mL). The filtrate was concentrated to an oil which was chromatographed on silica gel eluting with methanol:methylene chloride (1:10) to yield the sub-title compound (326 mg, 50%) as a pale yellow oil.

$^1$H NMR (CDCl$_3$): δ 3.68–3.83 (m, 2H), 3.37–3.48 (m, 2H), 3.15–3.29 (m, 2H), 2.80–2.90 (m, 2H), 2.56 (bs, 1H), 1.40 (s, 9H), 1.18–1.30 (m, 2H), 1.14 (s, 3H), 1.04 (s, 3H); $^{13}$C NMR (CDCl$_3$): δ 155.6, 79.7, 48.3, 37.8, 30.3, 28.5, 26.9, 25.7, 24.4; CI-MS (M+1)$^+$255 (m/z).

(g) tert-Butyl-7-[3-(4-cyanophenoxy)-2-hydroxyprolyl]-9,9-dimethyl-3,7-diazabicyclo[3.3.1]nonane-3-carboxylate A mixture of tert-butyl-9,9-dimethyl-3,7-diazabicycl[3.3.1]nonane-3-carboxylate (306 mg; 1.20 mmol; from step (f) above) and 4-(2-oxiranylmethoxy)benzonitrile (211 mg; 1.20 mmol; see Example A above) in isopropanol:water (2.0 mL; 9:1) was heated at 60° C. for 20 h. The mixture was concentrated to an oil which was partitioned with water (15 mL) and methylene chloride (2×20 mL). The organic layer was separated, dried over Na$_2$SO$_4$, and evaporated to an oil which was chromatographed on silica gel eluting with methylene chloride:methanol (98:2). Fractions containing the desired product were combined and concentrated to afford the title compound (220 mg; 43%) as a colourless oil.

$^1$H NMR (CDCl$_3$): δ 7.55 (d, J=9.7 Hz, 2H), 6.97 (d, J=9.7 Hz), 3.71–3.99 (m, 8H), 2.42–2.99 (m, 6H), 1.45–1.50 (m, 2H), 1.42 (s, 9H), 1.13 (s, 6H); $^{13}$C NMR (CDCl$_3$): δ 162.0, 155.5, 133.7,118.9, 115.3, 103.8, 79.1, 70.5, 65.2, 60.5, 60.0, 56.5, 53.8, 53.2, 46.3, 38.2, 38.0, 28.3, 25.8, 25.4; CI-MS (M+1)$^+$430 (m/z).

Example 61 tert-Butyl-7-[[3-(4-cyanophenoxy)-1,1-dimethyl-2-hydroxy]propyl]-3,7-diazabicyclo[3.3.1]nonane-3-carboxylate (a) 2,3-Oxiranyl-3-methyl-1-butanol mCPBA (56%; 33.75 g; 1.1 eq.) was added to a solution of 3-methyl-2-buten-1-ol (8.6 g; 100 mmol; 10.2 mL) in chloroform (500 mL) at 0° C., and the solution was stirred for 10 min. at 0° C. The reaction was then stirred at room temperature for 40 minutes, quenched with saturated K$_2$CO$_3$ solution (200 g) and stirred for 2 h. The organic layer was separated, dried over K$_2$CO$_3$ and concentrated in vacuo to give a clear, colourless oil (8.6 g, 84%). The oil was used immediately in the next step.

$^1$H NMR (CDCl$_3$): δ 3.87 (dd, 1H), 3.67 (dd, 1H), 3.00 (m, 1H), 1.37 (s, 3H), 1.32 (s, 3H).

(b) 2,3-Oxiranyl-3-methyl-1-butyl p-toluenesulfonate

A solution of tosyl chloride (20.7 g; 110 mmol) in CH$_2$Cl$_2$ (300 mL) was added dropwise to a 0° C. solution of 2,3-oxiranyl-3-methyl-1-butanol (8.60 g; 84.3 mmol; from step (a) above) and triethylamine (21 mL; 150 mmol) in CH$_2$Cl$_2$ (300 mL). The reaction was stirred at 0° C. for 1 h and stored in a freezer at –10° C. for 36 h. Intermittently, the reaction vessel was removed from the freezer, shaken and then placed back into the freezer. The reaction mixture was washed with brine (250 mL) and the CH$_2$Cl$_2$ layer was separated. The aqueous layer was extracted with CH$_2$Cl$_2$ (4×75 mL). The combined organic layers were dried over Na$_2$SO$_4$ and concentrated in vacuo to give an orange residue. The residue was subjected to column chromatography on silica gel eluting with a gradient of EtOAc in hexane (1:9 to 1:4). Fractions containing the desired compound were combined and concentrated to afford 21.34 g (98%) of a colourless oil.

$^1$H NMR (CDCl$_3$): δ 7.82 (d, 2H), 7.37 (d, 2H), 4.13 (m, 2H), 2.98 (m, 1H), 2.46 (s, 3H), 1.31 (s, 3H), 1.23 (s, 3H).

(c) 4-(3-Methyl-2,3-oxiranylbutoxy)benzonitrile

A solution of 4-cyanophenol (10.41 g; 87 mmol) in dry DMF (100 mL) was added dropwise to a suspension of sodium hydride (2.08 g; 87 mmol) in dry DMF (200 mL). The solution was stirred for 1 h at room temperature followed by the addition of a solution of 2,3-oxiranyl-3-methyl-1-butyl p-toluenesulfonate (21.34 g; 83 mmol; from step (b) above) in dry DMF (100 mL). The reaction was stirred at room temperature overnight. The reaction mixture was carefully poured into ice cold $H_2O$ (400 mL) followed by extraction with $CHCl_3$ (1×500 mL, 3×100 mL). The combined organic extracts were dried over $Na_2SO_4$ and concentrated in vacuo to afford an off white solid. The desired product was then isolated via crystallization from isopropyl ether (8.88 g, 53%).

$^1$H NMR (CDCl$_3$): δ 7.60 (d, 2H), 7.00 (d, 2H), 4.23 (dd, 1H), 4.09 (dd, 1H), 3.15 (m, 1H), 1.42 (s, 3H), 1.39 (s, 3H).

(d) tert-Butyl-7-[[3-(4-cyanophenoxy)-1,1-dimethyl-2-hydroxy]propyl]-3,7-diazabicyclo[3.3.1]nonane-3-carboxylate A mixture of 4-(3-methyl-2,3-oxiranylbutoxy)benzonitrile (0.956 g; 4.70 mol; from step (c) above) and tert-butyl-3,7-diazabicyclo[3.3.1]nonane-3-carboxylate (1.06 g; 4.70 mmol; see Example F) was refluxed in isopropanol:$H_2O$ (10:1; 10 mL) for 5 days. The reaction mixture was concentrated in vacuo. The residue was dissolved in $CH_2Cl_2$ (150 mL), washed with water (50 mL), brine (50 mL), dried over $Na_2SO_4$ and concentrated in vacuo to afford a light yellow oil. Purification via column chromatography on silica gel eluting with $CH_2Cl_2$:$CH_3OH$ (80:1) gave 0.540 g (27%) of the title compound.

$R_f$ 0.43 ($CH_2Cl_2$:$CH_{30}OH$ (25:1)); $^1$H NMR (CDCl$_3$) δ 7.61 (d, 2H), 6.98 (d, 2H), 3.88–4.62 (m,5H), 3.65 (brs, 1H), 2.89–3.33 (m, 6H), 2.78 (m, 2H), 1.66 (brs, 1H), 1.48 (s, 9H), 1.26 (s, 3H), 1.17 (s, 3H); CI-MS (M+1)$^+$430 (m/z).

Example 62 tert-Butyl 7-[3-(4-cyano-2-hydroxyphenoxy)propyl]-3,7-diazabicyclo-[3.3.1]nonane-3-carboxylate (a) 4-(3-Chloropropoxy)-3-hydroxybenzonitrile NaH (0.20 g; 8.14 mmol) was added to a room temperature solution of 3,4-dihydroxybenzonitrile (1.00 g; 7.40 mmol) in DMF. After stirring for 15 minutes, 1-bromo-3-chloropropane (1.3 g; 8.14 mmol) was added to the mixture. The reaction was stirred for 40 h at room temperature, and then quenched with water and extracted with EtOAc (100 mL). The EtOAc extract was washed with brine (4×100 mL), dried over $Na_2SO_4$ and concentrated in vacuo. The resulting crude product was chromatographed on a column of silica (5 cm×18 cm) eluting with a mixture of EtOAc and hexanes (1:4). Fractions containing the desired product were combined and concentrated in vacuo to afford the sub-title compound as an oil (0.5 g; 32%).

CI-MS (M+1)$^+$212 (m/z); $^1$H NMR (CDCl$_3$): δ 6 2.34 (m, 2H), 3.78 (t, 2H), 4.25 (t, 2H), 6.37 (br s, 1H), 6.92 (d, 1H), 7.17 (m, 2H).

(b) tert-Butyl 7-[3-(4-cyano-2-hydroxyphenoxy)propyl]-3,7-diazabicyclo-[3.3.1]nonane-3-carboxylate A solution of 4-(3-chloropropoxy)-3-hydroxybenzonitrile (0.50 g; 2.36 mmol; from step (a) above) and tert-butyl 3,7-diazabicyclo[3.3.1]nonane-3-carboxylate (0.80 g; 3.54 mmol; see Example F above) in acetonitrile (20 mL) was stirred for 20 h at 47° C. The reaction was concentrated in vacuo and the residue chromatographed on a column of silica (4 cm ×24 cm) eluting with a mixture of $CH_2Cl_2$ and $CH_3OH$ (98:2). After eluting 1 litre of the above eluant, the ratio of $CH_2Cl_2$ to $CH_3OH$ was changed to 95:5. Fractions containing the desired product were combined and concentrated in vacuo to afford 0.49 g of a semi-solid. This material was slurried with hexane to afford the title compound as an off white solid (0.40 g; 42%).

mp 127–130° C.; CI-MS (M+1)$^+$402 (m/z); $^1$H NMR (CDCl$_3$): δ 1.42 (s, 9H), 1.65 (br s, 2H), 1.92 (m, 4H), 2.25 (m, 4H), 3.01 (m, 4H), 4.12 (m, 4H), 6.91 (d, 1H), 7.18 (m, 2H); $^{13}$C NMR (CDCl$_3$): δ 26.2, 28.5, 31.2, 47.9, 49.2, 55.1, 58.2, 59.1, 67.5, 79.6, 104.2, 102.5, 118.2, 119.5, 125.3, 146.8, 150.5, 155.8.

Example 63 tert-Butyl 7-[4-(4-cyanophenyl)-2-hydroxybutyl]-3,7-diazabicyclo[3.3.1]-nonane-3-carboxylate (a) 4-(3-Butenyl)benzonitrile ZnCl$_2$ (15.0 g; 110 mmol) was heated with a blow torch under vacuum until fused for about 20 min. After cooling to room temperature, magnesium turnings (2.7 g; 110 mmol) were added and heated again until ZnCl$_2$ was partially fused again (ca. 5 min). The mixture was cooled to room temperature, placed under $N_2$ and dry THF (100 mL) was added. 4-Bromo-1-butene (11.0 mL; 110 mmol) was then added and the mixture was treated with sonication and warming for 2 h followed by stirring at room temperature for 1.5 days. Pd(Ph$_3$P)$_4$ (6.00 g; 5.19 mmol) in THF (60 mL) was added to this mixture, followed by 4-bromobenzonitrile (20.0 g; 110 mmol) in THF (100 mL). The mixture was stirred for 24 h at room temperature. The reaction was quenched by the addition of 3N HCl (500 mL) and extracted with ether (2×400 mL). The organic layer was dried over MgSO$_4$, filtered and evaporated to give 20.1 g of an oil/solid mixture. The residue was purified on a wet-packed silica gel column (6.5×40 cm; 10% EtOAc/Hex) eluting with 10% EtOAc/hexanes. After a 500 mL forerun, 200 mL fractions were collected. Fractions 3–6 were combined and evaporated to give 13.6 g (79%) of a clear semi-solid.

Analysis by $^1$H NMR showed the sub-title product and 4-bromobenzonitrile (in a 2.2/1 ratio (approximately)). This material was used directly in the next step.

(b) 4-(3-Oxiranylbutyl)benzonitrile mCPBA (49.0 g; 288 mmol) was added to a solution of the product from step (a) above; 13.6 g; 57.7 mmol) in $CH_2Cl_2$ (550 mL). The solution was stirred at room temperature for 2 days. To this solution was added $CH_2Cl_2$ (200 mL) and the organic layer was washed with saturated NaHCO$_3$ (500 mL), 10% $Na_2S_2O_3$ (2×400 mL), saturated NaHCO$_3$ (400 mL) and brine (200 mL). The organic layer was then dried over MgSO$_4$, filtered and evaporated to give 13.9 g of a semi-solid. Analysis by $^1$H NMR showed the presence of the sub-title product and 4-bromobenzonitrile. This material was used directly in the next step.

(c) tert-Butyl 7-[4-(4-cyanophenyl)-2-hydroxybutyll-3,7-diazabicyclo-[3.3.1]nonane-3-carboxylate The product mixture from step (b) above (400 mg; 2.31 mmol) was heated in the presence of tert-butyl 3,7-diazabicyclo[3.3.1]nonane-3-carboxylate (374 mg; 1.65 mmol; see Example F above) in 2-propanol (5 mL) at 60° C. for 7 h. The solution was stirred at room temperature for 2 days. The solvent was evaporated and the residue chromatographed on a wet-packed silica gel column (3.5×24 cm, 1:1 EtOAc/hexane) eluting with EtOAc:hexane (1:1). After a 50 mL forerun, 15 mL fractions were collected. Fractions 66–70 were combined and evaporated to give 433 mg (66%) of the title product as an off-white solid.

mp 88–93° C.; CI-MS (M+1)$^+$400 (m/z); $^1$H NMR (CDCl$_3$): δ 8 7.56 (d, J=8.2 Hz, 2 H), 7.31 (d, J=8.2 Hz, 2 H), 3.99–4.25 (m, 2 H), 3.60–3.69 (m, 1 H), 3.5 (br s, 1 H), 2.69–3.15 (m, 6 H), 2.47 (m, 1 H), 1.75–2.4 (m, 6 H), 1.54–1.72 (m, 3 H) 1.47 (s, 9 H); $^{13}$C NMR (CDCl$_3$): δ 148.5, 132.3, 129.5, 119.3, 109.7, 79.6, 65.6, 65.2, 60.7, 57.7, 57.1, 49.5, 48.8, 47.8, 36.2, 32.2, 32.1, 31.4, 29.6, 29.0, 28.9.

Example 64 tert-Butyl 7-[4-(4-cyanophenoxy)-2-hydroxybutyl]-3,7-diazabicyclo[3.3.1]-nonane-3-carboxylate (a) 4-(2-Oxiranylethoxy)benzonitrile mCPBA (15.9 g; 65 mmol) was added to a stirred solution of 4-(4'-cyanophenoxy)but-1-ene (7.5 g; 56 mmol; prepared according to the method described in J. Chem. Soc. Perkin Trans. 1, 9 (1992) 1145–1148) in $CH_2Cl_2$ (175 mL) and the reaction mixture was stirred at room temperature for 4 h. The reaction mixture was washed with $NaHCO_3$ (aq.) and the organic layer separated, dried and concentrated to give the sub-title compound (7.23 g; 38 mmol).

(b) tert-Butyl 7-[4-(4-cyanophenoxy)-2-hydroxybutyl] -3,7-diazabicyclo-[3.3.1]nonane-3-carboxylate 4-(2-Oxiranylethoxy)benzonitrile (0.946 g; 5.0 mmol; from step (a) above) was added to a stirred solution of tert-butyl 3,7-diazabicyclo[3.3.1]nonane-3-carboxylate (1.13 g; 5.0 mmol; see Example F above) in MeCN (50 mL) and the reaction mixture was stirred at 75° C. for 72 h. The reaction mixture was concentrated and the residue subjected to column chromatography ($CH_2Cl_2$:MeOH; 15: 1) to give the title compound in a 88% yield (1.84 g; 4.42 mmol).

FAB-MS $(M+1)^+416$ (m/z); $^{13}C$ NMR ($CDCl_3$): δ 28.74, 29.53, 32.22, 34.31, 47.13, 49.44, 56.92, 60.45, 62.89, 65.38, 79.96, 104.01, 115.22, 119.36, 134.03, 156.06, 162.41.

Example 65 tert-Butyl 7-{3-[(4-cyanophenyl)thio]-2-hydroxypropyl}-3,7-diazabicyclo-[3.3.1]nonane-3-carboxylate The title compound was prepared according to the procedure described in Example 64 above using (4-cyanophenylsulfonylmethyl)oxirane (prepared according to the method described in Example A above from p-cyanothiophenol).

FAB-MS: $(M+1)^+418$ (m/z); $^{13}C$ NMR ($CDCl_3$): δ 29.79, 30.54, 33.10, 37.80, 48.70, 50.52, 58.05, 59.07, 61.32, 65.12, 66.36, 80.66, 109.24, 120.03, 128.08, 133.18, 146.14, 156.93.

Example 66 tert-Butyl 7-[4-(4-cyanophenoxy)-2-butenyl]-3,7-diazabicyclo[3.3.1]-nonane-3-carboxylate (a) 4-(4-Cyanophenoxy)-1-chloro-2-butene 1,4-Dichlorobutene (750 g; 5 mol) was added to a stirred suspension of 4-cyanophenol (119.12 g; 1 mol) and $K_2CO_3$ (345 g; 2.5 mol) in MeCN (1000 mL) and the reaction mixture was refluxed for 4 h. The reaction mixture was filtered and concentrated. The residue was dissolved in di-iso-propyl ether (2000 mL) and after 24 h the precipitate was filtered off. The filtrate was concentrated giving the sub-title compound as a yellow oil which solidified upon standing (186 g; 0.89 mol).

(b) tert-Butyl 7-[4-(4-cyanophenoxy)-2-butenyl]-3,7-diazabicyclo[3.3.1]-nonane-3-carboxylate tert-Butyl 3,7-diazabicyclo[3.3.1]nonane-3-carboxylate (1.13 g; 5 mmol; see Example F above) was added to a stirred solution of 4-(4-cyanophenoxy)-1-chloro-2-butene (1.04 g; 5 mmol; from step (a) above) in MeCN (25 mL) and the reaction mixture was stirred at room temperature overnight. The reaction mixture was concentrated and partitioned between diethyl ether and $KHSO_4$ (0.3 M). The aqueous layer was treated with NaOH (2M) and subsequently extracted with $CH_2Cl_2$. The organic layer was washed with water, dried, concentrated and purified using column chromatography ($CH_2Cl_2$:MeOH; 95:5) to give the title compound (0.84 g; 2.1 mmol).

$^{13}C$ NMR ($CDCl_3$): δ 28.75, 32.18, 47.90, 49.04, 58.19, 59.05, 60.76, 68.77, 78.49, 103.93, 115.65, 119.37, 125.66, 133.95, 155.39, 161.96.

Example 67 tert-Butyl 7-{2-[2-(4-cyanophenoxy)ethoxy]ethyl}-3,7-diazabicyclo-[3.3.1]nonane-3-carboxylate (a) 4-(2-Bromoethoxy)benzonitrile The sub-title compound was prepared according to the method described in J. Chem. Soc., (1942) 103, 114, but using $K_2CO_3$ as the base.

(b) 2-(4-Cyanophenoxy)ethoxy]ethanol

Ethylene glycol (12 mL, 220 mmol) was added to a suspension of NaH (2.8 g; 66 mmol) in DMF (10 mL) and the reaction mixture was stirred for 10 minutes. 4-(2-Bromoethoxy)benzonitrile (5 g; 22 mmol; from step (a) above) was added and the reaction mixture was stirred at 80° C. for 3 h and then overnight at room temperature. The reaction mixture was filtered and subjected to column chromatography (hexane:EtOAc; 1:1) giving the sub-title compound in 50% yield.

(c) tert-Butyl 7-{2-[2-(4-cyanophenoxy)ethoxy]ethyl}-3,7-diazabicyclo-3.3.1]nonane-3-carboxylate Mesylchloride (2.9 g; 29 mmol) was added to a stirred −5° C. solution of 2-(4-cyanophenoxy)ethoxy]ethanol (5.0 g; 24 mmol; from step (b) above) in $CH_2Cl_2$ (50 mL) and the reaction mixture was stirred at room temperature for 2 h. The reaction mixture was washed with $H_2O$ and the organic layer separated, dried and concentrated. Part of the oily residue (2.0 g; 7 mmol) was dissolved in MeCN (50 mL) and $K_2CO_3$ (1.5 g; 10.5 mmol) and tert-butyl 3,7-diazabicyclo[3.3.1] nonane-3-carboxylate (1.6 g; 7.0 mmol; see Example F above) were added. The suspension was refluxed overnight and the salts were filtered off. The filtrate was concentrated and purified using column chromatography (EtOAc) giving the title compound (1.0 g; 2.4 mmol).

ESI-MS $(M+1)^+417$ (m/z); $^{13}C$ NMR ($CDCl_3$): δ 28.66, 29.13, 31.54, 47.74, 48.88, 58.15, 58.72, 59.54, 67.73, 69.07, 69.90, 78.51, 104.01, 115.35, 119.24, 133.93, 155.2.

Example 68 tert-Butyl 7-[4-(4-cyanophenyl)butyl]-3,7-diazabicyclo[3.3.1]nonane-3-carboxylate (a) 2-[2-(4-Cyanophenoxy)ethyl]malonic acid dimethyl ether NaH (3.05 g; 127 mmol) was added at 0° C. to a stirred solution of malonic acid dimethyl ester (17 g; 129 mmol) in MeCN (225 mL). A solution of 4-cyanophenethyl methanesulfonate (9.7 g; 43.1 mmol; see Example 25(a) above) in MeCN (50 mL) was added and the reaction mixture was refluxed overnight. $NaHCO_3$ (3 g) was added and the slurry was filtered and concentrated. The residue was partitioned between diethyl ether and $H_2O$ and the organic layer was separated, dried and concentrated. The residue was purified using column chromatography (toluene:di-iso-propyl ether; 1:3) giving the sub-title compound (14.6 g; contaminated with malonic acid dimethyl ester). This product was used directly in the next step without further purification.

(b) 4-(4-Cyanophenoxy)butyric acid methyl ester

A mixture of 2-[2-(4-cyanophenoxy)ethyl]malonic acid dimethyl ether (11.07 g; 42.4 mmol; from step (a) above), NaCl (2.64 g; 45 mmol), $H_2O$ (1.62 g; 90 mmol) and DMSO (35 mL) was refluxed for 36 h. H₂O (400 mL) was added and the mixture was extracted with diethyl ether. The organic layer was washed with H₂O, dried and concentrated. Purification using column chromatography (toluene:di-isopropyl ether; 1:3) gave the sub-title compound (5.04 g; 24.8 mmol).

(c) 4-(4-Cyanophenoxy)-1-butanol

LiBH₄ (1.5 g; 71.1 mmol) was added to a stirred solution of 4-(4-cyanophenoxy)butyric acid methyl ester (9.63 g; 47.4 mmol; from step (b) above), MeOH (2.87 mL; 71.1 mmol) and diethyl ether (158 mL) and the reaction mixture was refluxed overnight. The ether phase was collected and the residue was extracted with diethyl ether (3×50 mL). The combined organic phase was dried, concentrated and purified using column chromatography (EtOAc:hexane; 1:3) to give the sub-title compound (3.82 g; 21.8 mmol).

(d) Methanesulfonic acid 4-(4-cyanophenoxy)-butyl ester

Mesylchloride (2.32 mL; 30 mmol) was added to a stirred 0° C. solution of 4-(4-cyanophenoxy)-1-butanol (5.2 g; 29.7 mmol; from step (c) above) and TEA (4.35 mL) in CH₂Cl₂ (50 mL), and the reaction mixture was stirred for 4 h. H₂O (150 mL) was added and the organic layer separated, dried and concentrated to give the sub-title compound which was used without further purification.

(e) tert-Butyl 7-[4-(4-cyanophenyl)butyl]-3,7-diazabicyclo[3.3.1]nonane-3-carboxylate The title compound was prepared in 73% yield from methanesulfonic acid 4-(4-cyanophenoxy)-butyl ester and tert-butyl 3,7-diazabicyclo[3.3.1]-nonane-3-carboxylate (from step (d) above) according to the method described in Example 25(b) above.

¹³C NMR (CDCl₃): δ 26.23, 28.72, 29.09, 31.56, 36.01, 47.67, 48.72, 58.31, 58.81, 59.19, 78.39, 109.38, 119.19, 129.17, 129.42, 131.91, 132.16, 148.41, 155.05.

Example 69

7-[2-(4-Cyanophenoxy)ethyl]-3,7-diazabicyclo[3.3.1]nonane-3-carboxylic acid tert-butyl ester tert-Butyl-3,7-diazabicyclo[3.3.1]nonane-3-carboxylate (3.62 g; 16 mmol; see Example F above) was added to added to a stirred solution of 4-(2-bromoethoxy)benzonitrile (3.62g; 16 mmol; see Example 67(a) above) and TEA (3.34 mL; 24 mmol) in MeCN (70 mL) and the reaction mixture was stirred at 60° C. overnight and then stored at room temperature for 48 h. The solids were filtered off, washed with IPA (2×100 mL) and the filtrate concentrated. The residue was partitioned between DCM and NaHCO₃ (sat.), the organic layer was separated, dried (MgSO₄) and concentrated. The oily residue was subjected to column chromatography (DCM:MeOH; 25:1) to give the title compound in a 72% yield.

¹³C NMR (CDCl₃): δ 29.73, 30.25, 30.44, 32.73, 48.83, 50.00, 58.24, 59.71, 60.48, 68.04, 79.67, 104.48, 116.37, 120.65, 135.04, 156.35, 163.23.

Example 70

Methyl 7-[3-(4-cyanophenoxy)-2-hydroxypropyl]-3,7-diazabicyclo[3.3.1]-nonane-3-carboxylate The title compound was prepared according to the method described in Example 1 above, starting with methylchloroformate.

Example 71

7-[2-(4-Cyanophenoxy)-2-hydroxyprolyl]-3,7-diazabicyclo[3.3.1]-nonane-3-carboxylic acid 1-tert-butoxycarbonyl-piperidine-4-yl ester N-(tert-Butyloxycarbonyl)-4-piperidinol (470 mg; 2.3 mmol; see Tetrahedron Lett.; 37; 36 (1996) 6439–6442) was added to a stirred solution of carbonyl diimidazole (379 mg; 2.3 mmol) in MeCN, and the reaction mixture was stirred for 48 h. 4-[3-(3,7-Diazabicyclo[3.3.1]non-3-yl)-2-hydroxypropoxylbenzonitrile (692 mg; 2.3 mmol; see Example G above) was added in one portion and the reaction mixture was refluxed for 2 h. The solvent was removed on a rotary evaporator and the residue partitioned between DCM and NaHCO₃ (sat.). The organic layer was collected, dried, concentrated and purified using column chromatography (DCM:MeOH; 25:1) to give the title compound in a 74% yield.

¹³C NMR (CDCl₃): δ 29.51, 30.23, 30.52, 32.05, 33.75, 49.66, 50.60, 54.53, 57.56, 59.45, 61.26, 61.84, 62.56, 63.47, 65.98, 67.27, 71.04, 71.51, 71.92, 80.59, 106.52, 116.42, 120.25, 134.98, 155.84, 157.74, 163.26; FAB-MS: (M+1)⁺529.1 (m/z).

Example 72

7-[3-(4-Cyanophenoxy)-2(S)-hydroxypropyl]-3,7-diazabicyclo[3.3.1]-nonane-3-carboxylic acid cyclopropylmethyl ester A cooled solution of cyclopropanemethanol (1.8 g; 25 mmol) in THF (7 mL) was added to a stirred 0C dispersion of CDI (4.05 g; 25 mmol) in THF (15 mL), and the reaction mixture was stirred for 30 minutes. A fraction of this solution (3.75 mL; 4.35 mmol) was added to a dispersion of 4-[3-(3,7-diazabicyclo[3.3.1]non-3-yl)-2(S)-hydroxypropoxy)benzonitrile (2.25 g; 6.0 mmol; dihydrochloride salt; prepared from 3,7-diazabicyclo[3.3.1]nonane-3-carboxylic acid and 7-[(2S)-3-(4-cyanophenoxy)-2-hydroxypropyl]-1,1-dimethylethyl ester, analogously to the method described in Example G above) and K₂CO₃ (2.0 g; 14.5 mmol) in THF (10 mL). The reaction mixture was heated (85° C.) in a sealed steel vessel for 24 hours, was then concentrated, and the residue partitioned between DCM and water. The organic layer was collected, dried, concentrated and subjected to column chromatography (DCM:MeOH; 95:5) to give the title compound in a 29% yield.

FAB-MS (M+l)⁺400.0 (m/z).

Example 73

7-[3-(4-Cyanophenoxy)-2-hydroxypropyl]-3,7-diazabicyclo[3.3.1]nonane-3-carboxylic acid 2-(4-acetylpiperazin-1-yl) ethyl ester (a) 1-[4-(2-Hydroxyethyl)piperazin-1-yl]ethanone Acetic acid anhydride (5.1 g; 50 mmol) was added to a stirred solution of N-(2-hydroxyethyl)piperazine (6.5 g; 50 mmol) in DCM (5 mL). The reaction mixture was stirred until the exothermic reaction was complete. The solvent was evaporated and the residue co-evaporated with toluene. The crude sub-title compound was used without further purification.

(b) 7-[3-(4-Cyanophenoxy)-2-hydroxyprolyl]-3,7-diazabicyclo[3.3.1]-nonane-3-carboxylic acid 2-(4-acetylpiperazin-1-yl) ethyl ester A solution of CDI (0.5 g; 3.1 mmol) in DCM (20 mL) was added to a stirred solution of 1-[4-(2-hydroxyethyl)-piperazin-1-yl]ethanone (0.5 g; 2.9 mmol; from step (a) above) in DCM (5 mL), and the reaction mixture was stirred for 1 hour. Water was added and the organic layer collected, dried and concentrated to give the imidazolide in a 80% yield. A solution of 4-[3-(3,7-diazabicyclo[3.3.1 ]non-3-yl)-2-hydroxypropoxy]benzonitrile (375 mg; 1.25 mmol; see Example G above) in MeCN (25 mL) was added to a portion of the imidazolide (333 mg; 1.25 mmol) and KCO₃ (s) in MeCN (10 mL), and the reaction mixture was stirred for 15 hours. The olvent was removed on a rotary evaporator and the residue partitioned between DCM and water. The organic layer was collected, dried, concentrated and subjected to column chromatography (DCM:MeOH; 95:5) to give the title compound in a 35% yield.

FAB-MS (M+l)$^+$499.4 (m/z).

Example 74

7-[3-(4-Cyanophenoxy)-2-hydroxy-2-hydroxymethylpropyl]-3,7-diazabicyclo[3.3.1]nonane-3-carboxylic acid tert-butyl ester (a) 4-(2-Chloromethylallyloxy)benzonitrile A solution of 4-cyanophenol (11.9 g; 0.1 mol) in 1,2-dimethoxyethane (100 mL) was slowly added to a stirred and cooled (0° C.) suspension of NaH (4.0 g; 0.1 mol; 55% dispersion) in 1,2-dimethoxyethane (250 mL). The reaction mixture was refluxed for 1 hour and then allowed to cool to room temperature. 3-Chloro-2-chloromethyl-propene (20 g; 0.16 mol) was added in one portion and the reaction mixture was stirred at 45° C. for 40 hours. The reaction mixture was partitioned between DCM and NaHCO$_3$ (satd.) and the organic layer collected, dried, concentrated and purified using column chromatography (DCM:MeOH; 50:1) to give the sub-title ompound in a 66% yield.

(b) 4-(3-Chloro-2-hydroxy-2-hydroxymethylpropoxy) benzonitrile

N-Methyl morpholine N-oxide (490 mg; 3.64 mmol) and osmium tetroxide (80 μL; 4 wt. % solution in water) were added to a stirred solution of 4-(2-chloromethylallyloxy) benzonitrile (630 mg; 3.0 mmol; from step (a) above) in 10 mL wet acetone (12% H$_2$O). The reaction mixture was stirred at room temperature for 36 hours. Na$_2$SO$_3$ (1.0 g) was added and after 1 hour the solids where filtered off. The filtrate was concentrated and the residue subjected to column chromatography (DCM:MeOH; 50:1) to give the sub-title compound in a 50% yield.

(c) 7-[3-(4-Cyanophenoxy)-2-hydroxy-2-hydroxymethylpropyl]-3,7-diazabicyclo[3.3.1]nonane-3-carboxylic acid tert-butyl ester A mixture of 4-(3-chloro-2-hydroxy-2-hydroxymethylpropoxy)benzonitrile (180 mg; 0.74 mmol; from step (b) above), tert-butyl 3,7-diazabicyclo-[3.3.1]nonane-3-carboxylate (230 mg; 1.0 mmol; see Example F above) and K$_2$CO$_3$ (140 mg; 1.0 mmol) in MeCN (5 mL) was refluxed for 48 hours. The reaction mixture was filtered and the filtrate concentrated. The residue was dissolved in diethyl ether and the solution was acidified with KHSO$_4$ (aq.). The aqueous layer was collected and NaHCO$_3$ (satd.) was added followed by ether extraction. The organic layer was collected, dried, concentrated and subjected to column chromatography (DCM:MeOH; 20:1) to give the title compound in a 31% yield.

$^{13}$C NMR in D$_2$O (MeOH as internal standard): δ 28.49, 29.05, 30.46, 47.81, 48.55, 60.25, 60.94, 61.19, 65.15, 69.41, 70.08, 72.93, 79.78, 104.13, 115.31, 119.03, 133.91, 154.98, 161.72; FAB-MS (M+1)$^+$431.7 (m/z).

Example 75

The title compounds of the aboveExamples 1 to 74 were tested in Test A above and were all found to exhibit an D$_{10}$ value of more than 6.0.

Abbreviations

AcOH=acetic acid

ADDP=1,1'-(azodicarbonyl)piperidine aq.=aqueous atm.=atmospheres

CBz=benzyloxycarbonyl

CDI=carbonyl diimidazole

Bu=butyl

DCM=dichloromethane

DMF=dimethylformamide

DMSO=dimethylsulfoxide

Et=ethyl

EtOAc=ethyl acetate

EtOH=ethanol

ESI=electron spray interface eq.=equivalents

FAB=fast atom bombardment h=hours

IPA=iso-propanol i-PrOH=iso-propanol

LC=liquid chromatography

HPLC=high performance liquid chromatography mCPBA=meta-chloroperbenzoic acid

Me=methyl

MeCN=acetonitrile

MeOH=methanol mesyl=methanesulfonate min.=minutes

Ms=mesylate

MS=mass spectroscopy

NADPH=nicotinamide adenine dinucleotide phosphate, reduced form

NMR=nuclear magnetic resonance

OSu=O-succinyl

Pd/C=palladium on carbon pTSA=para-toluenesulfonic acid rt.=room temperature satd.=saturated TEA=triethylamine THF=tetrahydrofuran tlc=thin layer chromatography TMS=tetramethylsilane Prefixes n, s, i and t have their usual meanings: normal, iso, secondary and tertiary.

What is claimed is:

1. A compound of the formula (I)

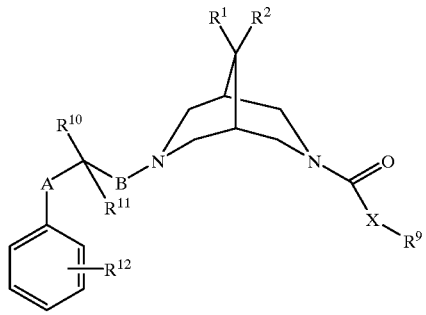

wherein
- $R^1$ and $R^2$ independently represent H, $C_{1-4}$ alkyl or together form —O—(CH$_2$)$_2$—O—, —(CH$_2$)$_4$— or (CH$_2$)$_5$—;
- $R^9$ represents $C_{1-12}$ alkyl, phenyl, naphthyl, $C_{1-3}$ alkylphenyl (which four groups are all optionally substituted or terminated by one or more substituents selected from the group consisting of —OH, halo, cyano, nitro, $C_{1-4}$ alkyl or $C_{1-4}$ alkoxy) or —(CH$_2$)$_q$Cy$^1$;
- $R^{10}$ represents H or —OH;
- $R^{11}$ represents H or $C_{1-4}$ alkyl;
- $R^{12}$ represents one or more optional substituents selected from OH, cyano, halo, amino, nitro, $C_{1-6}$alkyl, $C_{1-6}$alkoxy, —N(H)S(O)$_2$R$^{16}$, OS(O)$_2$R$^{16a}$, —N(H)C(O)N(H)R$^{17}$ or —C(O)N(H)R$^{18}$;
- A represents a single bond, $C_{1-4}$ alkylene, —(CH$_2$)$_n$N(R$^{20}$)—, —(CH$_2$)$_n$S(O)$_p$—, —(CH$_2$)$_n$O— (in which three latter groups, the —(CH$_2$)$_n$— group is attached to the carbon atom bearing $R^{10}$ and $R^{11}$), —C(O)N(R$^{20}$)— (in which latter group, the —C(O)— group is attached to the carbon atom bearing $R^{10}$ and $R^{11}$), —N(R$^{20}$)C(O)O(CH$_2$)$_n$—, —N(R$^{20}$)(CH$_2$)$_n$— (in which two latter groups, the N(R$^{20}$) group is attached to the carbon atom bearing $R^{10}$ and $R^{11}$) or —(CH$_2$)$_m$C(H)(OH)(CH$_2$)$_n$— (in which latter group, the —(CH$_2$)$_m$— group is attached to the carbon atom bearing $R^{10}$ and $R^{11}$);
- B represents a single bond, $C_{1-6}$ alkylene, —N(R$^{23}$)(CH$_2$)$_r$— or —O(CH$_2$)$_r$— (in which two latter groups, the —(CH$_2$)$_r$ group is attached to the bispidine nitrogen atom);
- m represents 1, 2 or 3;
- n and r independently represent 0, 1, 2, 3 or 4;
- p represents 0, 1 or 2;
- q represents 0; 1, 2 or 3;
- X represents O or S;
- Cy$^1$ represents a five to seven-membered heterocyclic ring containing one or more heteroatom selected from O, N or S, which ring is optionally substituted by one or more substituent selected from C(O)R$^{21}$ or C(O)OR$^{22}$;
- $R^{16}$, $R^{16a}$, $R^{20}$ and $R^{23}$ independently represent H or $C_{1-4}$ alkyl; and
- $R^{17}$, $R^{18}$, $R^{21}$ and $R^{22}$ independently represent H or $C_{1-6}$ alkyl;
- with the proviso that when $R^9$ is phenyl, and $R^{10}$ and $R^{11}$ are hydrogen, both A and B are not single bonds;

or a pharmaceutically acceptable derivative thereof.

2. A compound as claimed in claim 1, wherein $R^1$ represents H, $C_{1-4}$ alkyl or, together with $R^2$, represents —O(CH$_2$)$_2$O— or —(CH$_2$)$_4$—.

3. A compound as claimed in claim 1, wherein $R^2$ represents H or, together with $R^1$, represents —O(CH$_2$)$_2$O— or —(CH$_2$)$_4$—.

4. A compound as claimed in claim 1, wherein R9 represents optionally substituted phenyl, optionally substituted $C_{1-3}$ alkylphenyl, optionally substituted, optionally unsaturated, linear, branched or cyclic, $C_{1-12}$ alkyl (which latter group may also be interrupted by an O atom), or —(CH$_2$)$_q$Cy$^1$.

5. A compound as claimed in claim 4, wherein $R^9$ represents linear or branched $C_{2-7}$ alkyl.

6. A compound as claimed in claim 1, wherein $R^{10}$ represents —OH.

7. A compound as claimed in claim 1, wherein $R^{11}$ represents H, CH$_3$ or CH$_2$OH.

8. A compound as claimed in claim 1, wherein $R^{12}$ is absent or represents one or more substituents selected from cyano, OH, nitro, N(H)SO$_2$R$^{16}$, N(H)C(O)N(H)R$^{17}$, C(O)N(H)R$^{18}$, OS(O)$_2$R$^{16a}$, amino and $C_{1-6}$ alkyl.

9. A compound as claimed in claim 8, wherein, when $R^{12}$ is in the para-position, it represents cyano, nitro or N(H)S(O)$_2$R$^{16}$ (in which R$^{16}$ represents $C_{1-3}$ alkyl).

10. A compound as claimed in claims 1, wherein X represents O.

11. A compound as claimed in claim 1, wherein A represents a single bond, O, —CH$_2$—, —(CH$_2$)$_2$—, —CH$_2$O—, —(CH$_2$)$_2$O—, —CH$_2$S—, —CH$_2$N(R$^{20}$)—, —C(O)N(R$^{20}$)—, —N(R$^{20}$)C(O)O(CH$_2$)$_n$—, —CH$_2$CH(OH)— or N(R$^{20}$)(CH$_2$)$_n$—.

12. A compound as claimed in claim 1, wherein B represents optionally unsaturated, linear or branched, $C_{1-4}$ alkylene (which group is also optionally interrupted by O).

13. A compound as claimed in claim 1, wherein, when the bispidine nitrogen bearing B also bears a $C_{1-4}$ alkyl group, thus forming a quaternary ammonium salt, the alkyl group is methyl.

14. A compound as claimed in claim 1, wherein, when $R^9$ represents —(CH$_2$)$_q$Cy$^1$, q is 0, 1 or 2 and Cy$^1$ contains at least one nitrogen atom.

15. A pharmaceutical formulation comprising a compound as defined in claim 1 in admixture with a pharmaceutically-acceptable adjuvant, diluent or carrier.

16. A method of prophylaxis or treatment of an arrhythmia which method comprises administration of a therapeutically effective amount of a compound as defined in claim 1 to a person suffering from, or susceptible to, such a condition.

17. A process for the preparation of a compound of formula I as defined in claim 1 which comprises:

(a) reaction of a compound of formula II,

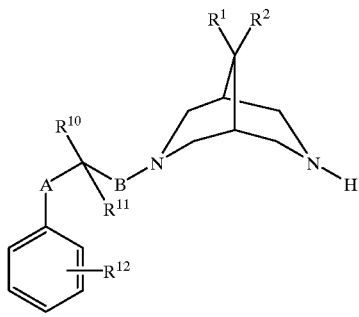

II wherein $R^1$, $R^2$, $R^{10}$, $R^{11}$, $R^{12}$, A and B are as defined in claim 1 with a compound of formula III, $$R^9XC(O)L^1 \quad\quad III$$

wherein $L^1$ represents a leaving group and $R^9$ and X are as defined in claim 1;

(b) for compounds of formula I in which B represents $CH_2$ and $R^{10}$ represents OH, reaction of a compound of formula IV,

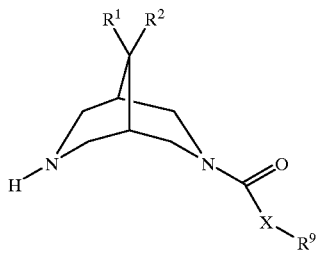

IV wherein $R^1$, $R^2$, $R^9$ and X are as defined in claim 1, with a compound of formula V,

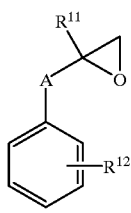

V wherein $R^{11}$, $R^{12}$ and A are as defined in claim 1;

(c) reaction of a compound of formula IV, as defined above, with a compound of formula VI,

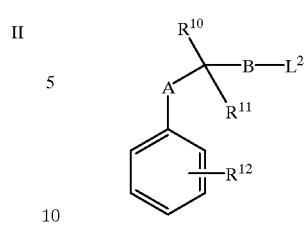

VI wherein $L^2$ represents a leaving group and $R^{10}$, $R^{11}$, $R^{12}$, A and B are as defined in claim 1;

(d) for compounds of formula I in which $R^{11}$ represents H, reduction of a compound of formula VIII,

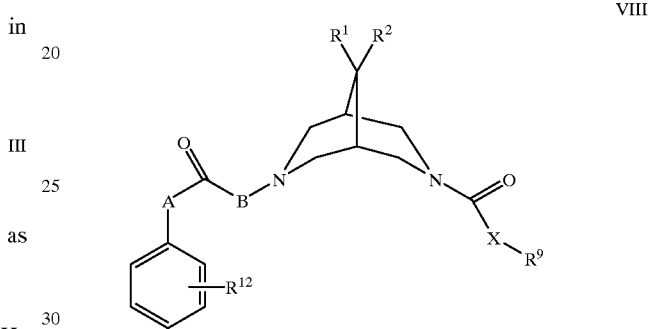

VIII wherein $R^1$, $R^2$, $R^9$, $R^{12}$, A, B and X are as defined in claim 1;

(e) for compounds of formula I in which $R^1$ and $R^2$ both represent H, reduction of a corresponding compound of formula IX,

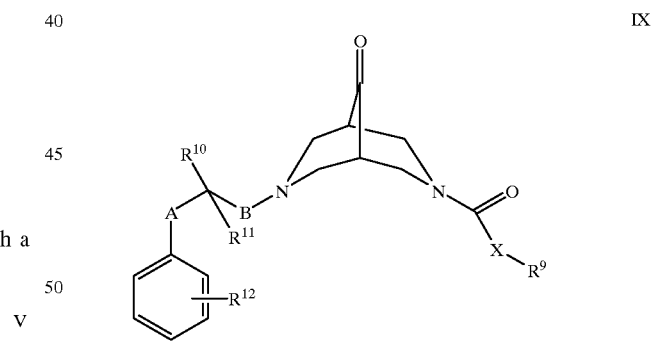

IX wherein $R^9$, $R^{10}$, $R^{11}$, $R^{12}$, X, A and B are as defined in claim 1, and in which the C=O group may be activated;

(f) for compounds of formula I in which $R^1$ and $R^2$ together represent $-O(CH_2)_2O-$, reaction of a corresponding compound of formula IX, as defined above, with ethane-1,2-diol;

(g) for compounds of formula I which are bispidine-nitrogen N-oxide derivatives, oxidation of the corresponding bispidine nitrogen of a corresponding compound of formula I;

(h) for compounds of formula I which are $C_{1-4}$ alkyl quaternary ammonium salt derivatives, in which the alkyl group is attached to a bispidine nitrogen, reaction, at the bispidine nitrogen, of a corresponding compound of formula I with a compound of formula XI, $$R^b Hal \qquad XI$$

wherein $R^b$ represents $C_{1-4}$ alkyl and Hal represent Cl, Br or I;

(i) for compounds of formula I in which $R^{10}$ and $R^{11}$ represent H, B represents $C_{1-6}$ alkylene and A represents $-N(R^{20})(CH_2)_n-$, reaction of a compound of formula XII,

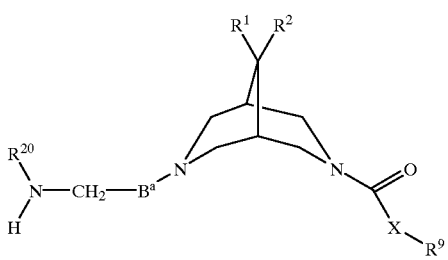

XII wherein $B^a$ represents $C_{1-6}$ alkylene and $R^1$, $R^2$, $R^9$, $R^{20}$ and X are as defined in claim 1, with a compound of formula XIII,

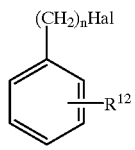

XIII wherein $R^{12}$ and n are as defined in claim 1 and Hal is as defined above;

(j) reaction of a compound of formula II, as defined above, with a compound of formula XIV, $$R^9 XH \qquad XIV$$

wherein $R^9$ and X are as defined in claim 1, in the presence of 1,1'-carbonyldiimidazole; or (k) conversion of one $R^{12}$ substituent to another.

18. A compound of formula IV

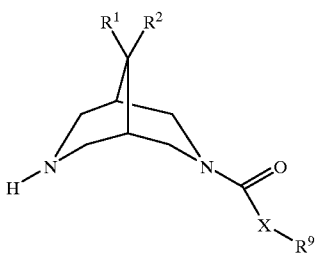

IV wherein $R^1$ and $R^2$ independently represent H, $C_{1-4}$ alkyl or together form $-O-(CH_2)_2-O-$, $-(CH_2)_4-$ or $-(CH_2)_5-$; $R^9$ represents $C_{1-12}$ alkyl, phenyl, naphthyl, $C_{1-3}$ alkylphenyl (which four groups are all optionally substituted or terminated by one or more substituents selected from the group consisting of $-OH$, halo, cyano, nitro, $C_{1-4}$ alkyl or $C_{1-4}$ alkoxy) or $-(CH_2)_q Cy^1$; q represents 0, 1, 2 or 3 and $Cy^1$ represents a five to seven-membered heterocyclic ring containing one or more heteroatom selected from O, N or S, which ring is optionally substituted by one or more substituent selected from $C(O)R^{21}$ or $C(O)OR^{22}$ wherein $R^{21}$ and $R^{22}$ independently represent H or $C_{1-6}$ alkyl; and X represents O or S; or a protected derivative thereof.

19. A compound of formula IX

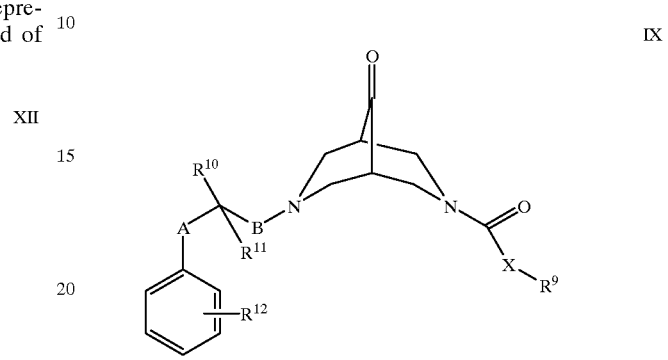

IX wherein $R^9$ represents $C_{1-12}$ alkyl, phenyl, naphthyl, $C_{1-3}$ alkylphenyl (which four groups are all optionally substituted or terminated by one or more substituents selected from the group consisting of $-OH$, halo, cyano, nitro, $C_{1-4}$ alkyl or $C_{1-4}$ alkoxy) or $-(CH_2)_q Cy^1$ wherein q represents 0, 1, 2 or 3 and $Cy^1$ represents a five to seven-membered heterocyclic ring containing one or more heteroatom selected from O, N or S, which ring is optionally substituted by one or more substituent selected from $C(O)R^{21}$ or $C(O)OR^{22}$ wherein $R^{21}$ and $R^{22}$ independently represent H or $C_{1-6}$ alkyl;

$R^{10}$ represents H or $-OH$;

$R^{11}$ represents H or $C_{1-4}$ alkyl;

$R^{12}$ represents one or more optional substituents selected from OH, cyano, halo, amino, nitro, $C_{1-6}$ alkyl, $C_{1-6}$ alkoxy, $-N(H)S(O)_2R^{16}$, $-OS(O)_2R^{16a}$, $-N(H)C(O)N(H)R^{17}$ or $-C(O)N(H)R^{18}$; wherein $R^{16}$ and $R^{16a}$ independently represent H or $C_{1-4}$ alkyl and $R^{17}$ and $R^{18}$ independently represent H or $C_{1-6}$ alkyl;

X represents O or S;

A represents a single bond, $C_{1-4}$ alkylene, $-(CH_2)_n N(R^{20})-$, $-(CH_2)_n S(O)_p-$, $-(CH_2)_n O-$ (in which three latter groups, the $-(CH_2)_n-$ group is attached to the carbon atom bearing $R^{10}$ and $R^{11}$), $-C(O)N(R^{20})-$ (in which latter group, the $-C(O)-$ group is attached to the carbon atom bearing $R^{10}$ and $R^{11}$), $-N(R^{20})C(O)O(CH_2)_n-$, $-N(R^{20})(CH_2)_n-$ (in which two latter groups, the $N(R^{20})$ group is attached to the carbon atom bearing $R^{10}$ and $R^{11}$) or $-(CH_2)_m C(H)(OH)(CH_2)_n-$ (in which latter group, the $(CH_2)_m-$ group is attached to the carbon atom bearing $R^{10}$ and $R^{11}$), wherein $R^{20}$ represents H or $C_{1-4}$ alkyl;

m represents 1, 2 or 3;

n represents 0, 1, 2, 3 or 4;

p represents 0, 1 or 2;

B represents a single bond, $C_{1-6}$ alkylene, $-N(R^{23})(CH_2)_r-$ or $O(CH_2)_r-$ (in which two latter groups, the $-(CH_2)_r$ group is attached to the bispidine nitrogen atom) wherein $R^{23}$ represents H or $C_{1-4}$ alkyl and r represents 0, 1, 2, 3 or 4; or a protected derivative thereof.

20. A compound of formula XVI,

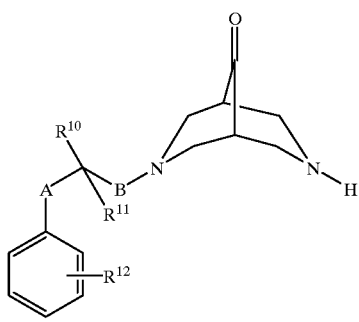

XVI wherein $R^{10}$ represents H or —OH;

$R^{11}$ represents H or $C_{1-4}$ alkyl;

$R^{12}$ represents one or more optional substituents selected from OH, cyano, halo, amino, nitro, $C_{1-6}$ alkyl, $C_{1-6}$ alkoxy, —N(H)S(O)$_2$R$^{16}$, —OS(O)$_2$R$^{16a}$, —N(H)C(O)N(H)R$^{17}$ or —C(O)N(H)R$^{18}$ wherein $R^{16}$ and $R^{16a}$ independently represent H or $C_{1-4}$ alkyl and $R^{17}$ and $R^{18}$ independently represent H or $C_{1-6}$ alkyl;

A represents a single bond, $C_{1-4}$ alkylene, —(CH$_2$)$_n$N(R$^{20}$)—, —(CH$_2$)$_n$S(O)$_p$—, —(CH$_2$)$_n$O— (in which three latter groups, the —(CH$_2$)$_n$— group is attached to the carbon atom bearing $R^{10}$ and $R^{11}$), —C(O)N(R$^{20}$)— (in which latter group, the —C(O)— group is attached to the carbon atom bearing $R^{10}$ and $R^{11}$), —N(R$^{20}$)C(O)O(CH$_2$)$_n$—, —N(R$^{20}$)(CH$_2$)$_n$— (in which two latter groups, the N(R$^{20}$) group is attached to the carbon atom bearing $R^{10}$ and $R^{11}$) or —(CH$_2$)$_m$C(H)(OH)(CH$_2$)$_n$— (in which latter group, the (CH$_2$)$_m$— group is attached to the carbon atom bearing $R^{10}$ and $R^{11}$) wherein $R^{20}$ represents H or $C_{1-4}$ alkyl;

m represents 1, 2 or 3;

n represents 0, 2, 3 or 4;

p represents 0, 1 or 2;

B represents a single bond, $C_{1-6}$ alkylene, N(R$^{23}$)(CH$_2$)$_r$— or —O(CH$_2$)$_r$— (in which two latter groups, the —(CH$_2$)$_r$ group is attached to the bispidine nitrogen atom) wherein $R^{23}$ represents H or $C_{1-4}$ alkyl and r represents 0, 1, 2, 3 or 4; or a protective derivative thereof, provided that when both $R^{10}$, and $R^{11}$ represent hydrogen, both A and B do not represent a single bond.

21. A compound of formula XVIII,

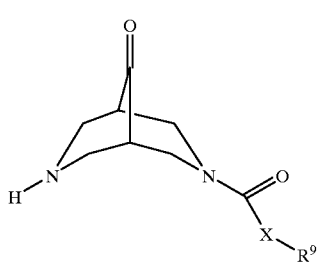

XVIII wherein $R^9$ represents $C_{1-12}$ alkyl, phenyl, naphthyl, $C_{1-3}$ alkylphenyl (which four groups are all optionally substituted or terminated by one or more substituents selected from the group consisting of —OH, halo, cyano, nitro, $C_{1-4}$ alkyl or $C_{1-4}$ alkoxy) or —(CH$_2$)$_q$Cy$^1$ wherein q represents 0, 1, 2 or 3 and Cy$^1$ represents a five to seven-membered heterocyclic ring containing one or more heteroatom selected from O, N or S, which ring is optionally substituted by one or more substituent selected from C(O)R$^{21}$ or C(O)OR$^{22}$ wherein $R^{21}$ and $R^{22}$ independently represent H or $C_{1-6}$ alkyl; and X represents O or S.

22. A process as claimed in claim 21, in which the reaction is carried out in the presence of an organic acid.

23. A process as claimed in claim 22, in which the organic acid is acetic acid.

24. A process for the preparation of a compound of formula IX as defined in claim 19, which comprises reaction of a compound of formula (XXIX),

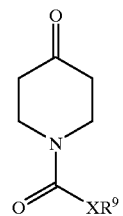

XXIX wherein $R^9$ and X are as defined in claim 19 with a compound of formula XXXI,

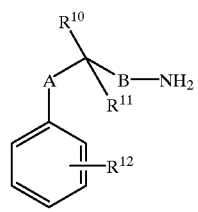

XXXI wherein $R^{10}$, $R^{11}$, $R^{12}$, A and B are as defined in claim 19, in the presence of a formaldehyde.

25. A process for the preparation of a compound of formula XVI as defined in claim 20, which comprises reaction of 4-piperidone and a compound of formula XXXI,

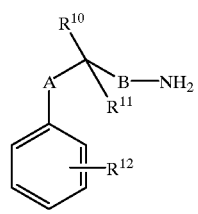

XXXI wherein $R^{10}$, $R^{11}$, $R^{12}$, A and B are as defined in claim 20, in the presence of a formaldehyde.

26. A process for the preparation of a compound of formula XVIII as defined in claim 21, which comprises reaction of a compound of formula of XXIX,

XXIX

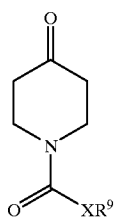

wherein R⁹ and X are as defined in claim 21 with $NH_3$, in the presence of a formaldehyde.

27. A process as claimed in claim 25 in which the reaction is carried out in the presence of an organic acid.

28. A process as claimed in claim 27 in which the organic acid is acetic acid.

29. A process as claimed in claim 26 in which the reaction is carried out in the presence of an organic acid.

30. A process as claimed in claim 29 in which the organic acid is acetic acid.

* * * * *